US008889371B2

(12) United States Patent
Miasnikov et al.

(10) Patent No.: US 8,889,371 B2
(45) Date of Patent: Nov. 18, 2014

(54) LIPOLYTIC ENZYME: USES THEREOF IN THE FOOD INDUSTRY

(75) Inventors: Andrei Miasnikov, Mountain View, CA (US); Jørn Borch Søe, Tilst (DE); Jørn Dalgaard Mikkelsen, Hvidovre (DE); Mira Povelainen, Helsinki (FI); Virve Pitkanen, Espoo (FI)

(73) Assignee: Dupont Nutrition Biosciences APS, Copenhagen (DE)

( * ) Notice: Subject to any disclaimer, the term of this patent is extended or adjusted under 35 U.S.C. 154(b) by 873 days.

(21) Appl. No.: 12/697,718

(22) Filed: Feb. 1, 2010

(65) Prior Publication Data
US 2011/0086131 A1 Apr. 14, 2011

Related U.S. Application Data

(60) Division of application No. 11/623,607, filed on Jan. 16, 2007, now Pat. No. 7,666,618, which is a continuation-in-part of application No. PCT/IB2005/002602, filed on Jul. 18, 2005.

(60) Provisional application No. 60/591,185, filed on Jul. 26, 2004.

(30) Foreign Application Priority Data

Jul. 16, 2004 (GB) .................................. 0416035.4
Jul. 7, 2005 (GB) .................................. 0513859.9

(51) Int. Cl.
*C12N 9/20* (2006.01)
(52) U.S. Cl.
USPC ........................................... 435/18; 435/198
(58) Field of Classification Search
CPC .......... A21D 8/042; A23J 7/00; C12N 9/1029
USPC .................................................. 435/18, 198
See application file for complete search history.

(56) References Cited

U.S. PATENT DOCUMENTS

| | | |
|---|---|---|
| 2,888,385 A | 5/1959 | Grandel |
| 3,260,606 A | 7/1966 | Azuma |
| 3,368,903 A | 2/1968 | Johnson |
| 3,520,702 A | 7/1970 | Menzi |
| 3,634,195 A | 1/1972 | Melachouris |
| 3,652,397 A | 3/1972 | Pardun |
| 3,677,902 A | 7/1972 | Aunstrup |
| 3,817,837 A | 6/1974 | Rubenstein et al. |
| 3,850,752 A | 11/1974 | Schuurs et al. |
| 3,852,260 A | 12/1974 | Knutsen |
| 3,939,350 A | 2/1976 | Kronick et al. |
| 3,973,042 A | 8/1976 | Kosikowski |
| 3,996,345 A | 12/1976 | Ullman et al. |
| 4,034,124 A | 7/1977 | Van Dam |
| 4,065,580 A | 12/1977 | Feldman |
| 4,160,848 A | 7/1979 | Vidal |
| 4,202,941 A | 5/1980 | Terada |
| 4,275,149 A | 6/1981 | Litman et al. |
| 4,277,437 A | 7/1981 | Maggio |
| 4,366,241 A | 12/1982 | Tom et al. |
| 4,399,218 A | 8/1983 | Gauhl |
| 4,567,046 A | 1/1986 | Inoue |
| 4,683,202 A | 7/1987 | Mullis |
| 4,689,297 A | 8/1987 | Good |
| 4,707,291 A | 11/1987 | Thom |
| 4,707,364 A | 11/1987 | Barach |
| 4,708,876 A | 11/1987 | Yokoyama |
| 4,798,793 A | 1/1989 | Eigtved |
| 4,808,417 A | 2/1989 | Masuda |
| 4,810,414 A | 3/1989 | Huge-Jensen |
| 4,814,331 A | 3/1989 | Kerkenaar |
| 4,816,567 A | 3/1989 | Cabilly et al. |
| 4,818,695 A | 4/1989 | Eigtved |
| 4,826,767 A | 5/1989 | Hansen |
| 4,865,866 A | 9/1989 | Moore |
| 4,904,483 A | 2/1990 | Christensen |
| 4,916,064 A | 4/1990 | Derez |
| 5,112,624 A | 5/1992 | Johna |
| 5,213,968 A | 5/1993 | Castle |
| 5,219,733 A | 6/1993 | Myojo |
| 5,219,744 A | 6/1993 | Kurashige |
| 5,232,846 A | 8/1993 | Takeda |

(Continued)

FOREIGN PATENT DOCUMENTS

| | | |
|---|---|---|
| AR | 249546 | 12/1996 |
| AR | P000105426 | 10/2000 |

(Continued)

OTHER PUBLICATIONS

AACC Method 54-21 Farinograph Method for Flour, from Physical Dough Tests supplied by The British Library, Nov. 3, 1999.
Anderson D, "A Primer in Oils Processing Technology" in Bailey's Industrial Oil and Fat Products, Sixth edition, John Wiley, 2005, vol. 5, chapter 1, p. 1-56. ISBN 978047138401.
Anguita et al, "Purification, Gene Cloning, Amino Acid Sequence Analysis, and Expression of an Extracellular Lipase from an *Aeromonas hydrophila* Human Isolate", Appl. Environ. Microbiol., vol. 59, No. 8, p. 2411-2417, Aug. 1993.
"AOAC Official method 999.10 (Lead, Cadmium, Zinc, Copper, and Iron in Foods Atomic absorption Spectrophotometry after Microwave Digestion), First Action 1999 NMKL-AOAC Method", AOAC International, pp. 1-3, 2002.
AOCS Method 2c-25 "1997 Moisture and Volatile Matter Air Oven Method" Sampling and Analysis of Commercial Fats and Oils, obtained from The British Library, p. 1, 1997.

(Continued)

Primary Examiner — Tekchand Saidha
(74) Attorney, Agent, or Firm — Vedder Price P.C.; Thomas J. Kowalski; Deborah L. Lu

(57) ABSTRACT

The invention encompasses the use of a lipolytic enzyme obtainable from one of the following genera: *Streptomyces, Corynebacterium* and *Thermobifida* in various methods and uses, wherein the lipolytic enzyme hydrolyzes a glycolipid or a phospholipid or transfers an acyl group from a glycolipid or phospholipids to an acyl acceptor. The present invention also relates to a lipolytic enzyme that hydrolyzes at least a galactolipid or transfers an acyl group from a galactolipid to one or more acyl acceptor substrates, wherein the enzyme is obtainable from *Corynebacterium* species.

6 Claims, 15 Drawing Sheets

(56) References Cited

U.S. PATENT DOCUMENTS

| | | |
|---|---|---|
| 5,264,367 A | 11/1993 | Aalrust |
| 5,273,898 A | 12/1993 | Ishii |
| 5,288,619 A | 2/1994 | Brown |
| 5,290,694 A | 3/1994 | Nakanishi |
| 5,310,679 A | 5/1994 | Artiss et al. |
| 5,378,623 A | 1/1995 | Hattori |
| 5,523,237 A | 6/1996 | Budtz |
| 5,536,661 A | 7/1996 | Boel |
| 5,558,781 A | 9/1996 | Buchold |
| 5,650,188 A | 7/1997 | Gaubert |
| 5,674,707 A | 10/1997 | Hintz et al. |
| 5,677,160 A | 10/1997 | Oester |
| 5,695,802 A | 12/1997 | Van Den Ouweland |
| 5,716,654 A | 2/1998 | Groenendaal |
| 5,741,665 A | 4/1998 | Kato et al. |
| 5,763,383 A | 6/1998 | Hashida |
| 5,766,912 A | 6/1998 | Boel |
| 5,776,741 A | 7/1998 | Pedersen |
| 5,814,501 A | 9/1998 | Becker |
| 5,821,102 A | 10/1998 | Berka |
| 5,824,354 A | 10/1998 | Ritter et al. |
| 5,827,719 A | 10/1998 | Sandal |
| 5,830,736 A | 11/1998 | Oxenboll |
| 5,834,280 A | 11/1998 | Oxenboll |
| 5,856,163 A | 1/1999 | Hashida |
| 5,863,759 A | 1/1999 | Boel |
| 5,869,438 A | 2/1999 | Svendsen |
| 5,874,558 A | 2/1999 | Boel |
| 5,879,920 A | 3/1999 | Dale |
| 5,892,013 A | 4/1999 | Svendsen |
| 5,914,306 A | 6/1999 | Svendsen |
| 5,916,619 A | 6/1999 | Miyazaki |
| 5,919,746 A | 7/1999 | Hirayama |
| 5,929,017 A | 7/1999 | Gormsen |
| 5,965,384 A | 10/1999 | Boel |
| 5,965,422 A | 10/1999 | Loffler |
| 5,976,855 A | 11/1999 | Svendsen |
| 5,989,599 A | 11/1999 | Chmiel |
| 5,990,069 A | 11/1999 | Andre |
| 6,001,586 A | 12/1999 | Schellenberger |
| 6,001,640 A | 12/1999 | Loeffler |
| 6,020,180 A | 2/2000 | Svendsen |
| 6,066,482 A | 5/2000 | Steffens |
| 6,074,863 A | 6/2000 | Svendsen |
| 6,103,505 A | 8/2000 | Clausen |
| 6,110,508 A | 8/2000 | Olesen |
| 6,140,094 A | 10/2000 | Loffler |
| 6,143,543 A | 11/2000 | Michelsen |
| 6,143,545 A | 11/2000 | Clausen |
| 6,146,869 A | 11/2000 | Harris |
| 6,156,548 A | 12/2000 | Christensen |
| 6,180,406 B1 | 1/2001 | Stemmer |
| 6,254,645 B1 | 7/2001 | Kellis |
| 6,254,903 B1 | 7/2001 | Schuster et al. |
| 6,344,328 B1 | 2/2002 | Short |
| 6,350,604 B1 | 2/2002 | Hirayama |
| 6,358,543 B1 | 3/2002 | Soe |
| 6,361,974 B1 | 3/2002 | Short |
| 6,365,204 B1 | 4/2002 | Spendler |
| 6,432,898 B1 | 8/2002 | Rey |
| 6,495,357 B1 | 12/2002 | Fuglsang |
| 6,506,588 B2 | 1/2003 | Tsutsumi |
| 6,509,182 B2 | 1/2003 | Tsutsumi |
| 6,511,837 B2 | 1/2003 | Tsutsumi |
| 6,514,739 B1 | 2/2003 | Udagawa |
| 6,558,715 B1 | 5/2003 | Rey |
| 6,582,942 B1 | 6/2003 | Christensen |
| 6,624,129 B1 | 9/2003 | Borch |
| 6,645,749 B2 | 11/2003 | Vind |
| 6,682,922 B2 | 1/2004 | Berka |
| 6,686,189 B2 | 2/2004 | Rey |
| 6,726,942 B2 | 4/2004 | Soe et al. |
| 6,730,346 B2 | 5/2004 | Rey |
| 6,815,190 B1 | 11/2004 | Abo |
| 6,852,346 B2 | 2/2005 | Soe |
| 6,866,837 B2 | 3/2005 | Reubi et al. |
| 6,936,289 B2 | 8/2005 | Olsen et al. |
| 6,964,944 B1 | 11/2005 | Callisen et al. |
| 6,967,035 B2 | 11/2005 | Bojsen et al. |
| 7,226,771 B2 | 6/2007 | Gramatikova et al. |
| 7,718,204 B2 | 5/2010 | Soe et al. |
| 2002/0086355 A1 | 7/2002 | Rhee et al. |
| 2002/0098536 A1 | 7/2002 | Norinobu |
| 2002/0110854 A1 | 8/2002 | Tsutsumi |
| 2002/0142434 A1 | 10/2002 | Tsutsumi |
| 2002/0168746 A1 | 11/2002 | Tsutsumi |
| 2002/0182734 A1 | 12/2002 | Diaz-Torres |
| 2003/0003561 A1 | 1/2003 | Vind |
| 2003/0028923 A1 | 2/2003 | Lardizabal |
| 2003/0040450 A1 | 2/2003 | Rey |
| 2003/0074695 A1 | 4/2003 | Farese |
| 2003/0100092 A1 | 5/2003 | Berka |
| 2003/0119164 A1 | 6/2003 | Udagawa |
| 2003/0148495 A1 | 8/2003 | Hastrup |
| 2003/0180418 A1 | 9/2003 | Rey |
| 2003/0185939 A1 | 10/2003 | Nielsen |
| 2003/0215544 A1 | 11/2003 | Nielsen |
| 2004/0005399 A1 | 1/2004 | Chakrabarti |
| 2004/0076717 A1 | 4/2004 | Campbell et al. |
| 2004/0142441 A1 | 7/2004 | Weiss et al. |
| 2004/0235106 A1 | 11/2004 | Kapeller-Libermann |
| 2005/0059130 A1 | 3/2005 | Bojsen |
| 2005/0059131 A1 | 3/2005 | Bisgard-Frantzen |
| 2005/0118697 A1 | 6/2005 | Budolfsen |
| 2005/0142647 A1 | 6/2005 | Wassell et al. |
| 2006/0040357 A1 | 2/2006 | Bardaru et al. |
| 2006/0075518 A1 | 4/2006 | Yaver et al. |
| 2006/0141457 A1 | 6/2006 | Lindqvist et al. |
| 2007/0026106 A1 | 2/2007 | Kreij et al. |
| 2007/0122525 A1 | 5/2007 | Kreij |
| 2008/0063783 A1 | 3/2008 | Kreij et al. |
| 2008/0070287 A1 | 3/2008 | Soe et al. |
| 2008/0131936 A1 | 6/2008 | Miasnikow et al. |
| 2008/0187643 A1 | 8/2008 | Horlacher |

FOREIGN PATENT DOCUMENTS

| | | |
|---|---|---|
| AR | P040101441 | 4/2004 |
| AT | 110 768 | 8/1987 |
| AU | 570720 | 9/1984 |
| AU | 723031 | 4/1998 |
| AU | 754470 | 11/1999 |
| BR | 8404421-7 | 4/1984 |
| CA | 1270781 | 6/1990 |
| CA | 2012723 | 9/1990 |
| CA | 2134597 | 10/1994 |
| CA | 2224143 | 12/1996 |
| CA | 2 403 025 | 4/2004 |
| CA | 2403025 | 4/2004 |
| CN | 97181706.5 | 8/2004 |
| CN | 101200754 | 12/2007 |
| DE | 2817087 | 11/1978 |
| DE | 19620649 | 11/1997 |
| DE | 0897667 | 2/1999 |
| DE | 69129988 | 3/1999 |
| DE | 69528070 | 6/2001 |
| DE | 69330066 | 10/2001 |
| DE | 10018787 | 5/2002 |
| DE | 69527835 | 4/2003 |
| DE | 69904161 | 7/2003 |
| DE | 69716711 | 9/2003 |
| DE | 69531538 | 6/2004 |
| DE | 69819782 | 9/2004 |
| DK | 3106.200 | 1/1989 |
| DK | 157560 | 1/1990 |
| DK | PA0888/92 | 7/1992 |
| DK | 0217/94 | 2/1994 |
| DK | PA0830/95 | 7/1995 |
| DK | PA1096/95 | 9/1995 |
| DK | 152763 | 3/1998 |
| DK | PA0543/98 | 4/1998 |
| DK | PA199801572 | 11/1998 |
| DK | PA5677000 | 12/1998 |
| DK | PA199801604 | 12/1998 |

(56) References Cited

FOREIGN PATENT DOCUMENTS

| | | |
|---|---|---|
| DK | PA199901736 | 12/1999 |
| DK | PA200000989 | 6/2000 |
| DK | PA200000991 | 6/2000 |
| DK | PA200100285 | 2/2001 |
| DK | PA200100843 | 5/2001 |
| DK | EP659049 | 6/2001 |
| DK | EP0784674 | 11/2002 |
| DK | EP0869167 | 1/2003 |
| DK | EP1073339 | 1/2003 |
| DK | PA200300634 | 4/2003 |
| DK | EP0746608 | 10/2003 |
| DK | EP1042458 | 3/2004 |
| EP | 0064855 | 11/1982 |
| EP | 0010296 | 12/1982 |
| EP | 0109244 | 5/1984 |
| EP | 0130064 | 1/1985 |
| EP | 0140542 | 5/1985 |
| EP | 0167309 | 1/1986 |
| EP | 0171995 | 2/1986 |
| EP | 0205208 | 12/1986 |
| EP | 0206390 | 12/1986 |
| EP | 0214761 | 3/1987 |
| EP | 0257388 | 3/1988 |
| EP | 0260573 | 3/1988 |
| EP | 0334462 | 9/1989 |
| EP | 0195311 | 6/1990 |
| EP | 0375102 | 6/1990 |
| EP | 0426211 | 5/1991 |
| EP | 0445692 | 9/1991 |
| EP | 0449375 | 10/1991 |
| EP | 0468731 | 1/1992 |
| EP | 0493045 | 7/1992 |
| EP | 0583265 | 10/1992 |
| EP | 0513709 | 11/1992 |
| EP | 0542351 | 5/1993 |
| EP | 0558112 | 9/1993 |
| EP | 0238023 | 11/1993 |
| EP | 0258068 | 11/1993 |
| EP | 0575133 | 12/1993 |
| EP | 0580252 | 1/1994 |
| EP | 0258068 | 8/1994 |
| EP | 0622446 | 11/1994 |
| EP | 0652289 | 5/1995 |
| EP | 0654527 | 5/1995 |
| EP | 0396162 | 9/1995 |
| EP | 0687414 | 12/1995 |
| EP | 0585988 | 3/1996 |
| EP | 0721981 | 7/1996 |
| EP | 0752008 | 1/1997 |
| EP | 0776604 | 6/1997 |
| EP | 0531104 | 8/1997 |
| EP | 0808903 | 11/1997 |
| EP | 0682116 | 12/1997 |
| EP | 0812910 | 12/1997 |
| EP | 0305216 | 3/1998 |
| EP | 0847701 | 6/1998 |
| EP | 0548228 | 8/1998 |
| EP | 0866796 | 9/1998 |
| EP | 0702712 | 12/1998 |
| EP | 0882797 | 12/1998 |
| EP | 0913092 | 5/1999 |
| EP | 0913468 | 5/1999 |
| EP | 0321811 | 12/1999 |
| EP | 1131416 | 6/2000 |
| EP | 0739985 | 11/2000 |
| EP | 1057415 | 12/2000 |
| EP | 1071734 | 1/2001 |
| EP | 0659049 | 3/2001 |
| EP | 1103606 | 5/2001 |
| EP | 1108360 | 6/2001 |
| EP | 1138763 | 10/2001 |
| EP | 1145637 | 10/2001 |
| EP | 0191217 | 2/2002 |
| EP | 0869167 | 2/2002 |
| EP | 1193314 | 4/2002 |
| EP | 0746618 | 8/2002 |
| EP | 1233676 | 8/2002 |
| EP | 0648263 | 9/2002 |
| EP | 0784674 | 9/2002 |
| EP | 1073339 | 11/2002 |
| EP | 1275711 | 1/2003 |
| EP | 1285969 | 2/2003 |
| EP | 1298205 | 4/2003 |
| EP | 0635053 | 6/2003 |
| EP | 0675944 | 6/2003 |
| EP | 0817838 | 6/2003 |
| EP | 1280919 | 6/2003 |
| EP | 0746608 | 8/2003 |
| EP | 0851913 | 5/2004 |
| EP | 1 202 562 | 6/2004 |
| EP | 1262562 | 6/2004 |
| EP | 1433852 | 6/2004 |
| EP | 0977869 | 7/2004 |
| EP | 0743017 | 9/2004 |
| EP | 0675949 | 10/2004 |
| EP | 0880590 | 10/2004 |
| EP | 0897423 | 10/2004 |
| EP | 1466980 | 10/2004 |
| EP | 0839186 | 11/2004 |
| EP | 1162889 | 2/2005 |
| EP | 1532863 | 5/2005 |
| EP | 1559788 | 8/2005 |
| EP | 1363506 | 11/2005 |
| EP | 1 624 047 A1 | 2/2006 |
| EP | 1 624 047 B1 | 10/2006 |
| EP | 1762622 | 3/2007 |
| EP | 1788080 | 5/2007 |
| ES | 535608 | 9/1984 |
| ES | 535602 | 10/1984 |
| ES | 535609 | 3/1985 |
| GB | 1086550 | 10/1967 |
| GB | 1442418 | 7/1976 |
| GB | 1577933 | 10/1980 |
| GB | 2 264 429 | 9/1993 |
| GB | 0028701.1 | 11/2000 |
| GB | 2358784 | 8/2001 |
| GB | 0301117.8 | 1/2003 |
| GB | 0301118.6 | 1/2003 |
| GB | 0301119.4 | 1/2003 |
| GB | 0301120.2 | 1/2003 |
| GB | 0301121.0 | 1/2003 |
| GB | 0301122.8 | 1/2003 |
| GB | 2379165 | 3/2003 |
| GB | 2267033 | 11/2003 |
| GB | 0330016.7 | 12/2003 |
| JP | 59183881 | 4/1960 |
| JP | 55131340 | 10/1980 |
| JP | 57-189638 | 11/1982 |
| JP | 57-189637 | 12/1982 |
| JP | 60078529 | 5/1985 |
| JP | 62118883 | 11/1985 |
| JP | 63042691 | 8/1986 |
| JP | 62061590 | 3/1987 |
| JP | 62285749 | 12/1987 |
| JP | 10203974 | 8/1988 |
| JP | 63-219373 | 9/1988 |
| JP | 1252294 | 10/1989 |
| JP | 2-49593 | 2/1990 |
| JP | 2-153997 | 6/1990 |
| JP | 04075592 | 3/1992 |
| JP | 6014773 | 3/1992 |
| JP | 4121186 | 4/1992 |
| JP | 15626492 | 6/1992 |
| JP | 04200339 | 7/1992 |
| JP | 4300839 | 10/1992 |
| JP | 4327536 | 11/1992 |
| JP | 5211852 | 8/1993 |
| JP | 7114640 | 8/1993 |
| JP | 6345800 | 12/1994 |
| JP | 8268882 | 4/1995 |
| JP | 7231788 | 9/1995 |
| JP | 7330794 | 12/1995 |
| JP | 8143457 | 6/1996 |
| JP | 8266213 | 10/1996 |

(56) References Cited

FOREIGN PATENT DOCUMENTS

| | | |
|---|---|---|
| JP | 9040689 | 2/1997 |
| JP | 10155493 | 6/1998 |
| JP | 10155493 A | 6/1998 |
| JP | 11-228986 | 8/1999 |
| JP | 11290078 | 10/1999 |
| JP | 2000226335 | 8/2000 |
| JP | 03/024096 | 7/2001 |
| JP | 2004024199 | 1/2004 |
| JP | 3553958 | 5/2004 |
| KR | 93-700773 | 3/1993 |
| KR | 94-10252 | 10/1994 |
| KR | 95-700043 | 1/1995 |
| KR | 95-702583 | 6/1995 |
| KR | 96-704602 | 8/1996 |
| KR | 2001-7012115 | 9/2001 |
| KR | 2003-7008997 | 10/2003 |
| NL | 0784674 | 12/2002 |
| NL | 0869167 | 1/2003 |
| NL | 1073339 | 2/2003 |
| NL | 0746608 | 11/2003 |
| PH | 31068 | 11/1984 |
| RU | 2140751 | 6/1997 |
| RU | 2235775 | 11/1999 |
| RU | 2001117497 | 6/2001 |
| SE | 9802548 | 7/1998 |
| TR | 200101551 | 12/1999 |
| WO | 88/02775 | 4/1988 |
| WO | 88/03365 | 5/1988 |
| WO | 89/06803 | 7/1989 |
| WO | 91/00920 | 1/1991 |
| WO | 91/06661 | 5/1991 |
| WO | 91/14772 | 10/1991 |
| WO | WO 91/17243 | 11/1991 |
| WO | 92/05249 | 4/1992 |
| WO | 92/14830 | 9/1992 |
| WO | 92/18645 | 10/1992 |
| WO | 93/01285 | 1/1993 |
| WO | 93/11249 | 6/1993 |
| WO | 93/12812 | 7/1993 |
| WO | 94/01541 | 1/1994 |
| WO | 94/04035 | 3/1994 |
| WO | 94/14940 | 7/1994 |
| WO | 94/14951 | 7/1994 |
| WO | 94/26883 | 11/1994 |
| WO | 95/06720 | 3/1995 |
| WO | 95/09909 | 4/1995 |
| WO | 95/22606 | 8/1995 |
| WO | 95/22615 | 8/1995 |
| WO | 95/22625 | 8/1995 |
| WO | 95/29996 | 11/1995 |
| WO | 95/30744 | 11/1995 |
| WO | 96/09772 | 4/1996 |
| WO | 96/13578 | 5/1996 |
| WO | 96/13579 | 5/1996 |
| WO | 96/13580 | 5/1996 |
| WO | 96/27002 | 9/1996 |
| WO | 96/28542 | 9/1996 |
| WO | 96/30502 | 10/1996 |
| WO | 96/32472 | 10/1996 |
| WO | 96/39851 | 12/1996 |
| WO | 97/04079 | 2/1997 |
| WO | 97/05219 | 2/1997 |
| WO | 97/07202 | 2/1997 |
| WO | 97/07205 | 2/1997 |
| WO | 97/11083 | 3/1997 |
| WO | 97/14713 | 4/1997 |
| WO | 97/27237 | 7/1997 |
| WO | 97/27276 | 7/1997 |
| WO | 97/41212 | 11/1997 |
| WO | 97/41735 | 11/1997 |
| WO | 97/41736 | 11/1997 |
| WO | WO 98/00029 | 1/1998 |
| WO | 98/08939 | 3/1998 |
| WO | 98/14594 | 4/1998 |
| WO | WO 98/13479 | 4/1998 |
| WO | WO 98/16112 | 4/1998 |
| WO | 98/18912 | 5/1998 |
| WO | 98/26057 | 6/1998 |
| WO | WO 98/23162 | 6/1998 |
| WO | 98/31790 | 7/1998 |
| WO | WO 98/31790 | 7/1998 |
| WO | 98/41623 | 9/1998 |
| WO | 98/44804 | 10/1998 |
| WO | 98/45453 | 10/1998 |
| WO | 98/50532 | 11/1998 |
| WO | 98/51163 | 11/1998 |
| WO | 98/59028 | 12/1998 |
| WO | 99/33964 | 7/1999 |
| WO | 99/34011 | 7/1999 |
| WO | 99/37782 | 7/1999 |
| WO | 99/42566 | 8/1999 |
| WO | 99/50399 | 10/1999 |
| WO | 99/53001 | 10/1999 |
| WO | 99/53769 | 10/1999 |
| WO | 99/55883 | 11/1999 |
| WO | 00/05396 | 2/2000 |
| WO | WO 00/23461 | 4/2000 |
| WO | 00/28044 | 5/2000 |
| WO | 00/32758 | 6/2000 |
| WO | 00/34450 | 6/2000 |
| WO | 00/36114 | 6/2000 |
| WO | WO 00/32758 | 6/2000 |
| WO | 00/43036 | 7/2000 |
| WO | 00/49164 | 8/2000 |
| WO | 00/58517 | 10/2000 |
| WO | 00/59307 | 10/2000 |
| WO | 00/60063 | 10/2000 |
| WO | 00/61771 | 10/2000 |
| WO | 00/71808 | 11/2000 |
| WO | 00/75295 | 12/2000 |
| WO | 01/16308 | 3/2001 |
| WO | 01/27251 | 4/2001 |
| WO | 01/29222 | 4/2001 |
| WO | WO 01/23581 | 4/2001 |
| WO | 01/34835 | 5/2001 |
| WO | WO 01/39544 | 5/2001 |
| WO | 01/39602 | 6/2001 |
| WO | 01/42433 | 6/2001 |
| WO | WO 01/39602 | 6/2001 |
| WO | 01/47363 | 7/2001 |
| WO | 01/66711 | 9/2001 |
| WO | 01/78524 | 10/2001 |
| WO | WO 01/75083 | 10/2001 |
| WO | 01/83559 | 11/2001 |
| WO | 01/83770 | 11/2001 |
| WO | 01/92502 | 12/2001 |
| WO | 02/00852 | 1/2002 |
| WO | 02/03805 | 1/2002 |
| WO | 02/06457 | 1/2002 |
| WO | WO 02/00852 | 1/2002 |
| WO | WO 02/06508 | 1/2002 |
| WO | 02/14490 | 2/2002 |
| WO | 02/24881 | 3/2002 |
| WO | 02/30207 | 4/2002 |
| WO | WO 02/39828 | 5/2002 |
| WO | 02/055679 | 7/2002 |
| WO | 02/062973 | 8/2002 |
| WO | 02/065854 | 8/2002 |
| WO | 02/066622 | 8/2002 |
| WO | 02/094123 | 11/2002 |
| WO | WO 02/094123 | 11/2002 |
| WO | 03/020923 | 3/2003 |
| WO | WO 03/020923 | 3/2003 |
| WO | WO 03/020941 | 3/2003 |
| WO | 03/040091 | 5/2003 |
| WO | 03/060112 | 7/2003 |
| WO | 03/070013 | 8/2003 |
| WO | 03/089260 | 10/2003 |
| WO | WO 03/089620 | 10/2003 |
| WO | 03/097825 | 11/2003 |
| WO | WO 03/097835 | 11/2003 |
| WO | 03/099016 | 12/2003 |
| WO | 03/100044 | 12/2003 |
| WO | 03/102118 | 12/2003 |

(56) References Cited

FOREIGN PATENT DOCUMENTS

| WO | WO 03/100044 | 12/2003 |
|---|---|---|
| WO | 2004/004467 | 1/2004 |
| WO | 2004/018660 | 3/2004 |
| WO | 2004/053039 | 6/2004 |
| WO | 2004/053152 | 6/2004 |
| WO | 2004/059075 | 7/2004 |
| WO | 2004/064537 | 8/2004 |
| WO | 2004/064987 | 8/2004 |
| WO | WO 2004/064537 | 8/2004 |
| WO | WO 2004/064987 | 8/2004 |
| WO | WO 2004/084638 | 10/2004 |
| WO | 2004/097012 | 11/2004 |
| WO | 2004/111216 | 12/2004 |
| WO | 2005/003339 | 1/2005 |
| WO | 2005/005977 | 1/2005 |
| WO | 2005/056782 | 6/2005 |
| WO | 2005/066347 | 7/2005 |
| WO | 2005/066351 | 7/2005 |
| WO | WO 2005/066347 | 7/2005 |
| WO | 2005/080540 | 9/2005 |
| WO | 2005/087918 | 9/2005 |
| WO | WO 2005/111203 | 11/2005 |
| WO | 2006/008508 | 1/2006 |
| WO | 2006/008653 | 1/2006 |
| WO | 2006/032279 | 3/2006 |
| WO | WO 2006/031699 | 3/2006 |
| WO | WO 2006/045354 | 5/2006 |
| WO | WO 2006/066590 | 6/2006 |
| WO | WO 2008/003420 | 1/2008 |
| WO | WO 2008/036863 | 3/2008 |
| WO | WO 2008/090395 | 7/2008 |
| WO | WO 2008/094847 | 8/2008 |
| WO | WO 2009/002480 | 12/2008 |
| WO | WO 2009/024736 | 2/2009 |
| WO | WO 2009/024862 | 2/2009 |
| WO | WO 2009/081094 | 7/2009 |

OTHER PUBLICATIONS

AOCS Official Method Ca 20-99: "Analysis of Phosphorus in oil by inductively Coupled Plasma Optical Emission Spectroscopy", Sampling and Analysis of Commercial Fats and Oils, obtained from The British Library, pp. 1-3, 2001.
Archer D.B. & Peberdy, The Molecular Biology of Secreted Enzyme Production by Fungi, Critical Reviews in Biotechnology, 1997, vol. 17, No. 4, p. 273-306.
Arskog and Joergensen, "Baking performance of prior art lipases from *Candida cylindracea* and *Aspergillus foeditus* and their activity on galactolipids in dough", Novozymes Report Jul. 18, 2005, pp. 1-2.
Arskog and Joergensen, "Baking performance of prior art lipases from *Humicola lanuginosa, Aspergillus tubigensis, Rhizopus delemar* and *Rhizomucor miehei*, and their activity on galactolipids in dough", Novozymes Report Jul. 17, 2005, pp. 1-8.
Aust K., "Applications of lecithin in bakery foods," AIB Research Technical Bulletin, vol. XV, issue 12, Dec. 1993, p. 1-6.
Banas A. et al., "Cellular sterol ester synthesis in plants is performed by an enzyme (Phospholipid: Sterol Acyltransferase) different from the yeast and mammalian Acyl-CoA: Sterol AcylTransferase", Journal of Biological Chemistry, 2005, vol. 280, No. 41, pp. 34626-34634.
Beggs J.D., Transformation of yeast by a replicating hybrid plasmid, Nature (London), 1978, vol. 275, p. 104.
Bessette, "Efficient folding or proteins with multiple disulphide bonds in the *Escherida coli* cytoplasm", Proc. Natl. Acad. Sci. USA, 1999, vol. 96, p. 13703-13708.
Bo Yang et al., "Optimization of Enzymatic Degumming Process for Rapseed Oil," JAOCS, 2006, vol. 83, No. 7, p. 653-658.
Bru R., López-Nicolás J.M., García-Carmona F., (1995) "Aggregation of polyunsaturated fatty acid in the presence of cyclodextrins", Colloids and Surfaces A: Physiochemical and Engineering Aspects. 97, p. 263-269.
Brunel et al, "High-Level expression of *Candida parapsilosis* lipase/acyltransferase in *Pichia pastoris*," J Biotechnology, Jul. 1, vol. 111, No. 1, p. 41-50, 2004.

Buchold H. et. al., "Enzymatische Phosphatidentfernung aus Pflanzenolen'" Technologies, 1993, vol. 95, No. 8, p. 300-304, ISSN:0931-5985.
Bylund G. (ed), 1995, Dairy Processing Handbook, Chapter 2, p. 17-42, Lund, Sweden.
Bylund G. (ed), 1995, Dairy Processing Handbook, Chapter 9, p. 227-246, Lund, Sweden.
Ceci L.N. et al, Oil recovery and lecithin production using water degumming sludge of crude soybean oils, Journal of the Science of Food and Agriculture, 2008, vol. 88, No. 14, p. 2460-2466.
Cereghino et al., Heterologous protein expression in the methylotrophic yeast *Pichia pastoris,* FEMS Microbiology Review, 2000, vol. 24, No. 1, p. 45-66.
Christou P., Genetic engineering of crop legumes and cereals: current status and recent advances, Agro-Food-Industry Hi-Tech, Mar./Apr. 1994, p. 17-27.
Davis R.H. and de Serres, Genetic and Microbiological Research Techniques for *Neurospora crassa*, Methods Enzymology, 1971, vol. 17A, p. 79-143.
EC 1.1.3.10 (downloaded—Jul. 12, 2010 from http://www.chem.qmul.ac.uk/iubmb/enzyme/EC1/1/3/10.html).
EC 1.1.3.4 (downloaded—Jul. 12, 2010 from http://www.chem.qmul.ac.uk/iubmb/enzyme/EC1/1/3/4.html).
EC 1.1.3.5 (downloaded—Nov. 16, 2009 from http://www.chem.qmul.ac.uk/iubmb/enzyme/EC1/1/3/5.html).
EC 2.3.1.43 (downloaded Apr. 21, 2009 from http://www.chem.qmul.ac.uk/iubmb/enzyme/EC2/3/1/43.html).
EC 2.4.1.19 (Downloaded Jul. 12, 2010 from http://www.chem.qmul.ac.uk/iubmb/enzyme/EC2/4/1/19.html).
EC 3.1.1.26 (downloaded—Dec. 18, 2008 from http://www.chem.qmul.ac.uk/iubmb/enzyme/EC3/1/1/26.html).
EC 3.1.1.3 (downloaded—Dec. 18, 2008 from http://www.chem.qmul.ac.uk/iubmb/enzyme/EC3/1/1/3.html).
EC 3.1.1.32 (downloaded—May 22, 2008 from http://www.chem.qmul.ac.uk/iubmb/enzyme/EC3/1/1/32.html).
EC 3.1.1.4 Phospholipase A2 enzyme Enzyme Entry 1983 (downloaded Apr. 21, 2009 from http://www.chem.qmul.ac.uk/iubmb/enzyme/EC3/1/1/4.html).
EC 3.1.1.5 (downloaded Dec. 18, 2008 from http://www.chem.qmul.ac.uk/iubmb/enzyme/EC3/1/1/5.html).
EC 3.2.1.3 (downloaded Jul. 12, 2010 from http://www.chem.qmul.ac.uk/iubmb/enzyme/EC3/2/1/3.html).
EC 3.2.1.32 (Downloaded Jul. 12, 2010 from http://www.chem.qmul.ac.uk/iubmb/enzyme/EC3/2/1/32.html).
EC 3.2.1.60 (downloaded Apr. 28, 2009 from http://www.chem.qmul.ac.uk/iubmb/enzyme/EC3/2/1/60.html).
Eliasson A-C. and Larssen K., "Chapter 2: Physiochemical Behavior of the Components of Wheat Flour", *Cereals in Breadmaking: a molecular colloidal approach*, Marcel Dekker Inc, 1993, ISBN0824788168, p. 31-45.
Genbank accession code NC_003888.1:8327480..8328367 (downloaded Apr. 21, 2009), p. 1.
Genbank accession No. AL646052 (downloaded Apr. 21, 2009), pp. 1-2.
Genbank accession No. AL939131.1:265480..266367 (downloaded Apr. 21, 2009), p. 1.
Genbank accession No. CAC42140 (downloaded Apr. 21, 2009), pp. 1-2.
NCBI Accession No. SC07513 (downloaded Apr. 21, 2009), pp. 1.
Genbank accession No. P41734 (downloaded Apr. 21, 2009), pp. 1-4.
NCBI Accession No. Z75034 (downloaded Apr. 21, 2009) p. 1-2.
Hammond E.G. et al., "Soybean Oil" in Bailey's Industrial Oil and Fat Products, Sixth edition, John Wiley, 2005, vol. 3, chapter 13, p. 577-653. ISBN 978047138401.
Hinchcliffe E., Kenny E., "Yeast as a vehicle for the expression of heterologous genes", Yeasts, 1993, vol. 5, Anthony H. Rose and J. Stuart Harrison, eds. 2nd edition, Academic Press Ltd.
Hinnen A. et al., Transformation of yeast, Proceedings of the National Academy of Sciences USA, Apr. 1978, vol. 75, No. 4, p. 1929-1933.
Hollenberg C.P. et al., Production of recombinant proteins by methylotrophic yeasts, Current Opinion in Biotechnology Oct. 1997, vol. 8, No. 5, pp. 554-560.

(56) References Cited

OTHER PUBLICATIONS

Horwell DC, "The 'peptoid' approach to the design of non-peptide, small molecular agonists and antogonists of neuropeptides", Trends Biotechnol., 1995, vol. 13, No. 4, pp. 132-134.
Hossen, Monjur, "Enzyme catalyzed synthesis of structured phospholipids with conjugated linoleic acid and plant sterols," A Dissertation by MD Monjur Hossen, May 2005, p. 1-152.
Hui, Bailey's Industrial Oil and Fat Products, 5th edition vol. 2 Edible Oil and Fat Products: Oils and Oilseeds, Wiley Interscience (1996), pp. 513-516. ISBN 0471594261.
Ito H. et al., "Transformation of Intact Yeast Cells Treated with Alkali Cations," J. Bacteriology, 1983, vol. 153, p. 163-168.
Jost R. et. al., "Milk and Dairy Products," Nestle Product Technology Center, 2007, Wiley-VCH, pp. 1-62, Konolfingen, Switzerland.
Kalscheuer et al, "Synthesis of Novel Lipids in *Saccharomyces cerevisiae* by Heterologous Expression of an Unspecific Bacterial Acyltransferase," Applied and Environmental Microbiology, vol. 70, No. 12, p. 7119-7125, 2004.
Kane, "Effects of rare codon clusters on high-level expression of heterolgous proteins in *E. coli*" Current Opinion Biotechnology, 1995, vol. 6, p. 494-500.
Kimmel, A. et al. "Preparation of cDNA and the Generation of cDNA Libraries: Overview," Methods in Enzymology, 1987, vol. 152, p. 307-316.
LaVallie T.M., 2-Methoxyestradiol Inhibits Proliferation and Induces Apoptosis Independently of Estrogen Receptors α and β, Current Opinion in Biotechnology, 1995, vol. 6, No. 5, pp. 501-506.
Leon et al., "A new approach to study starchy changes occurring the double-baking process and during bread storage," Z. Lebensn. Unters Forsch A, 1997, vol. 204 pp. 316-320.
McIntyre et al., "Distribution of Glycerophospholipid-Cholesterol Acyltransferase in Selected Bacterial Species," Journal of Bacteriology, Jul. 1979, vol. 139, No. pp. 132-136.
NCBI protein accession code AAK84028.1 GI:15082088, (downloaded Dec. 18, 2009), pp. 1-2.
NCBI protein accession code CAB39707.1 GI:4529178, (downloaded Dec. 18, 2009), pp. 1-2.
NCBI protein accession code CAB62724.1 GI:6562793, (downloaded Dec. 18, 2009), pp. 1-2.
NCBI protein accession code CAB88833.1 GI:7635996, (downloaded Dec. 18, 2009), pp. 1-2.
NCBI protein accession code CAB89450.1; GI:7672261, (downloaded Dec. 18, 2009), pp. 1-2.
NCBI protein accession code CAC01477.1 GI:9716139, (downloaded Dec. 18, 2009), pp. 1-2.
NCBI's Genbank database accession number: 11VN_A; GID:33357066, (downloaded Oct. 14, 2010), pp. 1-2.
Oil Mill Gazetteer, "Enzymatic Degumming Improves Oil Refining in China," Jul. 2005 vol. 111, p. 2-4.
Phospholipase C, E.C. 3.1.4.3, , (downloaded Sep. 8, 2009 from http://www.chem.qmul.ac.uk/iubmb/enzyme/EC3/1/4/3.html), p. 1.
Poldermans B and Schoppink P, "Controlling the baking process and product quality with enzymes", Cereal Foods World, Mar. 1999, 44 (3), p. 132-135.
Potrykus I., Gene Transfer to Plants: assessment of published approaches and results, Annu. Rev. Plant Physiol. Plant Mol. Biol., 1991, vol. 42, p. 205-225.
PreSens Manual HydroPlate® HP96U and HydroPlate® HP96C, pp. 1-15, Aug. 17, 2004.
Simon RJ et al.,"Peptoids: a modular approach to drug discovery", Proc. Natl. Acad. Sci. USA, 1992, vol. 89, No. 20, pp. 9367-9371.
Sutrisno, A. et al, "Expression of a gene Encoding Chitinase (pCA 8 ORF) from *Aeromonas* sp. No. 10S-24 in *Esxherichia coli* and Enzyme Characterization," Journal of Bioscience and Bioengineering, vol. 91, No. 6, pp. 599-602, 2001.
Szuhaj B.F., "Lecithins" in Bailey's Industrial Oil and Fat Products, Sixth edition, John Wiley, 2005, vol. 2, chapter 13, p. 361-456. ISBN 978047138401.
Tanji M.et al., "Lipase hydrolysis of milk fat and its soft fractions", Research Bulletin of Obihiro University, 2001, vol. 22, No. 2, p. 89-94.
Tilden E.B. and Hudson C.S., Preparation and Properties of the Amylases Produced by *Bacillus macerans* and *Bacillus polymyxa*, J. Bacteriology, 1942, vol. 43, p. 527-544.
Torres C.F. et al., A two steps enzymatic procedure to obtain sterol esters, tocopherols and fatty acid ethyl esters from soybean oil deodorizer distillate, Process Biochemistry, 2007, vol. 42, No. 9, p. 1335-1341.
Trueman L.J., "Heterologous Expression in Yeast," Methods Molecular Biology, vol. 49, p. 341-354 (1995).
Turner G. Vectors for generic manipulation, in Martinelli S.D, Kinghorn J.R. (editors), *Aspergillus:* 50 years on. Progress in industrial microbiology, 1994, vol. 29, p. 641-666.
Notification of Reasons for Refusal: JP Application No. 526105, Feb. 12, 2003 (Translation).
Notification of Reasons for Refusal: JP Application No. 526105, Jun. 4, 2002 (Translation).
Written Argument: JP Application No. 97181706.5, (Dec. 9, 1997) (Translation).
U.S. Appl. No. 60/083,277, filed Apr. 28, 1998, Spender, Tina, et al.
L. Barksdale, et al., Phospholipase D Activity of *Corynebacterium pseudotuberculosis* (*Corynebacterium ovis*) and *Corynebacterium ulcerans*, A Distinctive Marker Within the Genus *Corynebacterium*, Journal of Clinical Microbiology (1981) vol. 13, No. 2, p. 335-343.
K. Fossum, et al., Phospholipase D Activity in a Non-Haemolytic Coryneform Bacterium, Acta Pathologica Microbiologica Scandinavica, Section B (1963) vol. 57, No. 3, p. 295-300.
Biosis Accession No. PREV198227307136I, Malmqvist, et al., Enzymatic Hydrolysis by Bacterial Phospho Lipase C and Phospho Lipase D of Immobilized Radioactive Sphingomyelin and Phosphatidyl Choline, Acta Pathologica et Microbiologica Scandinavica Section B Microbiology (1981) vol. 89.
Kaniuga Z, Galactolipase and chilling sensitivity of plants, Acta Biochim Pol. (1997), vol. 44(1), p. 21-35.
Ostrovskaya L K et al, Spectral features of the action of galactolipase on native forms of chlorophyll, Dokl Akad Nauk SSSR, (vol. 186(4), p. 961-963) p. 59-61, (1969).
O'Sullivan et al, A Galactolipase Activity Associated with the Thylakoids of Wheat Leaves (*Triticum acstivum* L.) J Plant Physiol, vol. 313, (1987) p. 393-404.
Sakaki T et al, Purification and immunological properties of galactolipase from *Phaseolus vulgaris* leaves, Advanced Research on Plant Lipids, Proceedings of the International Symposium on Plant Lipids, 15th, Okazaki, Japan, May 12-17, 2002 (2003) p. 291-294, Publisher Kluwer Academic Publishers.
Hirayama O et al, Purification and properties of a lipid acyl-hydrolase from potato tubers, Biochim Biophys Acta. 1975, vol. 384(1), p. 127-137.
Product Sheet B1324a-GB—LecitaseR Novo, Novo Nordisk.
Rydel, Timothy J. et al., "The Crystal Structure, Mutagenesis and Activity Studies Reveal that Patatin is a Lipid Acyl Hydrolase with a Ser-Asp Catalytic Dyad", Biochemistry, 2003, vol. 42, pp. 6696-6708, NZAS—0301072.
Sakai, Norio, et al., "Human glactocerebrosidase gene: promoter analysis of the 5'-flanking region and structural organization", Biochimica et Biophysica Acta, vol. 1395, pp. 62-67, 1998.
EC 3.2.1.32 (downloaded Jul. 12, 2010).
EC 3.2.1.60 (downloaded Apr. 28, 2009).
Product Sheet_Lecitase_Novo_000033-039.
Spendler, et al., "Functionality and mechanism of a new 2nd generation lipase for baking industry"—Abstract. 2001 AACC Annual Meeting; Symposia at Charlotte, NC. Oct. 14-18, 2001.
Woolley et al., "Lipases their structure, biochemistry and application", Cambridge University Press, NZAS—00354436.
Frenken N. et al, Cloning of the *Pseudomonas glumae* lipase gene and determination of the active site residues,(1992) Appl. Envir. Microbiol. 58 3787-3791.
Hilton S, Buckley JT, Studies on the reaction mechanism of a microbial lipase acyltransferase using chemical modification and site-directed mutagenesis, J Biol Chem. Jan. 15, 1991; 266(2): 997-1000.

(56) References Cited

OTHER PUBLICATIONS

Hirose, Yoshihiko et al., "Characteristics of Immobilized Lipase PS on Chemically Modified Ceramics", Amano Pharmaceutical, NZAS—0239105.
jan-Willem F. A. Simons et al., "Cloning, purification and characterisation of the lipase from *Staphylococcus epidermidis*", Eur. J. Biochem., vol. 253, pp. 675-683, 1998, NZAS—0216239.
Kim, Hyung Kwoun, et al., Expression and characterization of Ca2+-independent lipase from *Bacillus pumilus* B26, Biochimica et Biophysica Acta, vol. 1583, 2002, pp. 205-212, NZAS—0204610.
Reetz M.T., Jaeger K.E. Overexpression, immobilization and biotechnological application of *Pseudomonas lipases*, Chem Phys Lipids. Jun. 1998; 93(1-2): 3-14.
Robertson et al, Influence of active site and tyrosine modification on the secretion oand activity of the *Aeromonas hydrophila* Lipase/Acyltransferase, Journal of Biological Chemistry, 1994, 2146-2150.
Tsuneo Yamane et al., "Glycerolysis of Fat by Lipase", Laboratory of Bioreaction Engineering, vol. 35, No. 8, 1986, NZAS—0213396.
Warmuth et al, Immobilization of a bacterial lipase,1992, Bio Forum 9, 282-283.
Hou Ching T, pH dependence and thermostability of lipases from cultures from the ARS culture collection, Journal of Industrial Microbiology, vol. 13, No. 4, 1994, pp. 242-248.
Freshzyme, Product Sheet, NZAS—0265916.
Reetz Manfred T, Lipases as practical biocatalysts, Current Opinion in Chemical Biology, Apr. 2002, vol. 6, No. 2, pp. 145-150.
Sztajer H et al., Microbial lipases in biotechnology, Acta Biotechnol, vol. 8, 1988, pp. 169-175.
Picon et al., Release of encapsulated proteinase from dehydration-rehydration liposomes by a co-encapsulated phospholipase, Biotechnology letters vol. 17 nr 10 pp. 1051-1056.
Sugatani, Junko, et al., "Studies of a Phospholipase B from *Penicillium notatum* Substrate Specificity and Properties of Active Site", Biochimica et Biophysica Acta, vol. 620, 1980, pp. 372-386, NZAS—0418825.
Sugimoto et al., Hydrolysis of phosphatidyl ethanolamine by cell fractions of *Streptococcus lactis*, Agric. Biol. Chem. 47(6), 1201-1206 (1983).
Delphine Briand et al., "Substrate Specificity of the Lipase from *Candida parapsilosis*", Lipids, 1995, vol. 30, No. 8.
"Definition of Recombined Milk", International Dairy Federation, 1979, doc. 116, p. 5.
Stryer, L., Biochemistry, 1981, $2^{nd}$ Edition, W H Freeman and Co., San Francisco.
Jennifer L. Seffemick et al., "Melamine Deaminase and Atrazine Chlorohydrolase: 98 Percent Identical but Functionally Different", Journal of Bacteriology, Apr. 2001, vol. 183, No. 8, pp. 2405-2410.
Andrzej Witkowski et al., "Conversion of a β-Ketoacyl Synthase to a Malonyl Decarboxylase by Replacement of the Active-Site Cysteine with Glutamine", Biochemistry, 1999, vol. 38, No. 6, pp. 11643-11650.
"AOCS Introduction to the Processing of Fats and Oils", American Oil Chemists Society, 2003, pp. III 16-19.
Hajime Seino et al., "Enzymatic Synthesis of Carbohydrate Esters of Fatty Acid (10 Esterification of Sucrose, Glucose, Fructose and Sorbitol", JAOCS, Nov. 1984, vol. 61, No. 11.
Roberto A. Chica et al., "Semi-rational approaches to engineering enzyme activity: combining the benefits of directed evolution and rational design", Biotechnology, 2005, vol. 16, pp. 378-384.
Garcia et al., "1, 2-Diacyl-*sn*-glycerol: Sterol Acyl Transferase from Spinach Leaves (*Spiniacia olerecea* L.)", Methods in Enzymology, vol. 71, pp. 768-772.
Anna Maria V. Garzillo et al., "Production, purification and characterization of glucose oxidase from Penicillium variabile P16[1]", Biotechnol. Appln. Biochem., 1995, vol. 22, pp. 169-178.
Patent Abstracts of Japan; Publication No. 07-079687; Publication Date Mar. 28, 1995.
Patent Abstracts of Japan; Publication No. 04-370055; Publication Date Dec. 12, 1992.
Patent Abstracts of Japan; Publication No. 48016612; Publication Date May 23, 1973.
S. Sen et al., "Developments in Directed Evolution for Improving Enzyme Functions", Appl. Biotechnol., 2007, vol. 143, No. 3, pp. 212-223.
"Purifine Enzyme", Verenium Corporation leaflet, Jan. 2008.
Jean Louis Arpigny et al., Bacterial Lipolytic Enzymes: Classification and Properties, Biochem. J. (1999) vol. 343, p. 177-183.
S.D. Bentley, et al., Complete Genome Sequence of the Model Actinomycete *Streptomyces coelicolor* A3(2), Nature (2002) vol. 417, p. 141-147.
Michael J. Brumlik, et al., Identification of the Catalytic Triad of the Lipase/Acyltransferase From *Aeromonas hydrophila*, Journal of Bacteriology (1996) vol. 178, No. 7, p. 2060-2064.
Dusica Vujaklija, et al., A Novel Streptomycete Lipase: Cloning, Sequencing and High-Level Expresion of the *Streptomyces rimosus* GDS(L)-Lipase Gene, Arch Microbiol (2002) vol. 178, p. 124-130.
Abstract: Ikeda, et al., Complete Genome Sequence and Comparative Analysis of the Industrial Microorganism *Streptomyces avermitilis*, Nature Biotechnol. (2003) vol. 21, p. 526-531.
Abstract: Accession No. ZP-00058717, NCBI Microbial Genomes Annotation Project, Hypothetical Protein From Thermobifida Fusca, EBI, Hinxton, UK (2003).
Nerland A.H., "The Nucleotide Sequence of the Gene Encoding GCAT from *Aeromonas salmonicida* SSP. Salmonicida", Journal of Fish Diseases, 1996, vol. 19, No. 2, pp. 145-150, XP008049669.
Nerland A.H., "Glycerophospholipid-cholesterol acyltransferase precursor", SwissProt, Feb. 11, 2005, XP002318368.
Buckley J. Thomas, "Substrate specificity of bacterial glycerophospholipid" Cholesterol Acyltransferase, Biochemistry, 1982, vol. 21, pp. 6699-6703.
U.S. Appl. No. 60/039,791, filed Mar. 4, 1997, Clausen.
U.S. Appl. No. 60/189,780, filed Mar. 16, 2000, Soe.
U.S. Appl. No. 60/489,441, filed Jul. 23, 2003, Kreij.
Richardson, Toby H., et al., "A Novel, High Performance Enzyme for Starch Liquefaction", The Journal of Biological Chemistry, vol. 277, No. 29, Issue of Jul. 19, pp. 25501-26507, 2002.
Roberts et al. (1992) Gene 122(1), 155-61.
Roberts, et al.; "Extracellular Lipase Production by Fungi from Sunflower Seed"; Mycologia(1987); vol. 79(2); pp. 265-273.
Robertson et al, Journal of Biological Chemistry, 1994, 2146-2150.
Rodrigues, et al.; "Short Communication: Bioseparations with Permeable Particles"; Journal of Chromatography & Biomedical Applications(1995); vol. 655; pp. 233-240.
Rogalska, Ewa, et al., "Stereoselective Hydrolysis of Triglycerides by Animal and Microbial Lipases", Chirality, vol. 5, pp. 24-30, 1993.
Rose, et al.; "CODEHOP (Consensus-Degenerate Hybrid Oligonucleotide Primer) PCR primer design"; Nucleic Acids Research(2003); vol. 31(13); pp. 3763-3766.
Rousseau, Derick, et al., "Tailoring the Textural Attributes of Butter Fat/Canola Oil Blends via Rhizopus arrhizus Lipase-Catalyzed Interesterification. 2. Modifications of Physical Properties", J. Agric. Food Chem., vol. 1998, vol. 46, pp. 2375-2381.
Rydel, Timothy J. et al., "The Crystal Structure, Mutagenesis and Activity Studies Reveal that Patatin Is a Lipid Acyl Hydrolase with a Ser-Asp Catalytic Dyad", Biochemistry, 2003, vol. 42, pp. 6696-6708.
Sahsah, Y., et al., "Enzymatic Degradation of polar lipids in *Vigna unguiculata* leaves and influence of drought stress", Physiologia Plantarum, vol. 104, pp. 577-586, 1998.
Sahsah, Y., et al., "Purification and characterization of a soluble lipolytic acylhydrolase from Cowpea (*Vigna unguiculata* L.) leaves", Biochimica et Biophysica Acta, vol. 1215, pp. 66-73, 1994.
Saiki R.K. et al Science (1988) 239, pp. 487-491.
Sakai, Norio, et al., "Human glactocerebrosidase gene: promoter analysis of the 5'-flanking region and structural organization", Biochimica et Biophysica Acta, vol. 1395, pp. 62-67, 1998.
Sakaki T et al, Advanced Research on Plant Lipids, Proceedings of the International Symposium on Plant Lipids, 15th, Okazaki, Japan, May 12-17, 2002 (2003) p. 291-294, Publisher Kluwer Academic Publishers.
Sambrook et al. Chapters 1, 7, 9, 11, 12 and 13—Molecular Cloning a laboratory manual, Cold Spring harbor Laboratory Press (1989).

(56) References Cited

OTHER PUBLICATIONS

Sambrook, J., et al. "A Laboratory Manual, Second Edition", Plasmid Vectors, 1989.
Sanchez et al., "Solution and Interface Aggregation States of *Crotalus atrox* Venom Phospholipase A2 by Two-Photon Excitation Fluorescence Correlation Spectroscopy", Biochemistry, 2001, vol. 40, pp. 6903-6911.
Sarney Douglas B. et al, "Enzymatic Synthesis of Sorbitan Esters Using a Low-Boiling-Point Azeotrope as Reaction Solvent", Biotechnology and Bioengineering, 1997, vol. 54(4).
Saxena, et al.; "Purification Strategies for Microbial Lipases"; Journal of Microbilogical Methods (2003); pp. 1-18.
Scheib et al.; "Stereoselectivity of Mucorales lipases toward triradylglycerols—A simple solution to a complex problem"; Protein Science (1999); vol. 8; pp. 215-221.
Schiller, Jurgen, et al., "Lipid analysis of human spermatozoa and seminal plasma by MALDI-TOF mass spectrometry and NMR spectroscopy—effects of freezing and thawing" Chemistry and Physics of Lipids, vol. 106, 2000, pp. 145-156.
Scopes, Robert K., "Section 8.4: Ultrafiltration" in *Protein Purification Principles and Practice, Third Edition* (1994) Springer-Verlag, New York, p. 267-9.
Sequence alignment of the nucleotide sequences of SEQ ID No. 2 of EP'167 and SEQ ID No. 7 of D20 and the amino acid sequences of SEQ ID No. 2 of EP'167 and SEQ ID No. 8 of D20.
Shehata PhD Thesis.
Shillcock, Julian C., et al., "Equilibrium structure and lateral stress distribution of amphiphilic bilayers from dissipative particle dynamics simulations", Journal of Chemical Physics, vol. 117, No. 10, Sep. 8, 2002.
Shillcock, Julian C., et al., "Tension-induced fusion of bilayer membranes and vesicles", Advance Online Publication.
Shimada et al, J. of Bioscience and Bioengineering vol. 91, No. 6, 529-538 (2001).
Shimada et al, J. of Fermentation and Bioengineering vol. 75, No. 5, 349-352 (1993).
Shimada et al, JAOCS vol. 71, No. 9, (Sep. 1994).
Shin, et al.; "Butyl-Toyopearl 650 as a New Hydrophobic Adsorbent for Water-Solualbe Enzyme Proteins"; Analytical Biochemistry(1984); vol. 138; pp. 259-261.
Shogren, M.D., et al., "Functional (Breadmaking) and Biochemical Properties of Wheat Flour Components. I. Solubilizing Gluten and Flour Protein", Cereal Chemistry, vol. 46, No. 2, Mar. 1969.
Si, Joan Qi; "New Enzymes for the Baking Industry"; Food Tech Europe (1996) pp. 60-64.
Sias B et al, Biochemistry, (2004), vol. 43(31), p. 10138-148.
Siew W.L. & Ng W.L. (1999) Influence of diglycerides on crystalisation of palm oil, in Journal of Science of Food and Agriculture 79:722-726.
Siew W.L. & Ng W.L. (2000) Differential scanning thermograms of palm oil triglycerides in the presence of diglycerides, in Journal of Oil Palm Research 12:107.
Siew W.L. (2001) Understanding the Interactions of Diacylglycerols with oil for better product performance, paper presented at the 2001 PIPOC International Palm Oil Congress—Chemistry and Technology Conference Aug. 20-23, 2001, Kuala Lumpur, Malaysia.
Skovgaard, et al.; "Comparison of Intra- and extracellualr isozyme banding patterns of *Fusarium oxysporum*"; Mycol. Res. (1998); vol. 102(9); pp. 1077-1084.
Slotboom et al Chem. Phys. Lipids 4 (1970) 15-29.
Smith, George P.; "The Progeny of sexual PCR"; Nature; vol. 370; No. 18; Aug. 4, 1994.
Smith, Timothy L., et al., "The promoter of the glucoamylase-encoding gene of *Aspergillus niger* functions in Ustilago maydis", Gene. 88, 259-262, 1990.
Soe, J.B., "Analyses of Monoglycerides and Other Emulsifiers by Gaschromatography".
Solares, Laura F., et al., "Enzymatic resolution of new carbonate intermediates for the synthesis of (S)-(+)-zopiclone", Tetrahedron: Asymmetry, vol. 13, 2002, pp. 2577-2582.
Sols and De Le Fuente, "On the substrate specificity of glucose oxidase", Biochem et Biophysica Acta (1957) 24:206-207.
Sonntag N.O.V. (1982a) Glycerolysis of Fats and methyl esters—status, review and critique, in Journal of American Oil Chemist Society 59:795-802A.
Soragni, Elisabetta, et al., "A nutrient-regulated, dual localization phospholipase A2 in the symbiotic fungus" The EMBO Journal, vol. 20, No. 18, pp. 5079-5090, 2001.
Sorensen, H.R., et al., "Effects of added enzymes on the physicochemical characteristics on fresh durum-pasta".
Sosland, Josh, "Alive and kicking", Milling & Baking News, Feb. 24, 2004.
Soumanou, Mohamed M., et al., "Two-Step Enzymatic Reaction for the Synthesis of Pure Structured Triacylglycerides", JAOCS, vol. 75, No. 6, 1998.
Spendler, et al., "Functionality and mechanism of a new 2nd generation lipase for baking industry" - Abstract. 2001 AACC Annual Meeting; Symposia at Charlotte, NC. Oct. 14-18, 2001.
Spradlin J E, Biocatalysis in Agric. Technol., ACS Symposium, 389(3), 24-43 (1989).
Sreekrishna K et al (1988) J Basic Microbiol. 28(4), 265-78.
Stadler et al., "Understanding Lipase Action and Selectivity", CCACAA, vol. 68, No. 3, pp. 649-674, 1995.
Steinstraesser, et al., "Activity of Novispirin G10 against *Pseudomonas aeruginosa* In Vitro and in Infected Burns", Antimicrobial Agents and Chemotherapy, Jun. 2002, vol. 46, No. 6, pp. 1837-1844.
Stemmer, Willem P.C.; "DNA shuffling by random fragmentation and reassembly: In vitro recombination for molecular evolution"; Proc. Natl. Acad. Sci. USA, vol. 91, pp. 10747-10751; Oct. 1994.
Stemmer, Willem P.C.; "Rapid evolution of a protein in vitro by DNA shuffling"; Affymax Research Institute, Nature, vol. 370, Aug. 4, 1994.
Sternberg, M., "Purification of Industrial Enzymes with Polyacrylic Acids", Process Biochemistry, Sep. 1976.
Strickland, James A., et al., "Inhibition of Diabrotica Larval Growth by Patatin, the Lipid Acyl Hydrolase from Potato Tubers", Plant Physiol, vol. 109, pp. 667-674, 1995.
Sudbery et al (1988) Biochem Soc Trans. 16(6), 1081-3.
Sugatani, Junko, et al., "Studies of a Phospholipase B from *Penicillium* Notatum Substrate Specificity and Properties of Active Site", Biochimica et Biophysica Acta, vol. 620, 1980, pp. 372-386.
Sugimoto et al., Agric. Biol. Chem. 47(6), 1201-1206 (1983).
Sugiyama et al., "Molecular cloning of a second phospholipase B gene, caPLB2 from *Candida albicans*", Medical Mycology, vol. 37, 1999.
Svendsen, A. "Engineered lipases for practical use", INFORM (1994) 5(5):619-623.
Svendsen, Allan, "Lipase protein engineering" Biochimica et Biophysica Acta, vol. 1543, 2000, pp. 223-238.
Svendsen, Allan, et al., "Biochemical properties of cloned lipases from the Pseudomonas family", Biochimica et Biophysica Acta, vol. 1259, 1995, pp. 9-17.
Sweigard, James A., et al., "Cloning and analysis of CUT1, a cutinase gene from *Magnaporthe grise*", Mol. Gen. Genet., 232:174-182, 1992.
Swinkels et al (1993) Antonie van Leeuwenhoek 64, 187-201.
Sztajer H et al Acta Biotechnol. vol. 8, 1988, pp. 169-175.
Talker-Huiber, Cynthia Z., et al., "Esterase EstE from *Xanthomonas vesicatoria* (Xv_EstE) is an outer membrane protein capable of hydrolyzing long-chain polar esters", Appl. Microbiol Biotechnol, 61:479-487, 2003.
Terasaki, Masaru, et al., "Glycerolipid Acyl Hydrolase Activity in the Brown Alga Cladosiphon okamuranus Tokida", Biosci. Biotechnol. Biochem., vol. 67, No. 9, pp. 1986-1989, 2003.
The New Enzyme Operatives, Ingredient Technology, 50, Aug. 1997.
Thommy L-G; Carlson, "Law and Order in Wheat Flour Dough; Colloidal Aspects of the Wheat Flour Dough and its Lipid and Protein Constitutents in Aqueous Media", Fortroligt, Lund 1981.
Thornton et at 1988 Biochem. Et Biophys. Acta. 959, 153-159.
Tiss, Aly, et al., "Effects of Gum Arabic on Lipase Interfacial Binding and Activity", Analytical Biochemistry, vol. 294, pp. 36-43, 2001.

(56) References Cited

OTHER PUBLICATIONS

Toida J et al, Bioscience, Biotechnology, and Biochemistry, Jul. 1995, vol. 59, No. 7, pp. 1199-1203.
Tombs and Blake, Biochim. Biophys (1982) 700:81-89.
Topakas, E., et al. "Purification and characterization of a feruloyl esterase from *Fusarium oxysporum* catalyzing esterification of phenolic acids in ternary water—organic solvent mixtures", Journal of Biotechnology, vol. 102, 2003, pp. 33-44.
Torossian and Bell (Biotechnol. Appl. Biochem., 1991, 13:205-211.
Tsao et al. (1973) J Supramol Struct. 1(6), 490-7.
Tsuchiya, Atsushi et al, Fems Microbiology Letters, vol. 143, pp. 63-67.
Tsuneo Yamane et al., "Glycerolysis of Fat by Lipase", Laboratory of Bioreaction Engineering, vol. 35, No. 8, 1986.
Tsychiya, Atsushi, et al., "Cloning and nucleotide sequence of the mono- and diacylglycerol lipase gene (mdlB) of Aspergillus oryzae", FEMS Microbiology Letters, vol. 143, pp. 63-67, 1996.
Turnbull, K.M., et al., "Early expression of grain hardness in the developing wheat endosperm", Planta, 2003, vol. 216, pp. 699-706.
Turner, Nigel A., et al., "At what temperature can enzymes maintain their catalytic activity?", Enzyme and Microbial Technology, vol. 27, 2000, pp. 108-113.
Turner, Progress in Industrial Microbiology, Martinelli and Kinghorn (eds.), Elsevier, Amsterdam, 1994, 29:641-666.
Uppenberg, Jonas, et al., "Crystallographic and Molecular-Modeling Studies of Lipase B from Candida antarctia Reveal a Stereospecificity Pocket for Secondary alcohols", Biochemistry, 1995, vol. 34, pp. 16838-16851.
Uppenberg, Jonas, et al., "The Sequence, crystal structure determination and refinement of two crystal forms of lipase B from *Candida antarctica*", Structure 1994, vol. 2, No. 4.
Upton C et al TIBS Trends in Biochemical Sciences, Elsevier Publication (1995), vol. 20, pp. 178-179.
Uusitalo et al. (1991) J Biotechnol. 17(1), 35-49.
Uwajima T et al, Agricultural and Biological Chemistry, 43(12), pp. 2633-2634, 1979.
Uwajima T et al, Agricultural and Biological Chemistry, 44(9), pp. 2039-2045, 1980.
Uwajima T et al, Methods in Enzymology, 89(41), pp. 243-248.
Vaidehi, et al.; "Lipase Activity of Some Fungi Isolated from Groundnut"; Current Science (1984); vol. 53(23); p. 1253.
van Binsbergen, Jan, et al., "Substitution of Phe-5 and Ile-9, Amino Acids Involved in the Active Site of Phospholipase A2 (PLA), and Chemical Modification of Enzymatically Generated (LYS-6)-PLA.", Proceedings of the 20th European Peptide Symposium, Sep. 4-9, 1988, University of Tubingen.
van Gemeren, I.A., et al., "Expression and Secretion of Defined Cutinase Variants by *Aspergillus awamori*" Applied and Environmental Microbiology, vol. 64, No. 8, pp. 2794-2799, Aug. 1998.
van Kampen, M.D., et al., "The phospholipase activity of *Staphylococcus hyicus* lipase strongly depends on a single Ser to Val mutation", Chemistry and Physics of Lipids, vol. 93, 1998, pp. 39-45.
van Oort, Maarten G et al, Biochemistry 1989 9278-9285.
Vaysse et al J. of Biotechnology 53 (1997) 41-46.
Villenueva, Inform, vol. 8, No. 6, Jun. 1997.
Vujaklija, Dusica, et al., "A novel streptomycete lipase: cloning, sequencing and high-level expression of the Streptomyces rimosus GDS (L)-lipase gene", Arch. Microbiol, vol. 178, pp. 124-130, 2002.
Wahnelt S.V., Meusel D, & Tülsner M, (1991) Zur kenntnis des diglyceride influsses auf das kristallisationsverhalten von Fetten, in Fat Science Technology 4:117-121.
Waninge, Rianne, et al., "Milk membrane lipid vesicle structures studied with Cryo-TEM", Colloids and Surfaces B: Biointerfaces 31 (2003), pp. 257-264.
Warmuth et al, 1992, Bio Forum 9, 282-283.
Watanabe et al. Bio sci Biochem 63(5) 820-826, 1999.
Watanabe, Yasuo et al., "Cloning and sequencing of phospholipase B gene from the yeast *Torulaspora delbrueckii*", FEMS Microbiology Letters, vol. 124, 1994, pp. 29-34.
Webb EC, Enzyme Nomenclature, 1992, p. 310.
Weber et al. J Agric Food Chem 1985, 33, 1093-1096.
Wen-Chen Suen et al., "Improved activity and thermostability of *Candida antarctica* lipase B by DNA family shuffling", Protein Engineering, Design & Selection, vol. 17, No. 2, pp. 133-140, 2004.
West S.; "Olive and Other Edible Oils"; Industrial Enzymology (1996); pp. 295-299.
Whitehead, Michael, et al., "Transformation of a nitrate reductase deficient mutant of *Penicillium chrysogenum* with the corresponding *Aspergillus niger* and *A. nidulans* niaD genes", Mol Gen Genet, 216: 408-411, 1989.
Wilhelm et al., "A Novel Lipolytic Enzyme Located in the Outer Membrane of *Pseudomonas aeruginosa*", Journal of Bacteriology, vol. 181, No. 22, Nov. 1999, pp. 6977-6986.
Winnacker, Chapter 11, pp. 424-431 in From genes to clones: introduction to gene technology, VCH (1987).
Winnacker, E. "Chapter 11: Identification of Recombinant DNA" in *From Genes to Clones: Introduction to Gene Technology*, 1987 John Wiley & Sons.
Winther, Ole, et al., "Teaching computers to fold proteins", Physical Review, vol. 70, No. 030903, 2004.
Withers-Martinez, Chrislaine, et al., "A pancreatic lipase with a phospholipase A1 activity: crystal structure of a chimeric pancreatic lipase-related protein 2 from guinea pig", Structure, 1996, vol. 4, No. 11.
Witt, Wolfgang et al., "Secretion of Phospholipase B From *Saccharomyces cerevisiae*", Biochimica et Biophysica Acta, vol. 795, 1984, pp. 117-124.
Wood et al., Eds., "Biomass, Part B, Lignin, Pectin, and Chitin", Methods in Enzymology (1988) vol. 161, Academic Press, San Diego.
Xu, Jun, et al., "Intron requirement for AFP gene expression in *Trichoderma viride*", Microbiology, 2003, vol. 149, pp. 3093-3097.
Yamaguchi et al, 1991, Gene 103:61-67.
Yamane et al., "High-Yield Diacylglycerol Formation by Solid-Phase Enzymatic Glycerolysis of Hydrogenated Beef Tallow", JAOCS, vol. 71, No. 3, Mar. 1994.
Yamano Y, Surface activity of lysophosphatidyl choline from soybean.
Yamauchi, Asao et al., "Evolvability of random polypetides through functional selection within a small library", Protein Engineering, vol. 15, No. 7, pp. 619-626, 2002.
Yang, Baokang, et al., "Control of Lipase-Mediated Glycerolysis Reactions with Butteroil in Dual Liquid Phase Media Devoid of Organic Solvent", J. Agric. Food Chem., 1993, vol. 41, pp. 1905-1909.
Zaks, Aleksey, et al., "Enzyme-catalyzed processes in organic solvents", Proc. Natl. Acad. Sci. USA, vol. 82, pp. 3192-3196, May 1985.
Zaks, Aleksey, et al., "The Effect of Water on Enzyme Action in Organic Media", The Journal of Biological Chemistry, vol. 263, No. 17, Issue of Jun. 15, pp. 8017-8021, 1988.
Zangenbert, Niels Honberg, et al., "A dynamic in vitro lipolysis model 1. Controlling the rate of lipolysis by continuous addition of calcium", European Journal of Pharmaceutical Sciences, vol. 14, 2001, pp. 115-122.
Zangenbert, Niels Honberg, et al., "A dynamic in vitro lipolysis model II. Evaluation of the model", European Journal of Pharmaceutical Sciences, vol. 14, 2001, pp. 237-244.
Zhang, Hong, et al., "Modification of Margarine Fats by Enzymatic Interesterification: Evaluation of a Solid-Fat-Content-Based Exponential Model with Two Groups of Oil Blends", JAOCS, vol. 81, No. 1, 2004.
Acker, L. "Die Lipide des Getreides, ihre Zusammense and inre Bedeutung", Getreide Mehl Brot (1974) 28:181-187.
Adamzcak, Marek, et al., "Application of Enzymatic Glycerolysis for Production of Monoglycerides from Waste Fats", Polish Journal of Food and Nutrition Science, Mar. 1994.
Adhikari, B., et al., "Stickiness in Foods: A Review of Mechanisms and Test Methods", International Journal of Food Properties, vol. 4, No. 1, 2001.
Agarwal et al., "Lipase Activity of Some Fungi Isolated from Groundnut", Current Science, Dec. 5, 1984, vol. 53, No. 23.

(56) References Cited

OTHER PUBLICATIONS

Aires-Barros et al (1994) Isolation and purification of lipases, Cambridge Unversity Press.
Aisaka, Kazuo et al., "Production of Lipoprotein Lipase and Lipase by *Rhizopus* japonicu", Agri. Biol. Chem., vol. 43, No. 10, pp. 2125-2129, 1979.
Akoh, Casimir C., et al., "GDSL family of serine esterases/lipases" Progress in Lipid Research, vol. 43, 2004, pp. 534-552.
Allan Svendsen et al., "Biochemical properties of cloned lipases from the Pseudomonas family", Biochimica et Biophysica Acta, vol. 1259, 1995, pp. 9-17.
Al-Obaidy, K A, Dissertation Abstracts International B (1987) vol. 47(9) 3597, order No. DA8624641, pp. 266.
Amano Enzyme Inc. (2004). Http://www.amano-enzyme.co.jp/english/productuse/oil_fat.html. Dato 21.06.04.
Amano Enzymes "Enzymes for Gastrointestinal Digestion" Oct. 1997.
Amano Enzymes, Amano Enzyme Europe Ltd, Sep. 1994.
Amin, Neelam S., et al., "Direct transformation of site-saturation libraries in *Bacillus subtilis*", BioTechniques, Dec. 2003, 35:1134-1140.
Andersson, L., et al., "Hydrolysis of galactolipids by human pancreatic lipolytic enzymes and duidenal contents", Journal of Lipid Research, 1995, vol. 36, pp. 1392-1400.
Andreas Sander, Eberhand Eilers, Andrea Heilemann, Edith von Kreis.Fett/lipid 99 (1997) Nr. 4, 115-120.
An-I Yeh et al., "Effects of Oxido-reductants on rheological properties of wheat flour dough and comparison with some characteristics of extruded noodles", Cereal Chemistry, 1999, vol. 76, No. 5, pp. 614-620.
Archer, David B., et al., "Proteolytic degradation of heterologous proteins expressed in *Aspergillus niger*", Biotechnology Letter, vol. 14, No. 5, May 1992, pp. 357-362.
Arcos J.A. et al, "Quantative Enzymatic Production of 6.O-Acylglucose Esters", Biotechnology and Bioengineering 1998 57(5).
Arpigny Jean Louis et al, "Bacterial lipolytic enzymes: Classification and properties", Biochemical Journal, vol. 343, No. 1, Oct. 1, 1999, pp. 177-183, XP002375631.
Atomi, et al.; "Microbial Lipases—from Screening to Design"; pp. 49-51.
Aug. C.A.P.A. et al. "The use of genetic engineering to obtain efficient production of porcine pancreatic phospholipase A2", Biochimica et Biophysica Acta, vol. 1089, 1991, pp. 345-351.
Aunstrup, Knud et al., "Production of Microbiol Enzymes", Microbiol Technology, vol. 1.
Ausubel, Frederick M., et al., "Short Protocols in Molecular Biology—A Compendium of Methods from Current Protocols in Molecular Biology", 1995, John Wiley & Sons, Inc.
Bachmatova, I., et al., "Lipase of Pseudomonas mendocina 3121-1 and its Substrate Specificty", Biologija, 1995.
Balcao V.M., Pavia A.L. Malcata F.X., Enzyme Microb Technhol, May 1, 1996; 18(6):392-416.
Balcao, Victor M and Malcata F. Xavier (1998), Biotechnology Advances, vol. 16, No. 2, pp. 309-341.
Ballance, D.J., et al., "Transformation of *Aspergillus nidulans* by the orotidine-5'-phosphate decarboxylase gene of neurospora crassa", Biochemical and biophysical Research Communications, vol. 112, No. 1, 1983, pp. 284-289.
Ballance, Molecular Industrial Mycology, Systems and Applications for *Filamentous fungi*, Leong and Berka (eds.), Marcel Dekker Inc, New York 1991, pp. 1-29.
Barbesgaard, Peder et al Applied Microbiology and Biotechnology (1992) 36: 569-572.
Barnes, P.J., "Lipids in Cereal Technology", Food and Science Technology, Academic Press, 1983.
Basrl, M., et al., "Amidination of Lipase with Hyrdophobic Imidoesters", JAOCS, vol. 69, No. 6, Jun. 1992.
Bateman A and Haft DH (2002) Brief Bioinform 3, 236-245.
Bateman A et al, (2002) Nucleic Acids Res. 30, 276-280.
Bekkers et al, The use of genetic engineering to obtain efficient production of porcine pancreatic phospholipase A2 by *Saccharomyces cerevisiae*, (1991) Biochim Biophys Acta 1089(3), 345-51.
Bengtsson Olivecrona Gunilla et al. Phospholipase activity of milk lipoprotein lipase, Methods in Enzymology, vol. 197, 1991.
Bentley S D et al, Complete genome sequence of the model actinomycete *Streptomyces coelicolor* A3(2), Nature vol. 417, 2002, pp. 141-147.
Berger K.G. (1990) Recent developments in palm oil. In Oleagineux 45:437-443.
Berks, Ben C., "A common export pathway for proteins binding complex redox cofactors?" Molecular Microbiology, 1996, vol. 22, pp. 393-404.
Beucage S.L. et al, (1981) Tetrahedron Letters 22, p. 1859-1869.
Bilyk, Alexander, et al., "Lipase-catalyzed triglyceride Hydrolysis in Organic Solvent", pp. 320-323, JAOCS, vol. 68, No. 5, May 1991.
Birch et al., "Evidence of Multiple Extracellular Phospholipase Activities of *Aspergillus fumigatus*", Infection and Immunity, Mar. 1996, vol. 64, No. 3, 1996.
Birgitte Hugh-Jensen et al., "Rhizomucor miehei Triglyceride Lipase is Processed and Secreted from Transformed *Aspergillus oryzae*", Lipids, vol. 24, No. 9, 1989.
Biswas, et al., "Interfacial Behavior of Wheat Puroindolines: Study of Adsorption at the Air-Water Interface from Surface Tension Measurement Using Wilhelmy Plate Method", Journal of Colloid and Interface Science, vol. 244, pp. 245-253, 2001.
Bjorkling, F., et al., "Lipase Catalyzed Organic Synthesis", S. Servie (ed.), Microbial Reagents in Organic Synthesis, pp. 249-260, 1992.
Bjorkling, Frederik, et al., "Lipase Catalyzed Synthesis of Perozycarboxylic Acids and Lipase Mediated Oxidations", Tetrahedron, vol. 48, No. 22, pp. 4587-4592, 1992.
Bjorkling, Frederik, et al., "Lipase -mediated Formation of Peroxycarboxylic acids used in Catalytic Epoxidation of Alkenes", J. Chem. Soc., Chemical Communications, Issue 19, 1990.
Bjurlin et al. Identification of carboxylesterase activities of commercial triacylglycerol hydrolase (lipase) preparations, Eur. J. Lipid Sci. Technol. 104 (2002) 143-155.
Blain JA et al, The Nature of Mycelial Lipolytic enzymes in *Filamentous fungi*, Fems Microbiol. Lett., 1978, vol. 3, 85-87.
Blecker et al, Improved emulsifying and foaming of whey proteins after enzymic fat hydrolysis, (1997) J Food Science, vol. 62, No. 1.
Blumenthal, Cynthia Z., "Production of toxic metabolites in *Aspergillus niger, Aspergillus oryzae*, and *Trichoderma reesei*: justification of mycotoxin testing in food grade enzyme preparations derived from the three fungi", Regulatory Toxicology and Pharmacology, vol. 39, 2004, p. 214-228.
Boel, Esper, et al.; "Rhizomucor miehei Triglyceride Lipase is Synthesized as a Precursor"; Novo Research Institute; vol. 23; No. 7; Jul. 1988.
Bornscheuer U T et al, Trends in Biotechnology, Elsevier Publications, Cambridge GB, vol. 20, No. 10, Oct. 1, 2002, pp. 433-437.
Bornscheuer, Uwe T., Lipase-catalyzed syntheses of monoacylglycerols, Enzyme and Microbio Technology, vol. 17, pp. 578-586, 1995.
Brady, Leo, et al., "A serine protease triad forms the catalytic centre of a triacylglycerol lipase", Nature, vol. 343, 1990.
Brockerhoff, Hans, et al., "Lipolytic Enzymes", Academic Press, 1974.
Brumlik, Michael J., et al., "Identification of the Catalytic Triad of the Lipase/Acyltransferase from *Aeromonas hydrophila*", Journal of Bacteriology, Apr. 1996, vol. 178, No. 7, pp. 2060-2064.
Brzozowski, A.M., et al., "A model for interfacial activation in lipases from the structure of a fungal lipase-inhibitor comples", Nature, vol. 351, 1991.
Buckley J. Thomas et al, Journal of Biological Chemistry, vol. 257, No. 6, pp. 3320-3325, 1982.
Buckley, Biochemistry 1983, 22, 5490-5493.
Bulkacz J et al, Biochim. Biophys. Acta (1981) vol. 664, pp. 148-155.
Bulletin of the IDF 294: 1994.
Burdge, Graham C., et al., "A method for separation of phosphatidylcholine, triacylglycerol, non-esterified fatty acids and

(56) References Cited

OTHER PUBLICATIONS cholesterol esters from plasma by solid-phase extraction", British Journal of Nutrition, 2000, vol. 84, pp. 281-787.
Butcher, Bronwyn G., et al., Microbiology, 2002, vol. 148, pp. 3983-3992.
Buxton et al, Gene, 1985, 37:207-214.
Carriere et al, "Pancreatic Lipase Structure- Function Relationships by Domain Exchange", American Chemical Society-Biochemistry (1997), 36, pp. 239-248.
Carriére, Frédéric, et al., "Structural basis for the substrate selectivity of pancreatic lipases and some related proteins", Biochemica et Biophysica Acta, vol. 1376, pp. 417-432, 1998.
Caruthers MH et at (1980) Nuc Acids Res Symp Ser 215-23.
Casimir C A et al Progress in Lipid Research, 2004, pp. 534-552.
Castello, Phillippe, et al., "Effect of exogenous lipase on dough lipids during mixing of wheat flours", Cereal Chemistry, 1998, vol. 75, No. 5, pp. 595-601.
Castello, Phillippe, et al., "Effects of mixing conditions and wheat flour dough composition on lipid hydrolysis and oxidation levels in the presence of exogenous lipase", Cereal Chemistry, 1999, vol. 76, No. 4. pp. 476-482.
Chakravarti DN et al, Biol. Abstracts, 1981, vol. 72, abstract No. 012592.
Cheng Cheng et al., "Transformation of *Trichoderma viride* using the Neurospora crassa pyr4 gene and its use in the expression of a Taka-amylase a gene from *Aspergillus oryzae*", Curr. Genet., 18: 453-456, 1990.
Christensen et al, "A new and simple method to immobilise lipases by means of granulation", 1998 Nachwachsende Rohstoff 10, 98-105.
Christie, William et al., "New Procedures for Rapid Screening of Leaf Lipid Components from *Arabidopsis*", Phytochemical Analysis, vol. 9, pp. 53-57, 1998.
Christophersen, Claus, et al., "Enzymatic Characterisation of Novamyl a Thermostable α-Amylase", Starch/Sturke, vol. 50, 1998.
Chung O K et al, "Defatted and Reconstituted wheat flours. VI. Response to shortening addition and Lipid Removal in Flours that vary in Bread-making Quality" Cereal Chemistry (1980), vol. 57(2), p. 111-117.
Chung OK et al, "Recent Research on Wheat Lipids" Bakers Digest Oct. 1981.
Ciuffreda, Pierangela, et al., "Spectrophotometric Assay of Lipase Activity: A New 40nitrophenyl Ester of a Dialkylglycerol Suitable as a Chromogenic Substrate of *Pseudomonas cepacia* Lipase", Biocatalysis and Biotransformation, vol. 21, No. 3, pp. 123-127, 2003.
Claesson et al., "Techniques for measuring surface forces", Advances in Colloid and Interface Science, vol. 67, 1996, pp. 119-183.
Clausen, Kim, "Enzymatic oil-degumming by a novel microbial phospholipase", European Journal of Lipid Science and Technology, vol. 103, 2001, pp. 333-340.
Clausen, Kim, "New enzyme for degumming", Oils and Fats International, vol. 17, No. 4, Jun. 2001, pp. 24-25.
Collar C, et al, "Lipid binding fresh and stored formulated wheat breads. Relationships with dough and bread technological performance", Lab de Cereales Inst de Agroquimica y Tec de Alimentos, CSIC, Food Science and Technology International 2001, vol. 7(6), p. 501-510.
Colombo, Diego, et al., "Optically Pure 1-0- and 3-0-β-D-Glucosylk- and Galactosyl-sn-glycerols through Lipase-catalyzed Transformations", Tetrahedron Letters, vol. 36, No. 27, pp. 2865-4868, 1995.
Conference May 6-8, 1999 in Santorini, Greece—Lipases & Lipids Structure, Function and Biotechnological Applications—Slides presented by Charlotte Poulsen.
Cordle et al, "The hydrophobic surface of colipase influences lipase activity at an oil-water interface", Journal of Lipid Research, vol. 39 (1998), 1759-1767.
Coteron, A., et al., "Reactions of Olive Oil and Glycerol over Immobilized Lipases", JAOCS, vol. 75, No. 5, 1998.
Council Directive of Dec. 21, 1988 (89/107/EEC).
Council Regulation (EC) No. 2991/94 5/12/94 Official Journal of the European Communities, Sep. 12, 1994, No. L316/2-7.
Creveld, Lucia D, et al., "Identification of Functional and Unfolding Motions of Cutinase as Obtained from Molecular Dynamics Computer Simulations", Proteins: Structure, Function, and Genetics, 33:253-264, 1998.
Cromie, Susan. Psychrotrophs and their Enzyme residues in cheese milk, The Australian Journal of Dairy Technology, vol. 47, Nov. 1992.
Cui et al., "Purification and characterization of an intracellular carboxylesterase from *Arthrobacter* viscosus NRRL B-1973", Enzyme and Microbial Technology, vol. 24, pp. 200-208, 1999.
Daboussi et al, Heterologous expression of the *Aspergillus nidulans* regulatory gene nirA in *Fusarium* oxysporum, (1991) Gene 109(1), 155-60.
Daboussi et al., "Transformation of seven species of *Filamentous fungi* using the nitrate reductase gene of *Aspergillus nidulans*", Curr. Genet., 15:453-456, 1989.
Daftary, R.D., et al., "Functional Bread-Making Properties of Wheat Flour Lipids", Food Technology, vol. 22, No. 237, Mar. 1968-1979.
Dahlquist, Anders, et al., "Phospholipid: diacylglycerol acyltransferase: An enzyme that catalyzes the acyl-CoA-independent formation of triacylglycerol in yeast and plants", PNAS, vol. 97, No. 12, pp. 6487-6492, 2000.
Dalrymple, Brian D., et al., "Three Neocallimastic patriciarum esterases associated with the degradation of complex polysaccharides are members of a new family of hydrolases", Microbiology, vol. 142, pp. 2605-2614, 1997.
Danisco, "Unique Chance for Better Bread" *Direct, A Newsletter from Danisco Ingredients* (1996).
Darnell et al., Eds., "Synthetic Peptide and Nucleotide Sequences: Their Use in Isolating and Identifying Genes", in *Molecular Cell Biology*, Chapter 6, Manipulating Macromolecules, 1990, Scientific American Books, Baltimore.
Database accession No. P10480—& Database UniProt 'Online!, Jul. 1, 1989.
Database accession No. Q44268—& Database UniProt 'Online! Nov. 1, 1996.
Database accession No. Q9F7Y6 Database UniProt 'Online!, Mar. 1, 2001.
Database FSTA International Food Information Service (IFIS), Frankfurt/Main, De Nicolas J:"Action of oxidoreductases in breadmaking. Maturation of soft wheat flours and kneading of doughs." XP002077286 see abstract & Annales De Technologie Agricole, vol. 28, No. 4, 1979, pp. 445-468.
Database FSTA International Food Information Service (IFIS), Frankfurt/Main, De Qi Si J: "New enzymes for the baking industry" XP002077284 see abstract & Food Tech Europe vol. 3, No. 1, 1996, pp. 60-64, Novo Nordisk Ferment Ltd.
Database FSTA International Food Information Service (IFIS), Frankfurt/Main, De Weipert D:"Rheologie von Roggenteigen. II. Der einfluss der enzyme unterschiedlicher spezifitat auf das rheologische verhalten des teiges." XP002077285 see abstract & Getreide, Mehl Und Brot, vol. 26, No. 10, 1972, pp. 275-280.
Database Uniprotkb Jun. 1, 2003, S. Omura et al: "putative secreted hydrolase from streptomyces avermitilis" XP002376340 retrieved from EBI, Hinxton, UK Database accession No. Q828T4 abstract.
Database Uniprotkb May 1, 2000, S.D. Bentley et al: "Putative Secreted Hydrolase from *Streptomyces coelicolor*" XP002376339 retrieved from EBI, Hinxton, UK Database accession No. Q9S2A5 abstract.
Davies, Progress in Industrial Microbiology, Martinelli and Kinghorn (eds.), Elsevier, Amsterdam 1994, 29:525-560.
De Haas GH et al, "Purification and Properties of Phospholipase A from Porcine Pancreas" Biochim. Biophys. ACTA, 1968, vol. 139, pp. 103-117.
Delcros, Jean-Francois, et al., "Effect of mixing conditions on the behavior of lipoxygenase, peroxidase, and catalase in wheat flour doughs", Cereal Chemistry, 1998, vol. 75, No. 1, pp. 85-93.
Dellaporta, et al.; "A Plant DNA Minipreparation Version II"; Plant Molecular Biology Reporter(1983); vol. 1(4); pp. 19-21.

(56) References Cited

OTHER PUBLICATIONS

Derewenda et al, "The crystal and molecular structure of the Rhizomuxor miehei Triacylglyceride Lipase at 1.9 ÅResolution", J. Mol. Biol. 1992, 227:818-839.
Derewenda, Urszula, et al., "Catalysis at the Interface: The Anatomy of a Conformational Change in a Triglyceride Lipase", Biochemistry, vol. 31, pp. 1532-1541, 1992.
Direct, A Newsletter from Danisco Ingredients, Sep. 1996.
Directive 2000/36/EC. Http://europa.eu.int/scadplus/leg/en/Ivb/121122b.htm. Dato: 16.06.04.
Drost-Lustenberger, Cornelia, et al., "Lipopan F BG-application and mechanism of a new lipase for bread baking", Cereal Food, 2003.
Drost-Lustenberger, Cornelia, et al., "Lipopan F BG-unlocking the natural strengthening potential in dough", Cereal Food, 2004.
Duan, Rui Dong, Fat Digestion and Absorption (2000), p. 25-46, publisher AOCS Press, Champaign III CODEN 69ACBA Conference; general review written in English.
Dubreil, Laurence, et al., "Localization of Puroinoline-a and Lipids in Bread Dough Using Confocal Scanning Laser Microscopy", J. Agric. Food Chem., 2002, vol. 50, pp. 6078-6085.
Ducancel, Frederic, et al., "Complete amino acid sequence of a PLA2 from the tiger snake *Notechis* sculatus scutatus as deduced from a complementary DNA", Nucleic Acids Research, vol. 16, No. 18, 1988.
Dugi KA et al, "Human hepatic and lipoprotein lipase: the loop covering the catalytic site mediates lipase substrate specificity", Journal of Biological Chemistry (1995), vol. 270, pp. 25, 396-pp. 25, 401.
Dutilh & Groger, "Improvement of Product Attributes of Mayonnaise by Enzymic Hydrolysis of Egg Yolk with Phospholipase A2", 1981 J. Sci. Food Agric. 32, 451-458.
Eddine et al, "Cloning and expression analysis of NhL1, a gene encoding an extracellular lipase from the fungal pea pathogen Nextria haematococca MP VI (*Fusarium solani* f. sp. pisi) that is expressed in planta", Mol. Genet. Genomics (2001) 265: 215-224.
EFEMA Index of Food Emulsifiers Jan. 2004, 4th Edition.
Ellaiah et al., "Production of lipase by immobilized cells of *Aspergillus niger*", Process Biochemistry, vol. 39, 2004, pp. 525-528.
Elyk, Alexander, et al., "Lipase-Catalyzed ", JAOCS, vol. 08, No. 5, May 1991, pp. 320-323.
Engelhorn and Raab, "Rapid Electroblotting of Small DNA Fragments from Polyacrylamide Gels", Biotechniques (1991) 11(5):594-6.
Engelhorn et al., "Rapid Electroblotting of Small DNA Fragments from Polyacrylamide Gels"; Biotechniques(1991); vol. 11(5); pp. 594-596.
Enzymes in food processing (3rd Ed.), Academic press 1993.
EPO, Mobay Chemical Corporation—Decision of the Technical Board of Appeal 3.3.1 dated Jul. 1, 1982, *Official Journal EPO*, Oct. 1982, pp. 394-402.
Ettinger, William F. et al., "Structure of Cutinase Gene, cDNA, and the Derived Amino Acid Sequence from Phytopathogenic Fungi", Biochemistry, vol. 26, pp. 7883-7892, 1987.
Euromonitor International, "The World Market for Dairy Products—Introduction, Executive Summary, Operating Environment, World Market Overview, Key Trends and Developments" in *Euromonitor, Strategy 2000*, Feb. 2001.
European Parliament and Council Directive No. 95/2/EC of Feb. 20, 1995 on food additives other than colours and sweeteners.
European Parliament and Council Directive No. 98/72/EC of Oct. 15, 1998 amending Directive 95/2/EC on food additives other than colours and sweeteners.
Eurpean Journal of Biochemistry, vol. 166, 1987, Published by Springer International on behalf of the Federation of European Biochemical Societies.
Ezra, David, et al., "Coronamycins, peptide antibiotics produced by a verticillate *Streptomyces* sp. (MSU-2110) endophytic on Monstera sp.", Microbiology, 2004, vol. 150, p. 785-793.
Fauvel, et al.; "Purification of Two Lipases With High Phospholipase A, Activity from Guinea-Pig Pancreas"; Biochimica et Biophysica Acta(1981); vol. 663; pp. 446-456.

Fernandez-Garcia et al., "The use of lipolytic and proteolytic enzymees in the manufacture of manchego type cheese from ovine and bovine milk", 1994 J. Dairy Sci. 77: 2139-2149.
Fernandez-Lafuente, Roberto, et al., The coimmobilization of D-amino acid oxidase and catalase enables the quantitative transformation of D-amino acids (D-phenylalanine) into α-keto acids (phenylpyruvic acid), Enzyme and Microbial Technology, vol. 23, pp. 28-33, 1998.
Ferrer et al, 2000, J. Chem. Technol. Biotechnol. 75, 569-576.
Finizym Technical Information, Novo Enzymes, 1981.
Frødevarenubusteriet (2003). Bekendtgørelse om indhold af transfedtsyrer I olier og fedtstoffer. Bekendtgørelse nr. 160 af Nov. 3, 2003.
Forman, Todd, "Enzymes Used in Bread Baking: An Application Update", Technical Bulletin, vol. XXVI, Issue 10, Oct. 2004.
Fox, et al.; "Isolation and some Properties of Extracellular Heat-Stable Lipases: from *Pseudomonas fluorescens* Strain AFT 36"; Journal of Dairy Research (1988); vol. 50; pp. 77-89.
Frenken N. et at (1992) Appl. Envir. Microbiol. 58 3787-3791.
Frohman, et al.;"Rapid Production of Full-Length cDNAs from Rare transcripts: Amplification using a single gene-specific oligonucleotide primer"; Proc. Natl. Acad. Sci. USA (1988); vol. 85; pp. 8998-9002.
Fugman, Douglas A et at Biochemica et Biophysica acia 795 (1984) 191-195.
Galliard T and Dennis S (1974) Phytochemistry vol. 13, pp. 1731-1735.
Galliard, "The Enzymic Breakdown of Lipids in Potato Tuber by Phospholipid- And Galactolipid-Acyl Hydrolase Activities and by Lipoxygenase", Phytochemistry, 1970, vol. 9, pp. 1725-1734.
Gan, Z. et al., "Rapid Communication-Antisera agains: Wheat Diacylgalactosylglycerol (MGDG) and Diacyldigalactosylglycerol (DGDG)", Journal of Cereal Science, vol. 18, pp. 207-210, 1993.
Ganghro AB & Dahot MU, Sci Int. (Lahore), 1992, vol. 4, pp. 169-172.
Gemel, Joanna et al., "Comparison of galactolipase activity and free fatty acid levels in chloroplasts of chill-sensitive and chill resistant plants", European Journal of Biochemistry, vol. 166, 1987.
Gilbert, E. Jane, et al., "Purification and properties of extracellular lipase from Pseudomonal aeruginosa EF2", Journal of General Microbiology, 1991, vol. 137, pp. 2223-2229.
Gillian, B., Turgeon et al., "Cochliobolus heterostrophus using the *Aspergillus nidulans* amdS gene", Mol Gen Genet, 201: 450-453, 1985.
Goodey et al, Yeast Biotechnology, Berry et at (eds.), Allen and Unwin, London 1987, pp. 401-429.
Graille J, Lipid Technology, vol. 5, No. 1, 1993, pp. 11-16.
GRAS Notification dated Apr. 11, 2001 by Novozymes for Lecitase$^R$ and Lipopan T™ F.
Greenough et al (1996) Food Chem Toxicology 34:161-166 and PubMed abstract in respect thereof.
Greenough R J et al, Food and Chemical Toxicology, vol. 34(2), 1996, pp. 161-66.
Haas and Berka, 1991, Gene, 109:107-113.
Haas, et al., "Enzymatic Phosphatidylcholine Hydrolysis in Organic Solvents: An Examination of Selected Commercially Available Lipases", JAOCS, vol. 71, No. 5, May 1994, pp. 483-490.
Haas, et al.; "Lipases of the Genera *Rhizopus* and *Rhizomucor*. Versatile Catalysts in Nature and the Laboratory"; Food Biotechnology Micro-organisims (1995); pp. 549-588.
Haggag H F et al. Egypt J Food Sci vol. 22, No. 1 pp. 99-107 (1994).
Hansen, Chr., Danisco and Novozymes, Apr. 3, 2002, Food Ingredients day, R&D—the main ingredients for growth.
Hare, et al.; "Comparative Study of Comercially Available Lipases in Hydrolysis Reaction of Phosphatidylcholine"; JAOCS (1997); vol. 74; No. 9, pp. 1129-1132.
Hawker, Kim L., et al., "Heterologous expression and regulation of the Neurospora crassa nit-4 pathway-specific regulartory gene for nitrate assimilation in *Aspergillus nidulans*", Gene., vol. 100, pp. 237-240, 1991.
Helmsing, "Purification and Properties of Galactolipase", Biochim., Biophys., Acta, vol. 178, pp. 519-533, 1969.

(56) References Cited

OTHER PUBLICATIONS

Henderson, H.E., et al., "Structure-function relationships of lipoprotein lipase: mutation analysis and mutagenesis of the loop region", Journal of Lipid Research, vol. 34, 1993, pp. 1593-1602.
Henke, Erik, et al., "Activity of Lipases and Esterases towards Tertiary Alcohols: Insights into Structure-Function Relationships", Angew. Chem. Int. Ed., 2002, vol. 41, No. 17.
Hernquist L & Anjou K (1993) Diglycerides as a stabilizer of the β'-crystal form in margarines and fats, in Fette Seifen Anstrichmittel 2:64-66.
Hernquist L. Herslof B. Larsson K & Podlaha O. (1981) Polymorphism of rapeseed oil with low content of erucic acid and possibilities to stabilize the β'-crystal form in fats, in Journal of Science and Food Agriculture 32:1197-1202.
Hilton S et al, Biochemistry vol. 29, No. 38, 1990, pp. 9072-9078.
Hilton S, Buckley JT, J Biol Chem. Jan 15, 1991; 266(2): 997-1000.
Hirayama .O et al, Biochim Biophys Acta. 1975, vol. 384(1), p. 127-37.
Hjorth, Annegrethe, et al., "A Structural Domain (the lid) Found in Pancreatic Lipases is Absent in the Guinea Pic (Phospho) lipase", Biochemistry, vol. 32, pp. 4702-4704, 1993.
Höfelmann et al, J. Food Sci., 1985, 50:1721-1731.
Holmquist et al., "Lipases from *Rhizomucor miehei* and Humicola lanuginosa: Modification of the Lid covering the active site alters enantioselectivity", Journal of Protein Chemistry, vol. 12, No. 6, 1993.
Holmquist et al., "Probing a Functional Role of Glu87 and Trp89 in the Lid of Humicola lanuginosa Lipase through Transesterification Reactions in Organic Solvent", Journal of Protein Chemistry, 1995, vol. 14, No. 4, pp. 217-224.
Holmquist et al., "Trp89 in the Lid of Humicola lanuginosa Lipase is Important for Efficient Hydrolysis of Tributyrin", Lipids, vol. 29, No. 9, 1994.
Horn T et al, (1980) Nuc Acids Res Symp Ser 225-232.
Hoshino, et al.; "Calcium Ion Regulates the Release of Lipase of *Fusarium oxysporum*"; J. Biochem (1991); vol. 110; pp. 457-461.
Hoshino, et al.; "Purification and Some Characteristics of Extracellular Lipase from *Fusarium oxysporumf. sp. lini*"; Biosci. Biotech. Biochem (1992); pp. 660-664.
Hoshino, Tamotsu, et al., "Purfication and Some Characteristics of Extracellular Lipase from *Fusarium oxysporum*", Biosci. Biotech. Biochem., vol. 56, No. 4, pp. 660-664, 1992.
Hossen, Monjur and Hernandez, Ernesto, Lipids, vol. 39, Aug. 2004, pp. 777-782.
Hou Ching T, Journal of Industrial Microbiology, vol. 13, No. 4, 1994, pp. 242-248.
Hübner et al., "Interactions at the lipid-water interface", Chemistry and physics of Lipids, vol. 96, 1998, pp. 99-123.
Hugh-Jensen, Birgitte, et al., "Rhizomucor miehei Triglyceride Lipase is Processed and Secreted from Transformed *Aspergillus oryzae*", Lipids, vol. 24, No. 9, pp. 1989.
Icard-Verniere, Christele, et al., "Effects of mixing conditions on pasta dough development on biochemical changes", Cereal Chemistry, 1999, vol. 76, No. 4, pp. 558-565.
Igrejas, Gilberto, et al., "Genetic and Environmental Effects on Puroindoline-a and Puroindoline-b Content and their Relationship to Technological Properties in French Bread Wheats", Journal of Cereal Science, vol. 34, 2001, pp. 37-47.
Ikeda H et al, Nature Biotech, vol. 21, 2003, p. 526-531.
Industrial enzymology (2nd Ed.), The Macmillan press 1996.
Ishihara et at Biochimica et Biophysica Acta 388 (1975) 413-422.
Isobe and Nokihara, Febs. Lett., 1993, 320:101-106.
Isobe K et al, Journal of Molecular Catalysis B: Enzymatic 1 (1995), pp. 37-43.
Iwai and Tsujisaka (in Lipases, Borgström and Brockman (eds.), Elsevier, Amsterdam, 1984, pp. 443-468.
Izco et al. Adv Food Sci vol. 21 No. 3/4, (10-116) 1999.
Jacob, Jules S., et al., "The Effects of Galactolipid Depletion on the Structure of a Photosynthetic Membrane", The Journal of Cell Biology, vol. 103, Oct. 1986, pp. 1337-1347.

Jacobsberg B. & Oh C.H. (1976) Studies in Palm Oil Crystallisation, in Journal of the American Oil Chemist Society 53:609-616.
jan-Willem F. A. Simons et al., "Cloning, purification and characterisation of the lipase from *Staphylococcus epidermidis*", Eur. J. Biochem., vol. 253, pp. 675-683, 1998.
Jeng-yen Lin, Matthew, "Wheat Polar Lipids—A Theseis Submitted to the Graduate Faculty of the North Dakota State University of Agriculture and Applied Science", May 1972.
Jensen B et al "Effect and Activity of Lipases in Dough and Bread" Translation.
Joerger et al., "Alteration of Chain Length Selectivity of a *Rhizopus* delemar Lipase through Site-Directed Mutagenesis", Lipids, vol. 29, No. 6, 1994, pp. 377-384.
Jong et al.; "American Type Culture Collection Catalogue of Filamentous FUNGI"; Eighteenth edition (1991).
Joshi, et al.; "Specificity of Fungal Lipase in Hydrolytic Cleavage of Oil"; Acta Microbiologica Hungarica (1987); vol. 34(2); pp. 111-114.
Joshi, Sunita, et al., "Specificity of Lipase isolated from *Fusarium oxysporum*", Department of Chemistry, Indian Institute of Technology, vol. 25, No. 1 & 2, pp. 76-78.
Juffer, A.H., et al., "Adsorption of Proteins onto Charged Surfaces: A Monte Carlo Approach with Explicit Ions", Journal of Computational Chemistry, vol. 17, No. 16, pp. 1783-1803, 1996.
Jurgens, Catharina, et al., "Directed evolution of a (βα)8-barrel enzyme to catalyze related reactions in two different metabolic pathways", PNAS, Aug. 29, 2000, vol. 97, No. 18, pp. 9925-9930.
Kaniuga Z, Acta Biochim Pol. (1997), vol. 44(1), p. 21-35.
Kapur J & Sood ML, J. Parasit., 1986, vol. 72, pp. 346-347.
Kasai, Naoya, et al., "Chiral C3 epoxides and halophydrins: Their preparation and synthetic application", Journal of Molecular Catalysis B: Enzymatic, vol. 4, 1998, pp. 237-252.
Kawamura and Doi, J. of Bacteriology Oct. 1984, p. 442-444.
Keller, R.C.A., et al., "Competitive Adsorption Behaviour of Wheat Flour Components and Emulsifiers at an Air-Water Interface", Journal of Cereal Science, vol. 25, 1997, pp. 175-183.
Keum J S et al. Korean J Dairy Sci 15 (2): 103-117 1993.
Kim, Hyung Kwoun, et al., Expression and characterization of Ca2+-independent lipase from *Bacillus pumilus* B26, Biochimica et Biophysica Acta, vol. 1583, 2002, pp. 205-212.
Kim, Myo-Jeong, et al., "Thermal Inactivation Kinetics and Application of Phospho and Galactolipid-Degrading Enzymes for Evaluation of Quality Changes in Frozen Vegetables", J. Agric. Food Chem., 2001, vol. 49, pp. 2241-2248.
Kimura, Yoshiharu, et al., "Application of Immobilized Lipase to Hydrolysis of Triacylglyceride", Eur J. Appl Microbiol Biotechnol, 1983, vol. 17, p. 107-112.
King et al, Molecular and Cell Biology of Yeasts, Walton and Yarronton (eds.), Blackie, Glasgow, 1989, pp. 107-133.
Kirk, Ole, et al., "Fatty Acid Specificity in Lipase-Catalyzed Synthesis of Glucoside Esters" Biocatalysis, 1992, vol. 6, pp. 127-134.
Klein, Robert R., et al., "Altered Acyl Chain Length Specificity of *Rhizopus* delemar Lipase Through Mutagenesis and Molecular Modeling", Lipids, 1997, vol. 32, No. 2, pp. 123-130.
Klein, Robert R., et al., "Additive Effects of Acyl-Binding Site Mutations on the Fatty Acid Selectivity of *Rhizopus* delemar Lipase", JAOCS, vol. 74, No. 11, 1997.
Kocak et al, Milchwissenschaft 51(1), 1996.
Kochubei et al Role of lipids in the organization of the closest surroundings of the reaction centers(1976) Institute of Plant Physiology.
Kochubei S M et al, Biophysics (1981), vol. 26(2), p. 299-304.
Kochubei S M et al, Mol Biol (Mosk) (1975), vol. 9(2), (p. 190-13) p. 150-153.
Kochubei SM et al, Mol Biol (Mosk) (1978),(vol. 1, p. 47-54) p. 32-37.
Kolkovski et al (1991) Fish Nutrition in Practice, Biarritz (France), Jun. 24-27.
Kostal, Jan, et al., "Enhanced Arsenic Accumulation in Engineered Bacterial Cells Expressing ArsR", Applied and Environmental Microbiology, Aug. 2004, pp. 4582-4587.
Kouker, et al.; "Specific and Sensitive Plate Assay for Bacterial Lipases"; Applied and Environmental Microbiology (1987); vol. 53(1); pp. 211-213.

(56) References Cited

OTHER PUBLICATIONS

Krishna, Sajja Hari, et al., "Enantioselective transesterification of a tertiary alcohol by lipase A from *Candida antarctica*", Tetrahedron: Asymmetry, vol. 13, 2002, pp. 2693-2696.
Kristensen A.C.J. (2004) Preparation of margarine and spreads by enzyme-generated emulsifiers. Master thesis, The Royal Veterinary and Agricultural University, Frederiksberg, Copenhagen.
Krog, Cereal Foods World, The American Association of Cereal Chemists, p. 10, Jan. 1979, vol. 24, No. 1, pp. 10-11.
Krupa, Zbigniew et al., "Requirement of Galactolipids for Photosystem J Activity in Lyophilized Spinach Chloroplasts", Biochimica et Biophysica Acta, 408, pp. 26-34, 1975.
Kuipers, Oscar P., et al., "Enhanced Activity and Altered Specificity of Phospholipase A2 by Deletion of a Surface Loop", Science, vol. 244, 1989.
Kunze, Hans, et al., "On the mechanism of lysophospholipase activity of secretory phospholipase A2 (EC 3.1.1.4): deacylation of monoacylphosphoglycerides by intrinsic sn-1 specificity and Ph-dependent acyl migration in combination with sn-2 specificity", Biochimica et Biophysica Acta, vol. 1346, 1997, pp. 86-92.
Kuwabara, et al., "Purification and Some Properties of Water-soluble Phospholipase B from *Torulaspora* delbrueckii", J. Biochem., vol. 104, pp. 236-241, 1988.
Kuwabara, et al., "Purification and Some Properties of Water-soluble Phospholipase", Agric. Biol. Chem., vol. 52, No. 10, pp. 2451-2458, 1988.
Kweon et al., "Phospholipid Hydolysate and Antistaling Amylase Effects on Retrogradation of Starch in Bread", Journal of Food Science, vol. 59, No. 5, 1994.
Larsen N G et al, Journal of Cereal Science (1990), vol. 12(2), p. 155-164.
Lecointe et at Biotechnology Letters, vol. 18, No. 8 (August) pp. 869-874.
Lee, Keun Hyeung, et al., "Identification and characterization of the antimicrobial peptide corresponding to C-terminal B-sheet domain of tenecin 1, an antibacterial protein of larvae of *Tenebrio molitor*", Biochem. J., 1996, vol. 334, pp. 99-105.
Leggio, Leila Lo, et al., "The 1.62 A structure of Thermoascus aurantiacus endoglucanase: completing the structural picture of subfamilies in glycoside hydrolase family 5", FEBS Letters, vol. 523, 2002, pp. 103-108.
Leidich et al., "Cloning and Disruption of caPLB1, a Phospholipase B Gene Involved in the Pathogenicity of *Candida albicans*", The Journal of Biological Chemistry, vol. 273, No. 40, oo. 26078-26086, 1998.
Li, W., et al., "Surface properties and locations of gluten proteins and lipids revealed using confocal scanning laser microscopy in bread dough", Journal of Cereal Science, vol. 39, 2004, pp. 403-411.
Lih-ling Wang et al, J Agric. Food. Chem. (1993), 41, 1000-1005.
Lima, Vera L.M., et al., "Lecithin-cholesterol acyltransferase (LCAT) as a plasma glycoprotein: an overview", Carbohydrate Polymers, vol. 55, 2004, pp. 179-191.
Lin M J Y et al, Cereal Chemistry (1974), vol. 51(1), p. 34-45.
Lin S et al, Enzyme and Microbial Technology 18 (1996), pp. 383-387.
Lipase A "Amano" 6 Assay Note and Product Specification from Armano Pharmaceutical Co Ltd Nagoya Japan, Dec. 16, 1985.
Lipase A "Amano" 6 Assay Note and Product Specification from Armano Pharmaceutical Co Ltd Nagoya Japan, Aug. 27, 1985.
Lipase A "Amano" 6 product sheet, Apr. 1, 1999.
Lipase SP677 as a Baking Enzyme, from Novo Nordisk, Denmark, Mar. 17, 1994.
Litthauer, Derek, et al., "*Pseudomonas luteola* lipase: A new member of the 320- residue *Pseudomonas* lipase family", Enzyme and Microbial Technology, vol. 30, pp. 209-215, 2002.
Llustenberger, Cornelia, et al., "Application of Noopazyme in Asian Noodles and Non-Durum Pasta", Cereal Food, 2002-18584-01, p. 1, vol. 11.
Llustenberger, Cornelia, et al., "Enzymes in Frozen Dough and Parbaked Bread", Cereal Food, 2001-17056-01, p. 1, vol. 19.
Longhi, Sonia, et al., "Atomic Resolution (1.0 Å) Crystal Structure of *Fusarium solani* Cutinase: Stereochemical Analysis" J. Mol. Biol. vol. 268, pp. 779-799, 1997.
Lozano et al., "Over-stabilization of *Candida antarctica* lipase B by ionic liquids in ester synthesis", Biotechnology Letters, vol. 23, pp. 1529-1533, 2001.
Luzi, Paola et al, Genomics (1995), vol. 26(2), p. 407-409.
Madsen J.S. & Qvist K.B. (1997) J. Food Sci. 62, 579-582.
Mao, Cungui, et al., "Cloning and Characterization of a *Saccharomyces cerevisiae* Alkaline Ceramidase with Specificity for Dihydroceramide", The Journal of Biological Chemistry, vol. 275, No. 40, 2000, pp. 31369-31378.
Maria Teres Neves Petersen, PhD, "Total Internal Reflection Fluorescence Flow System with Electrochemical Control", TIRF-EC Flow System, Sep. 2002.
Marion D et al—Chapter 6, pp. 131-p. 167 of "Interactions The Keys to Cereal Quality" 1998 ISBN 0 913250-99-6 (ed. Hamer & Hoseney).
Marion D et al pp. 245-260 of Wheat Structure Biochemistry & Functionality (ed Schofield JP) ISBN 085404777-8 published in 2000—(It states that it is the Proceedings of Conference organised by Royal Soc of Chemistry Food Chemistry Group held on Apr. 10-12, 1995, in Reading, UK. However, it is unclear why there was such a delay).
Marsh, Derek, et al., "Derivatised lipids in membranes. Physicochemical aspexts of N-biotinyl phosphatidylethanolamines and N-acyl ethanolamines", Chemistry and Physics of Lipids, vol. 105, 2000, pp. 43-69.
Martinelle et al., "The Role of Glu87 and Trp89 in the lid of Humicola lanuginosa lipase", Protein Engineering, vol. 9, No. 6, 1996, pp. 519-524.
Martinez, Chrislaine, et al., "Engineering cysteine mutants to obtain crystallographic phases with a cutinase from *Fusarium solani* pisi", Protein Engineering, vol. 6, No. 2, pp. 157-165, 1993.
Martinez, Diego, et al., "Genome sequence of the lignocellulose degrading fungus *Phanerochaete chrysosporium* strain RP78", Nature Biology, May 2, 2004.
Mase et al., "Purification and Characterization of a new Lipase from *Fusarium* sp. TM-30", Biosci. Biotech. Biochem., vol. 59, No. 9, pp. 1771-1772, 1995.
Mason, Research Disclosure, Kenneth Mason Publications, Westbourne GB No. 390, Oct. 1996, pp. 661-662.
Masuda, Naoko, et al., "Primary structure of protein moiety of *Penicillium notatum* phospholipase B deduced from the Cdna", Eur. J. Biochem., vol. 202, pp. 783-787, 1991.
Matos AR, Lipid Catabolism: Lipid Degradation, 2000, p. 779-781.
Matos, A.R., et al., "A patatin-like protein with galactolipase activity is induced by drought stress in *Vigna unguiculata* leaves", Biochemical Society Transactions, vol. 28, part 6, 2000.
Matos, AR et al, Febs Letters, 491 (2001) p. 188-192.
Matsuda H et al, Biochim Biophys Acta, (1979), vol. 573(1), p. 155-65.
Matsuoka, et al.; Purification and properties of a Phospholipase C That has High Activity toward Sphingomyelin from *Aspergillus Saito*; Biotiechonology and Applied Biochemistry (1987); vol. 9, pp. 401-409.
Matthes et al, (1984) EMBO J. 3, p. 801-805.
McAuley, Katherine E., et al., "Structure of a feruloyl esterase from *Aspergillus niger*", Acta Crystallographica, Section D, pp. 878-887, 2004.
McCoy M G et al, Journal of Lipid Research (2002), vol. 43, pp. 921-929.
McNeill G.P. & Berger R.G. (1993) Enzymatic glycerolysis of palm oil fractions and palm oil based model mixture: Relationship between fatty acid composition and monoglyceride yield, in Food Biotechnology 7: 75-87.
McNeill, Gerald P., et al., "High-Yield Enzymatic Glycerolysis of Fats and Oils", JAOCS, vol. 68, No. 1, Jan. 1991.
McNeill, Gerald P., et al., "Selective Distribution of Saturated Fatty Acids into the Monoglyceride Fraction During Enzymatic Glycerolysis", JAOCS, vol. 69, No. 11, Nov. 1992.
Memo: From Charlotte Johanson?, "Short introduction/ status on Ferulic Acid Esterases and Acetyl Xylan Esterases", Jan. 9, 2004.

(56) References Cited

OTHER PUBLICATIONS

Meyer, V., et al., "Transcriptional regulation of the Antifungal Protein in *Aspergillus giganteus*", Mol Genet Genomics, 2002, vol. 266, pp. 747-757.
Michalski et al., "Photosynthetic apparatus in chilling-sensitive plants. VII. Comparison of the effect of galactolipase treatment of chloroplasts and cold-dark storage of leaves on photosynthetic electron flow", Biochimica et Biophysica Acta, vol. 589, pp. 84-99, 1980.
Mielgo, I., et al., "Covalent immobilisation of manganese peroxidases (MnP) from *Phanerochaete chrysosporium* and Bjerkandera sp. BOS55", Enzyme and Microbial Technology, vol. 32, 2003, pp. 769-775.
Miller, Byron S., et al., "A Comparison of Cereal, Fungal, and Bacterial Alpha-Amylases as Supplements for Breadmaking", Food Technology, Jan. 1953.
Mine Y, Food Research International, 29(1), 1996, pp. 81-84.
Ministerio da Ciencia e Tecnologia, *Diario Oficial da Uniao*, Jul. 15, 2003.
Mogensen, Jesper E., et al., "Activation, Inhibition, and Destabilization of Thermomyces lanuginosus Lipase by Detergents", Biochemistry, vol. 44, pp. 1719-1730, 2005.
Molecular Biological Methods for *Bacillus*—Chapter 3 (Ed. C.R. Harwood and S.M. Cutting) 1990, John Wiley and Sons Ltd, Chichester, UK.
Mølgaard, Anne, et al., "Rhamnogalacturonan acetylesterase elucidates the structure and function of a new family of hydrolases", Structure, vol. 9, No. 4, 2000.
Molochnaya Promyshlennost 1980 No. 11 21-25, 47—abstract from Food Sci & Tech Abs.
Monographs for Emulsifiers for Foods, EFEMA Nov. 1985 2nd Edition.
Moore, Charles M., et al., "Metal ion homeostasis in *Bacillus subtilis*", Current Opinion in Microbiology, 2005, vol. 8, pp. 188-195.
Morgan, Keith R., et al., "Stalling Ill Starch Breads: The Effect of Antistaling α-Amylase", Starch/Stärke, vol. 49, 1997, pp. 59-66.
Morgan-Jones, Gareth; "Notes on Coelomycetes.II. Concerning the *Fusicoccum* Anamorph of Botryosphaneria Ribis"; vol. Xxx, pp. 117-125; Oct.-Dec. 1987.
Morinaga et al Biotechnology (1984) 2, p. 636-639.
Morten, T. & a., Letter, Rodovre, Jul. 2004.
Mukherjee, Kumar D. et al., "Enrichment of y-linolenic acid from fungal oil by lipase-catalysed reactions", Appl. Microbiol Biotechnol (1991), vol. 35, pp. 579-584.
Murakami, Nobutoshi, et al., "Enzymatic Transformation of Glyceroglycolipids into sn-1 and sn-2 Lysoglyceroglycolipids by use of *Rhizopus arrhizus* Lipase", Tetrahedron, vol. 50, No. 7, pp. 1993-2002, 1994.
Mustranta, Annikka, et al., "Comparison of Lipases and Phosphlipases in the Hydrolysis of Phospholipids", Process Biochemistry, vol. 30, No. 5, pp. 393-401, 1995.
N. V. Nederlandsch Octrooibureau Terms and Conditions.
Nagano, et al.; "Cloning and Nucleotide Sequence of cDNA Encoding a Lipase from *Fusarium keteroporum*"; J. Biochem (1994); vol. 116; pp. 535-540.
Nagao et al, J. Biochem 124, 1124-1129, 1998.
Nagao et al, J. of Bioscience and Bioengineering vol. 89, No. 5, 446-450, 2000.
Nagao et al, J. of Molecular Catalysis B: Enzymatic 17 (2002) 125-132.
Nagao et al, JAOCS vol. 78, No. 2, 2001.
Nagao, Toshihiro et al., "Cloning and Nucleotide Sequence of CDNA Encoding a Lipase from *Fusarium heterosporum*", J. Biochem., vol. 116, pp. 535-540, 1994.
Nagao, Toshihiro et al., "Expression of Lipase cDNA from *Fusarium heterosporum* by *Saccharomyces cereviisiae*: High-Level Production and Purification", Journal of Fermentation and Bioengineering, 1996, vol. 81, No. 6, pp. 488-492.
Nagodawlthana et al., "Enzymes in Food Processing", Third Edition, 1993, Academic Press, Inc.

National Research Council (U.S.) Committee on Specifications of the Food Chemicals Codex, "Lipase Activity" in Food Chemicals Codex (1981) National Academy Press, Washington, D.C. pp. 492-493.
Needleman & Wunsch (1970), J. of Molecular Biology 48, 443-453.
Nelson and Long, Analytical Biochemistry (1989), 180, p. 147-151.
Nerland A H, Journal of Fish Diseases, vol. 19, No. 2, 1996, pp. 145-150.
Ness, Jon. E., et al., "DNA shuffling of subgenomic sequences of subtilisin" Nature Biotechnology, vol. 17, Sep. 1999.
Nestle Research Center, Brochure for "Food Colloids 2006" in Montreux, Switzerland, Apr. 23-26, 2006.
Neugnot Virginie et al, European Journal of Biochemistry, 2002, vol. 269, pp. 1734-1745.
Newport, G., et al., "KEX2 Influences *Candida albicans* Proteinase Secretion and Hyphal Formation", The Journal of Biological Chemistry, 1997, vol. 272, No. 46, pp. 28954-28961.
Nicolas, Anne, et al., "Contribution of Cutinase Serine 42 Side Chain to the Stabilization of the Oxyanion Transition State", Biochemistry, vol. 35, pp. 398-410, 1996.
Nierle W et al, Fette Seifen Anstrichmittel (1981), vol. 83(10), p. 391-395.
Nierle, W., et al., "Versuche zur Verlangerung der Haltbarkeit von Dartoffelprodukten", Chem. Mikrobiol. Technol. Lebensm., 1975, vol. 3, pp. 172-175.
Nobutoshi M et al, Tetrahedron Letters (1991), vol. 31(1), p. 1331-34.
Novozymes data dated Jul. 17, 2005 entitled "Baking performance of prior art lipases from *Humicola lanuginosa, Aspergillus tubigensis, Rhizopus delemar* and *Rhizomucor miehe*, and their activity on galactolipids in dough".
Novozymes Memo—Test of lipases for EP1193314B1, Jul. 6, 2005.
Novozymes Report 2002 Annual Report.
Novozymes, "Biowhitening—a new concept for steamed bread", *Bio Times*, Jan. 2005.
Novozymes, "Breakthrough: Less Fattening Fried Food" *Bio Times*, Jun. 2001, No. 2.
Novozymes, "Enzymes for dough strengthening", 2001.
Novozymes, "Lipopan F BG—application and mechanism of a new lipase for bread baking" (Draft) Cereal Food (2003) (Author: Drost-Lustenberger, C. et al.).
Novozymes, "Product Sheet for Lipopan F BG", *Cereal Food*, (2001).
Novozymes, "Product Sheet for Lipopan FS BG", *Cereal Food* (2002).
Novozymes, "Product Sheet for Lipopan S BG", *Cereal Food* (2002).
Novozymes, "Revolutionizing baking", *BioTimes* (2002) pp. 6-7.
Novozymes, "Strong sales for lipase that makes dough stronger" *BioTimes*, Dec. 2003.
Novozymes, "The value of innovation", *BioTimes*, Mar. 2004.
Novozymes, "The vital role of technical service in baking", *BioTimes*, Jun. 2004.
Ohm, J.B., et al., "Relationships of Free Lipids with Quality Factors in Hard Winter Wheat Flours", Cereal Chem., vol. 79, No. 2, pp. 274-278, 2002.
Ohta, S. et al., "Application of Enzymatic Modification of Phospholipids on Breadmaking", Abstract from AACC 68th Annual Meeting in Kansas City, MO, Oct. 30-Nov. 3, 1983, published in Cerial Foods World, p. 561.
Ohta, Yoshifumi, et al., "Inhibition and Inactivation of Lipase by Fat Peroxide in the Course of Batch and Continuous Glycerolyses of Fat by Lipase", Agric. Biol. Chem., vol. 53, No. 7, pp. 1885-1890, 1989.
Okiy D.A. (1977) Partial glycerides and palm oil Crystallisation, in Journal of Science and Food Agriculture 28:955.
Okiy D.A. (1978) Interaction of triglycerides and diglycerides of palm oil, in Oleagineux 33:625-628.
Okiy D.A., Wright, W.B., Berger, K.G. & Morton I.D. (1978), The physical properties of modified palm oil, in Journal of Science of Food and Agriculture 29:1061-1068.
Oluwatosin, Yemisi E., et al., "Phenotype: A Possible Role for the Kex2 Endoprotease in Vacuolar Acidification", Molecular and Cellular Biology, 1998, pp. 1534-1543.
Oluwatosin, Yemisi E., et al., "Mutations in the Yeast KEX2 Gene Cause a Vma-Like Phenotype: a Possible Role for the Kex2

(56) References Cited

OTHER PUBLICATIONS

Endoprotease in Vacuolar Acidification", Molecular and Cellular Biology, vol. 18, No. 3, pp. 1534-1543, Mar. 1998.

Oberg, Marie-Louise, "Self-assembly Structures Formed by Wheat Polar Lipids and their Interaction with Lipases", Master of Scient Thesis, Apr. 2005.

Orskov, Janne, et al., "Solubilisation of poorly water-soluble drugs during in vitro lipolysis of medium- and long-chain triacylglycerols", European Journal of Pharmaceutical Sciences, vol. 23, 2004. pp. 287-296.

Osman, Mohamed, et al., "Lipolytic activity of *Alternaria alternata* and *Fusarium oxysporum* and certain properties of their lipids", Microbios Letters, vol. 39, pp. 131-135, 1988.

O'Sullivan et al, J Plant Physiol, vol. 313, (1987) p. 393-404.

Palomo, Jose M., et al., "Enzymatic production of (3S, 4R)-(−)-4-(4'-fluorophenyl)-6-oxo-piperidin-3-carboxylic acid using a commerical preparation of lipase a from *Candida antarctica*: the role of a contaminant esterase" Tetrahedron: Asymmetry, vol. 13, 2002, pp. 2653-2659.

Palomo, Jose M., et al., "Enzymatic resolution of (±)-glycidyl butyrate in aquenous media. Strong modulation of the properties of the lipase from Rhizopus oryzae via immobilization techniques", Tetrahedron: Asymmetry, vol. 15, 2004, pp. 1157-1161.

Palomo, Jose M., et al., "Modulation of the enantioselectivity of *Candida antarctica* B lipase via conformational engineering: kinetic resolution of (±)-α-hydroxy-phenylacetic acid derivatives", Tetrahedron: Asymmetry, vol. 13, 2002, pp. 1337-1345.

Patent Abstracts of Japan vol. 016, No. 528 (C-1001), Oct. 29, 1992 & JP 04 200339 A see abstract.

Patent Abstracts of Japan vol. 095, No. 001, Feb. 28, 1995 & JP 06 296467 A see abstract.

Peelman F, et al, Protein Science Mar. 1998; 7(3): 587-99.

Penninga et al, Biochemistry (1995), 3368-3376.

Persson, Mattias, et al., "Enzymatic fatty acid exchange in digalactosyldiacylglycerol", Chemistry and Physics of Lipids, vol. 104, 2000, pp. 13-21.

Peters, G.H., et al., "Active Serine Involved in the Stabilization of the Active Site Loop in the Humicola lanuginosa Lipase", Biochemistry, 1998 vol. 17 pp. 12375-12383.

Peters, Günther H., et al., "Theoretical Investigation of the Dynamics of the Active Site Lid in *Rhizomucor miehei* Lipase", Biophysical Journal, vol. 71, 1996, pp. 119-129.

Plijter J and JHGM Mutsaers, The surface rheological properties of dough and the influence of lipase on it, Gist-brocades, Bakery Ingredients Division, Oct. 1994.

Plou et al, J. Biotechnology 92 (2002) 55-66.

Ponte J G, Cereal Chemistry (1969), vol. 46(3), p. 325-329.

Punt and van den Hondel, Meth. Enzym., 1992, 216:447-457.

Pyler, E.J., "Baking Science and Technology Third Edition", vol. 1, 1988.

Pyler, E.J., "Baking Science and Technology Third Edition", vol. II, 1988.

Queener et al. (1994) Ann N Y Acad Sci. 721, 178-93.

Rambosek and Leach, CRC Crit. Rev. Biotechnol., 1987, 6:357-393.

Rapp, Peter, et al., "Formation of extracellular lipases by filamentous fungi, yeasts, and bacteria", Enzyme Microb. Technol., 1992, vol. 14, Nov.

Rapp, Peter; "Production, regulation, and some properties of lipase activity from *Fusarium Oxysporum* f. sp. *vasinfectum*"; Enzyme and Microbial Technology(1995); vol. 17; pp. 832-838.

Reetz M.T., Jaeger K.E. Chem Phys Lipids. Jun. 1998; 93(1-2): 3-14.

Reetz Manfred T, Current Opinion in Chemical Biology, Apr. 2002, vol. 6, No. 2, pp. 145-150.

Reiser J et al. (1990) Adv Biochem Eng Biotechnol. 43, 75-102.

Richardson & Hyslop, pp. 371-476 in Food Chemistry, 1985, second edition, Owen R. Fennema (ed) Manel Dekker, Inc, New York and Basel.

Richardson and Hyslop, "Enzymes: XI—Enzymes Added to Foods During Processing" in *Food Chemistry*, Marcel Dekker, Inc., New York, NY 1985.

Arskog and Joergensen, "Baking performance of prior art lipases from *Candida cylindracea* and *Aspergillus foeditus* and their actiivty on galactolipids in dough", Novozymes Report 2005.

Arskog and Joergensen, "Baking performance of prior art lipases from *Humicola lanuginosa*, *Aspergillus tubigensis*, *Rhizopus delemar* and *Rhizomucor miehei*, and their actiivty on galactolipids in dough", Novozymes Report 2005.

FIGURE 1

SEQ ID No. 1:

GACGCTGAGGAGCGAAAGCGTGGGGAGCGAACAGGATTAGATACCCTGGTAGTCCACGCCGTAAA
CGGTGGGCACTAGGTGTGGGCAACATTCCACGTTGTCCGTGCCGCAGCTAACGCATTAAGTGCCCC
GCCTGGGGAGTACGGCCGCAAGGCTAAAACTCAAAGGAATTGACGGGGGCCCGCACAAGCGGCG
GAGCATGTGGCTTAATTCGACGCAACGCGAAGAACCTTACCAAGGCTTGACATACACCGGAAACGG
CCAGAGATGGTCGCCCCCTTGTGGTCGGTGTACAGGTGGTGCATGGCTGTCGTCAGCTCGTGTCG
TGAGATGTTCGGGTTAAGTCCCGCAACGAGCGCAACCTTATCCTGTGTTGCCAGCGGATCCCTTCG
GGGGTGCCGGGGACTCACGGGAGACTGCCGGGGTCAACTCGGA

FIGURE 2

SEQ ID NO. 2:

GACGCTGAGGAGCGAAAGCGTGGGGAGCGAACAGGATTAGATACCCTGGTAGTCCACGCCGTAAA
CGGTGGGCACTAGGTGTGGGCAACATTCCACGTTGTCCGTGCCGCAGCTAACGCATTAAGTGCCCC
GCCTGGGGAGTACGGCCGCAAGGCTAAAACTCAAAGGAATTGACGGGGGCCCGCACAAGCGGCG
GAGCATGTGGCTTAATTCGACGCAACGCGAAGAACCTTACCAAGGCTTGACATACACCGGAAACGG
CCAGAGATGGTCGCCCCCTTGTGGTCGGTGTACAGGTGGTGCATGGCTGTCGTCAGCTCGTGTCG
TGAGATGTTGGGTTAAGTCCCGCAACGAGCGCAACCCTATCCTGTGTTGCCAGCGGATCCCTTCG
GGGGTGCCGGGGACTCACGGGAGACTGCCGGGGTCAACTCGGA

FIGURE 3

SEQ ID NO. 3:

ACAGGCCGATGCACGGAACCGTACCTTTCCGCAGTGAAGCGCTCTCCCCCCATCGTTCGC
CGGGACTTCATCCGCGATTTTGGCATGAACACTTCCTTCAACGCGCGTAGCTTGCTACAA
GTGCGGCAGCAGACCCGCTCGTTGGAGGCTCAGTGAGATTGACCCGATCCCTGTCGGCCG
CATCCGTCATCGTCTTCGCCCTGCTGCTCGCGCTGCTGGGCATCAGCCCGGCCCAGGCAG
CCGGCCCGGCCTATGTGGCCCTGGGGGATTCCTATTCCTCGGGCAACGGCGCCGGAAGTT
ACATCGATTCGAGCGGTGACTGTCACCGCAGCAACAACGCGTACCCCGCCCGCTGGGCGG
CGGCCAACGCACCGTCCTCCTTCACCTTCGCGGCCTGCTCGGGAGCGGTGACCACGGATG
TGATCAACAATCAGCTGGGCGCCCTCAACGCGTCCACCGGCCTGGTGAGCATCACCATCG
GCGGCAATGACGCGGGCTTCGCGGACGCGATGACCACCTGCGTCACCAGCTCGGACAGCA
CCTGCCTCAACCGGCTGGCCACCGCCACCAACTACATCAACACCACCCTGCTCGCCCGGC
TCGACGCGGTCTACAGCCAGATCAAGGCCCGTGCCCCCAACGCCCGCGTGGTCGTCCTCG
GCTACCCGCGCATGTACCTGGCCTCGAACCCCTGGTACTGCCTGGGCCTGAGCAACACCA
AGCGCGCGGCCATCAACACCACCGCCGACACCCTCAACTCGGTGATCTCCTCCCGGGCCA
CCGCCCACGGATTCCGATTCGGCGATGTCCGCCCGACCTTCAACAACCACGAACTGTTCT
TCGGCAACGACTGGCTGCACTCACTCACCCTGCCGGTGTGGGAGTCGTACCACCCCACCA
GCACGGGCCATCAGAGCGGCTATCTGCCGGTCCTCAACGCCAACAGCTCGACCTGATCAA
CGCACGGCCGTGCCCGCCCCGCGCGTCACGCTCGGCGCGGGCGCCGCAGCGCGTTGATCA
GCCCACAGTGCCGGTGACGGTCCCACCGTCACGGTCGAGGGTGTACGTCACGGTGGCGCC
GCTCCAGAAGTGGAACGTCAGCAGGACCGTGGAGCCGTCCCTGACCTCGTCGAAGAACTC
CGGGGTCAGCGTGATCACCCCTCCCCCGTAGCCGGGGGCGAAGGCGGCGCCGAACTCCTT
GTAGGACGTCCAGTCGTGCGGCCCGGCGTTGCCACCGTCCGCGTAGACCGCTTCCATGGT
CGCCAGCCGGTCCCCGCGGAACTCGGTGGGGATGTCCGTGCCCAAGGTGGTCCCGGTGGT
GTCCGAGAGCACCGGGGGCTCGTACCGGATGATGTGCAGATCCAAAGAATT

FIGURE 4

SEQ ID NO. 4:

MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST

FIGURE 15

1. L131
2. S.avermitilis
3. T.fusca
4. Consensus

```
                        1                                                 50
1  (1)   ---------MRLTRSLSAASVIVFALLLALLGISPAQAAG------------
2  (1)   ---------MRRSRITAYVTSLLLAVGCALTGAATAQASPA-----------
3  (1)   VGSGPRAATRRRLFLGIPALVLVTALTLVLAVPTGRETLWRMWCEATQDW
4  (1)            MRRSRFLA  ALILLTLA AL GAA ARAAP 51                                                100
1  (32)  ----------------------------P-AYVA LGDSYS SGNGAGSYID
2  (33)  ----------------------------AAATGYVA LGDSYS SGVGAGSYLS
3  (51)  CLGVPVDSRGQPAEDGEFLLLSPVQAATWGNYYA LGDSYS SGDGARDYYP
4  (51)                             A A   YVA LGDSYS SG GAGSY 101                                                150
1  (53)  SSGD---CHRSNNAYPARWAAANAP---SSFTFAACSGAVTTDVIN----
2  (57)  SSGD---CKRSSKAYPYLWQAAHSP---SSFSFMACSGARTGDVLA----
3  (101) GTAVKGGCWRSANAYPELVAEAYDFA--GHLSFLACSGQRGYAMLDAIDE
4  (101) SSGD   C RSTKAYPALWAAAHA    SSFSF ACSGARTYDVLA 151                                                200
1  (93)  --NQLGALNAST--GLVSIT IGGNDAG FADAMTTCVTS------SDSTCL
2  (97)  --NQLGTLNSST--GLVSLT IGGNDAG FSDVMTTCVLQ------SDSACL
3  (149) VGSQLDWNSPHT--SLVTIG IGGNDLG FSTVLKTCMVR------VPLLDS
4  (151)     QL LNS T   LVSIT IGGNDAG FAD MTTCVL       SDSACL 201                                                250
1  (133) NRLATATNYINTTLLA-------RLDAVYSQIKARAPNARVVVLGYPRMY
2  (137) SRINTAKAYVDSTLPG-------QLDSVYTAISTKAPSAHVAVLGYPRFY
3  (191) KACTDQEDAIRKRMAKF----ETTFEELISEVRTRAPDARILVVGYPRIF
4  (201)    RIA AK YI  TLPA       RLDSVYSAI TRAP ARVVVLGYPRIY 251                                                300
1  (176) LASNPWYCLGLSNTKRAAINTTADTLNSVISSRATAH-----------GF
2  (180) KLGG-SCLAGLSETKRSAINDAADYLNSAIAKRAADH-----------GF
3  (237) PEEPTGAYYTLTASNQRWLNETIQEFNQQLAEAVAVHDEEIAASGGVGSV
4  (251)       SG   LGLS TKRAAINDAAD LNSVIAKRAADH           GF 301                                                350
1  (215) RFGDVRPTFNNHELFFGNDWLHSLTLP-----------------VWES YH
2  (218) TFGDVKSTFTGHEICSSSTWLHSLDLLN-----------------IGQS YH
3  (287) EFVDVYHALDGHEIGSDEPWVNGVQLRDLATG----------VTVDRST FH
4  (301) TFGDV  TF GHELCSA PWLHSLTLP                  V  S YH 351                                                395
1  (248) PTSTGHQSGYLPVLNANSST-----------------------
2  (252) PTAAGQSGGYLPVMNSVA-------------------------
3  (328) PNAAGHRAVGERVIEQIETGPGRPLYATFAVVAGATVDTLAGEVG
4  (351) PTA GHAAGYLPVLNSI T
```

LIPOLYTIC ENZYME: USES THEREOF IN THE FOOD INDUSTRY

REFERENCE TO RELATED APPLICATIONS

This application is a divisional of U.S. patent application Ser. No. 11/623,607 filed Jan. 16, 2007 now U.S. Pat. No. 7,666,618, which is a continuation-in-part of International Patent Application PCT/IB2005/002602 filed Jul. 18, 2005 and published as WO 2006/008653 on Jan. 26, 2006, which claims priority from Great Britain Patent Application Nos. 0513859.9 filed Jul. 7, 2005 and 0416035.4 filed Jul. 16, 2004, and from U.S. Patent Application No. 60/591,185 filed Jul. 26, 2004.

Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. Patent law; namely, that these terms are closed ended.

FIELD OF INVENTION

The present invention relates to a novel lipolytic enzyme, in particular a novel lipolytic enzyme, and nucleotide sequences encoding same. The present invention also relates to methods of production of the novel lipolytic enzyme and to uses thereof. The present invention also relates to methods and uses of a lipolytic enzyme.

TECHNICAL BACKGROUND

The beneficial use of lipolytic enzymes active on glycolipids in bread making was taught in EP 1 193 314. It was taught that the partial hydrolysis products the lyso-glycolipids were found to have very high emulsifier functionality. However, the enzymes taught in EP 1 193 314 were also found to have significant non-selective activity on triglycerides which resulted in unnecessarily high free fatty acid.

A lipolytic enzyme from *Fusarium oxysporum* having phospholipase activity has been taught in EP 0 869 167. This lipolytic enzyme has high triacylglyceride hydrolysing (lipase) activity. This enzyme is now sold by Novozymes A/S (Denmark) as Lipopan F™.

WO02/00852 discloses five lipase enzymes and their encoding polynucleotides, isolated from *Fusarium venenatum, F. sulphureum, Aspergillus berkeleyanum, F. culmorum* and *F. solani*. All five enzymes are described as having triacylglycerol hydrolysing activity, phospholipase and galactolipase activity.

Lipolytic enzyme variants, with specific amino acid substitutions and fusions, have been produced; some of which have an enhanced activity on the polar lipids compared to the wildtype parent enzymes. WO01/39602 describes such a variant, referred to as SP979, which is a fusion of the *Thermomyces lanuginosus* lipase, and the *Fusarium oxysporum* lipase described in EP 0 869 167. This variant has been found to have a significantly high ratio of activity on phospholipids and glycolipids compared to triglycerides.

In WO02/094123 it was discovered that by selecting lipolytic enzymes which were active on the polar lipids (glycolipids and phospholipids) in a dough, but substantially not active on triglycerides or 1-mono-glycerides an improved functionality could be achieved.

In co-pending PCT application number PCT/IB2005/000875, wild-type lipolytic enzymes having a higher ratio of activity on polar lipids as compared with triglycerides are taught. However, this document does not teach lipolytic enzymes from *Streptomyces, Thermobifida* or *Corynebacterium* species.

Prior to the present invention no lipolytic enzymes having activity or significant activity on glycolipids had been published from *Streptomyces* species. Likewise, no lipolytic enzymes having activity or significant activity on glycolipids had been published from *Thermobifida* species or *Corynebacterium* species. Although lipases, i.e. triacylglycerol hydrolysing enzymes, have been isolated from *Streptomyces* species (see Vujaklija et al *Arch Microbiol* (2002) 178: 124-130 for example), these enzymes have never been identified as having glycolipid hydrolysing activity.

ASPECTS OF THE INVENTION

The present invention in predicated upon the seminal finding of a lipolytic enzyme having significant galactolipid activity from the genus *Streptomyces*. In particular the lipolytic enzyme from the genus *Streptomyces* has significant galactolipid hydrolysing activity and/or significant galactolipid acyltransferase activity, particularly when used in the methods and uses according to the present invention.

In addition, the present invention in predicated upon the seminal finding that lipolytic enzymes from the genera *Thermobifida* or *Corynebacterium* have significant galactolipid activity. In particular the lipolytic enzymes from the genera *Thermobifida* or *Corynebacterium* have significant galactolipid hydrolysing activity and/or significant galactolipid acyltransferase activity, particularly when used in the methods and uses of the present invention.

In a broad aspect the present invention relates to a lipolytic enzyme capable of hydrolysing at least glycolipids and/or capable of transferring an acyl group from at least a glycolipid to one or more acyl acceptor substrates, wherein the enzyme is obtainable, preferably obtained, from *Streptomyces* species.

In a further aspect the present invention relates to a lipolytic enzyme capable of hydrolysing at least galactolipids and/or capable of transferring an acyl group from at least a galactolipid to one or more acyl acceptor substrates, wherein the enzyme is encoded by a nucleic acid selected from the group consisting of:

a) a nucleic acid comprising a nucleotide sequence shown in SEQ ID No. 3;
b) a nucleic acid which is related to the nucleotide sequence of SEQ ID No. 3 by the degeneration of the genetic code; and
c) a nucleic acid comprising a nucleotide sequence which has at least 70% identity with the nucleotide sequence shown in SEQ ID No. 3.

The present invention yet further provides a lipolytic enzyme comprising an amino acid sequence as shown in SEQ ID No. 4 or an amino acid sequence which has at least 60% identity thereto.

In another aspect the present invention provides a lipolytic enzyme capable of hydrolysing at least a galactolipid and/or capable of transferring an acyl group from at least a galactolipid to one or more acyl acceptor substrates, wherein the enzyme comprises an amino acid sequence as shown in SEQ ID No. 4 or an amino acid sequence which has at least 60% identity thereto.

In a further aspect the present invention provides a nucleic acid encoding a lipolytic enzyme comprising an amino acid sequence as shown in SEQ ID No. 4 or an amino acid sequence which has at least 60% identity therewith.

SEQ ID No. 3 is shown in FIG. 3 and SEQ ID No. 4 is shown in FIG. 4.

The present invention yet further provides a nucleic acid encoding a lipolytic enzyme, which nucleic acid is selected from the group consisting of:
a) a nucleic acid comprising a nucleotide sequence shown in SEQ ID No. 3;
b) a nucleic acid which is related to the nucleotide sequence of SEQ ID No. 3 by the degeneration of the genetic code; and
c) a nucleic acid comprising a nucleotide sequence which has at least 70% identity with the nucleotide sequence shown in SEQ ID No. 3.

The present invention yet further provides the use of a lipolytic enzyme according to the present invention in a substrate (preferably a foodstuff) for preparing a lyso-glycolipid, for example digalactosyl monoglyceride (DGMG) or monogalactosyl monoglyceride (MGMG) by treatment of a glycolipid (e.g. digalactosyl diglyceride (DGDG) or monogalactosyl diglyceride (MGDG)) with the lipolytic enzyme according to the present invention to produce the partial hydrolysis product, i.e. the lyso-glycolipid.

In a further aspect, the present invention provides the use of a lipolytic enzyme according to the present invention in a substrate (preferably a foodstuff) for preparing a lyso-phospholipid, for example lysolecithin, by treatment of a phospholipid (e.g. lecithin) with the enzyme according to the present invention to produce a partial hydrolysis product, i.e. a lyso-phospholipid.

In one broad aspect the present invention relates to a method of preparing a foodstuff the method comprising admixing a lipolytic enzyme of the present invention with one or more ingredients of the foodstuff.

Another broad aspect of the present invention relates to a method of preparing a baked product from a dough, the method comprising admixing a lipolytic enzyme of the present invention with the dough.

In a further aspect the present invention relates to a method of preparing a dairy product, the method comprising admixing a lipolytic enzyme of the present invention with one or more ingredients of the dairy product.

In another aspect the present invention relates to the use of a lipolytic enzyme of the present invention in the manufacture of a dairy product to reduce one or more of the following detrimental effects: off-odours and/or off-flavours and/or soapy taste.

In another aspect of the present invention there is provided the use of a lipolytic enzyme according to the present invention in a process of treating egg or egg-based products to produce lysophospholipids.

In another aspect of the present invention there is provided the use of a lipolytic enzyme according to the present invention in a process of treating egg or egg-based products to produce lysoglycolipids.

A further aspect of the present invention provides a process of enzymatic degumming of vegetable or edible oils, comprising treating the edible or vegetable oil with a lipolytic enzyme according to the present invention so as to hydrolyse a major part of the polar lipids (e.g. phospholipid and/or glycolipid).

In another aspect the present invention provides the use of a lipolytic enzyme according to the present invention in a process comprising treatment of a phospholipid so as to hydrolyse fatty acyl groups.

In another aspect the present invention provides the use of a lipolytic enzyme according to the present invention in a process for reducing the content of a phospholipid in an edible oil, comprising treating the oil with the lipolytic enzyme according to the present invention so as to hydrolyse a major part of the phospholipid, and separating an aqueous phase containing the hydrolysed phospholipid from the oil.

There is also provided a method of preparing a lipolytic enzyme according to the present invention, the method comprising transforming a host cell with a recombinant nucleic acid comprising a nucleotide sequence coding for the lipolytic enzyme, the host cell being capable of expressing the nucleotide sequence coding for the polypeptide of the lipolytic enzyme, cultivating the transformed host cell under conditions where the nucleic acid is expressed and harvesting the lipolytic enzyme.

In a further aspect the present invention relates to the use of a lipolytic enzyme in accordance with the present invention in the bioconversion of polar lipids (preferably glycolipids) to make high value products, such as carbohydrate esters and/or protein esters and/or protein subunit esters and/or a hydroxy acid ester.

Another aspect of the present invention relates to the use of a lipolytic enzyme in accordance with the present invention in a process of enzymatic degumming of vegetable or edible oil, comprising treating said edible or vegetable oil with said lipolytic enzyme so as to hydrolyse a major part of the polar lipids.

A further aspect of the present invention relates to the use of a lipolytic enzyme in accordance with the present invention in a process comprising treatment of a phospholipid so as to hydrolyse fatty acyl groups.

The present invention yet further relates to an immobilised lipolytic enzyme in accordance with the present invention.

Another aspect of the present invention relates to a method of preparing a lysoglycolipid comprising treating a substrate comprising a glycolipid with at least one lipolytic enzyme to produce said lysoglycolipid, wherein said lipolytic enzyme has glycolipase activity and wherein said lipolytic enzyme is obtainable from one of the following genera: *Streptomyces, Corynebacterium* and *Thermobifida*.

A further aspect of the present invention relates to a method of preparing a lysophospholipid comprising treating a substrate comprising a phospholipid with at least one lipolytic enzyme to produce said lysophospholipid, wherein said lipolytic enzyme has phospholipase activity and wherein said lipolytic enzyme is obtainable from one of the following genera: *Streptomyces, Corynebacterium* and *Thermobifida*.

Another aspect of the present invention relates to a method of enzymatic degumming of vegetable or edible oil, comprising treating said edible or vegetable oil with a lipolytic enzyme obtainable from one of the following genera: *Streptomyces, Corynebacterium* and *Thermobifida* capable of hydrolysing a major part of the polar lipids.

The present invention further relates to a method of bioconversion of polar lipids to make high value products comprising treating said polar lipids with a lipolytic enzyme obtainable from one of the following genera: *Streptomyces, Corynebacterium* and *Thermobifida* to produce said high value products, wherein said lipolytic enzyme is capable of hydrolysing said polar lipids.

Another aspect of the present invention relates to a method of preparing a foodstuff comprising admixing at least one lipolytic enzyme with one or more ingredients of a foodstuff wherein said lipolytic enzyme is capable of hydrolysing a glycolipid and/or a phospholipid present in or as at least one of said ingredients and wherein said lipolytic enzyme is obtainable from one of the following genera: *Streptomyces, Corynebacterium* and *Thermobifida*.

A further aspect of the present invention relates the use of a lipolytic enzyme in a substrate for preparing a lysophospholipid wherein said lipolytic enzyme has phospholipase activity and wherein said lipolytic enzyme is obtainable from one of the following: *Streptomyces, Corynebacterium* and *Thermobifida*.

The present invention additionally relates to the use of a lipolytic enzyme obtainable from one of the following genera: *Streptomyces, Corynebacterium* and *Thermobifida* for enzymatic degumming of vegetable or edible oil so as to hydrolyse a major part of the polar lipids.

Another aspect of the present invention relates to the use of a lipolytic enzyme obtainable from one of the following genera: *Streptomyces, Corynebacterium* and *Thermobifida* in a process comprising treatment of a phospholipid so as to hydrolyse fatty acyl groups.

A further aspect of the present invention relates to use of a lipolytic enzyme in the bioconversion of polar lipids to make high value products, wherein said lipolytic enzyme is capable of hydrolysing said polar lipids and wherein said lipolytic enzymes is obtainable from one of the following genera: *Streptomyces, Corynebacterium* and *Thermobifida*.

A further aspect of the present invention relates to the use of a lipolytic enzyme obtainable from one of the following genera: *Streptomyces, Corynebacterium* and *Thermobifida* in the preparation of a foodstuff, wherein said lipolytic enzyme is capable of hydrolysing a glycolipid and/or a phospholipid.

Aspects of the present invention are presented in the claims and in the following commentary.

Other aspects concerning the nucleotide sequences which can be used in the present invention include: a construct comprising the sequences of the present invention; a vector comprising the sequences for use in the present invention; a plasmid comprising the sequences for use in the present invention; a transformed cell comprising the sequences for use in the present invention; a transformed tissue comprising the sequences for use in the present invention; a transformed organ comprising the sequences for use in the present invention; a transformed host comprising the sequences for use in the present invention; a transformed organism comprising the sequences for use in the present invention. The present invention also encompasses methods of expressing the nucleotide sequence for use in the present invention using the same, such as expression in a host cell; including methods for transferring same.

The present invention further encompasses methods of isolating the nucleotide sequence, such as isolating from a host cell.

Other aspects concerning the amino acid sequence for use in the present invention include: a construct encoding the amino acid sequences for use in the present invention; a vector encoding the amino acid sequences for use in the present invention; a plasmid encoding the amino acid sequences for use in the present invention; a transformed cell expressing the amino acid sequences for use in the present invention; a transformed tissue expressing the amino acid sequences for use in the present invention; a transformed organ expressing the amino acid sequences for use in the present invention; a transformed host expressing the amino acid sequences for use in the present invention; a transformed organism expressing the amino acid sequences for use in the present invention. The present invention also encompasses methods of purifying the amino acid sequence for use in the present invention using the same, such as expression in a host cell; including methods of transferring same, and then purifying said sequence.

For the ease of reference, these and further aspects of the present invention are now discussed under appropriate section headings. However, the teachings under each section are not necessarily limited to each particular section.

DETAILED DISCLOSURE OF THE INVENTION

Suitably, the lipolytic enzyme for use in the methods and uses according to the present invention may be a lipolytic enzyme comprising any one of the amino acid sequences shown as SEQ ID No. 4, 5, 7, 8, 12, 14 or 16 or an amino acid sequence which has at least 70%, 75%, 80%, 85%, 90%, 95%, 96%, 97% or 98% identity therewith, or encoded by any one of the nucleotide sequences shown as SEQ ID No. 3, 6, 9, 13, 15 or 17 or a nucleotide sequence which has at least 70%, 75%, 80%, 85%, 90%, 95%, 96%, 97% or 98% identity therewith.

Preferably, the lipolytic enzyme for use in the methods and uses according to the present invention is a lipolytic enzyme capable of hydrolysing at least galactolipids and/or capable of transferring an acyl group from at least a galactolipid to one or more acyl acceptor substrates, wherein the enzyme is obtainable, preferably obtained, from *Streptomyces* species.

In one embodiment the lipolytic enzyme for use in the methods and uses according to the present invention is preferably a lipolytic enzyme capable of hydrolysing at least galactolipids and/or capable of transferring an acyl group from at least a galactolipid to one or more acyl acceptor substrates, wherein the enzyme is encoded by a nucleic acid selected from the group consisting of:
  a) a nucleic acid comprising a nucleotide sequence shown in SEQ ID No. 3;
  b) a nucleic acid which is related to the nucleotide sequence of SEQ ID No. 3 by the degeneration of the genetic code; and
  c) a nucleic acid comprising a nucleotide sequence which has at least 70% identity with the nucleotide sequence shown in SEQ ID No. 3.

In one embodiment, the lipolytic enzyme for use in the methods and uses according to the present invention is preferably a lipolytic enzyme comprising an amino acid sequence as shown in SEQ ID No. 4 or an amino acid sequence which has at least 60% identity thereto.

In another embodiment the lipolytic enzyme for use in the methods and uses according to the present invention is preferably a lipolytic enzyme capable of hydrolysing at least a galactolipid and/or capable of transferring an acyl group from at least a galactolipid to one or more acyl acceptor substrates, wherein the enzyme comprises an amino acid sequence as shown in SEQ ID No. 4 or an amino acid sequence which has at least 60% identity thereto.

Preferably, the lipolytic enzyme for use in the methods and uses according to the present invention is a lipolytic enzyme capable of hydrolysing at least galactolipids and/or capable of transferring an acyl group from at least a galactolipid to one or more acyl acceptor substrates, wherein the enzyme is obtainable, preferably obtained, from *Thermobifida* species, preferably *Thermobifida fusca*.

Preferably, the lipolytic enzyme for use in the methods and uses according to the present invention is a lipolytic enzyme capable of hydrolysing at least galactolipids and/or capable of transferring an acyl group from at least a galactolipid to one or more acyl acceptor substrates, wherein the enzyme is obtainable, preferably obtained, from *Corynebacterium* species, preferably *Corynebacterium efficiens*.

In a further embodiment the lipolytic enzyme for use in the methods and uses according to the present invention may be a lipolytic enzyme comprising any one of the amino acid sequences shown as SEQ ID No. 4, 5, 7, 8, 12, 14 or 16 or an amino acid sequence which has at least 70%, 75%, 80%, 85%, 90%, 95%, 96%, 97% or 98% identity therewith, or encoded by any one of the nucleotide sequences shown as SEQ ID No. 3, 6, 9, 13, 15 or 17 or a nucleotide sequence which has at least 70%, 75%, 80%, 85%, 90%, 95%, 96%, 97% or 98% identity therewith.

In a further embodiment the lipolytic enzyme for use in the methods and uses according to the present invention may be a lipolytic enzyme comprising any one of amino sequences shown as SEQ ID No. 5, 7, 8, 14 or 16 or an amino acid sequence which has at least 70%, 75%, 80%, 85%, 90%, 95%, 96%, 97% or 98% identity therewith for the uses described herein.

In a further embodiment the lipolytic enzyme for use in the methods and uses according to the present invention may be a lipolytic enzyme comprising any one of amino sequences shown as SEQ ID No. 5, 7 or 16 or an amino acid sequence which has at least 70%, 75%, 80%, 85%, 90%, 95%, 96%, 97% or 98% identity therewith for the uses described herein.

More preferably in one embodiment the lipolytic enzyme for use in the methods and uses according to the present invention may be a lipolytic enzyme comprising the amino acid sequence shown as SEQ ID No. 16 or an amino acid sequence which has at least 70%, 75%, 80%, 85%, 90%, 95%, 96%, 97% or 98% identity therewith.

In another embodiment the lipolytic enzyme for use in the methods and uses according to the present invention may be a lipolytic enzyme comprising the amino acid sequence shown as SEQ ID Nos. 12 or 14 or an amino acid sequence which has at least 80%, 85%, 90%, 95%, 96%, 97% or 98% identity therewith.

In another embodiment the lipolytic enzyme for use in the methods and uses according to the present invention may be a lipolytic enzyme comprising the amino acid sequence shown as SEQ ID No. 8 or an amino acid sequence which has at least 70%, 75%, 80%, 85%, 90%, 95%, 96%, 97% or 98% identity therewith.

In one embodiment the lipolytic enzyme for use in the methods and uses according to the present invention may be a lipolytic enzyme capable of hydrolysing at least galactolipids and/or capable of transferring an acyl group from at least a galactolipid to one or more acyl acceptor substrates, wherein the enzyme is encoded by a nucleic acid selected from the group consisting of:

a) a nucleic acid comprising a nucleotide sequence shown in SEQ ID No. 3;
b) a nucleic acid which is related to the nucleotide sequence of SEQ ID No. 3 by the degeneration of the genetic code; and
c) a nucleic acid comprising a nucleotide sequence which has at least 70% identity with the nucleotide sequence shown in SEQ ID No. 3.

In one embodiment the lipolytic enzyme according to the present invention may be a lipolytic enzyme obtainable, preferably obtained, from the *Streptomyces* strains L130 or L131 deposited by Danisco A/S of Langebrogade 1, DK-1001 Copenhagen K, Denmark under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 25 Jun. 2004 under accession numbers NCIMB 41226 and NCIMB 41227, respectively.

Preferably, the lipolytic enzyme according to the present invention acts on at least a glycolipid, such as digalactosyldiglyceride (DGDG) for example. Suitably, the lipolytic enzyme according to the present invention may also act on one or more other polar lipid substrates, such as a phospholipid, for example a lecithin, e.g. phosphatidylcholine.

An alternative way of expressing the term "capable of hydrolysing glycolipids" as used herein would be to say that the lipolytic enzyme has glycolipid hydrolysing activity.

Preferably, the lipolytic enzyme according to the present invention hydrolyses a glycolipid, such as digalactosyldiglyceride (DGDG) for example, and also a phospholipid, such as a lecithin, e.g. phosphatidylcholine.

Preferably the lipolytic enzyme according to the present invention acts on glycolipids such as DGDG or MGDG.

In one aspect the lipolytic enzyme according to the present invention hydrolyses DGDG to DGMG and/or MGDG to MGMG.

In one aspect the lipolytic enzyme according to the present invention hydrolyses lecithin to lysolecithin.

When it is the case that the lipolytic enzyme is capable of transferring an acyl group from at least a glycolipid to a donor substrate, the polar lipid substrate may be referred to herein as the "lipid acyl donor".

In one embodiment, the enzyme according to the present invention which as well as having phospholipase and/or glycolipase activity (generally classified as E.C. 3.1.1.26; E.C. 3.1.1.4 or E.C. 3.1.1.32 in accordance with the Enzyme Nomenclature Recommendations (1992) of the Nomenclature Committee of the International Union of Biochemistry and Molecular Biology) also has acyltransferase activity (generally classified as E.C. 2.3.1.x), whereby the enzyme is capable of transferring an acyl group from a lipid acyl donor to one or more acceptor substrates, such as one or more of the following: a sterol; a stanol; a carbohydrate; a protein; a protein subunit; glycerol.

Lipid acyltransferases and their uses are taught in co-pending International Patent Application number PCT/IB2004/000655. This document is incorporated herein by reference. However, the lipolytic enzymes from the genera *Streptomyces* according to the present invention are not taught in PCT/IB2004/000655.

In some aspects, the lipolytic enzyme for use in the methods and/or uses of the present invention may be capable of transferring an acyl group from a polar lipid (as defined herein) to one or more of the following acyl acceptor substrates: a sterol, a stanol, a carbohydrate, a protein or subunits thereof, or a glycerol.

For some aspects the "acyl acceptor" according to the present invention may be any compound comprising a hydroxy group (—OH), such as for example, polyvalent alcohols, including glycerol; sterol; stanols; carbohydrates; hydroxy acids including fruit acids, citric acid, tartaric acid, lactic acid and ascorbic acid; proteins or a sub-unit thereof, such as amino acids, protein hydrolysates and peptides (partly hydrolysed protein) for example; and mixtures and derivatives thereof.

In some aspects, the "acyl acceptor" according to the present invention may be preferably not water.

In one embodiment, the acyl acceptor is preferably not a monoglyceride and/or a diglyceride.

In one aspect, preferably the enzyme is capable of transferring an acyl group from a lipid to a sterol and/or a stanol.

In one aspect, preferably the enzyme is capable of transferring an acyl group from a lipid to a carbohydrate.

In one aspect, preferably the enzyme is capable of transferring an acyl group from a lipid to a protein or a subunit thereof. Suitably the protein subunit may be one or more of the following: an amino acid, a protein hydrolysate, a peptide, a dipeptide, an oligopeptide, a polypeptide.

Suitably in the protein or protein subunit the acyl acceptor may be one or more of the following constituents of the protein or protein subunit: a serine, a threonine, a tyrosine, or a cysteine.

When the protein subunit is an amino acid, suitably the amino acid may be any suitable amino acid. Suitably the amino acid may be one or more of a serine, a threonine, a tyrosine, or a cysteine for example.

In one aspect, preferably the enzyme is capable of transferring an acyl group from a lipid to glycerol.

In one aspect, preferably the enzyme is capable of transferring an acyl group from a lipid to a hydroxy acid.

In one aspect, preferably the enzyme is capable of transferring an acyl group from a lipid to a polyvalent alcohol.

In one aspect, the lipolytic enzyme may, as well as being able to transfer an acyl group from a lipid to a sterol and/or a stanol, additionally be able to transfer the acyl group from a lipid to one or more of the following: a carbohydrate, a protein, a protein subunit, glycerol.

The term lecithin as used herein encompasses phosphatidylcholine, phosphatidylethanolamine, phosphatidylinositol, phosphatidylserine and phosphatidylglycerol.

For some aspects, preferably the lipid substrate is at least a glycolipid, such as DGDG for example.

For some aspects, preferably the lipid substrate may be additionally a phospholipid, such as lecithin, for example phosphatidylcholine. Other phospholipid substrates in accordance with the present invention may be one or more of N acyl phosphatidyl ethanolamine (APE) or N acyl lyso-phosphatidyl ethanolamine (ALPE).

Preferably the lipid substrate is a food lipid, that is to say a lipid component of a foodstuff.

For some aspects, preferably the lipolytic enzyme according to the present invention is incapable, or substantially incapable, of acting on a triglyceride and/or a 1-monoglyceride and/or 2-monoglyceride.

In one embodiment the lipolytic enzyme according to the present invention has no activity or no significant activity on triglyceride and/or 1-monoglycerides and/or 2-monoglycerides.

Suitably, the lipid substrate or lipid acyl donor may be one or more lipids present in one or more of the following substrates: fats, including lard, tallow and butter fat; oils including oils extracted from or derived from palm oil, sunflower oil, soya bean oil, safflower oil, cotton seed oil, ground nut oil, corn oil, olive oil, peanut oil, coconut oil, and rapeseed oil. Lecithin from soya, rapeseed or egg yolk is also a suitable lipid substrate. The lipid substrate may be an oat lipid or other plant based material containing galactolipids.

In one aspect the lipid substrate or lipid acyl donor is preferably lecithin (such as phosphatidylcholine) in egg yolk.

For some aspects of the present invention, the lipid may be selected from lipids having a fatty acid chain length of from 8 to 22 carbons.

For some aspects of the present invention, the lipid may be selected from lipids having a fatty acid chain length of from 16 to 22 carbons, more preferably of from 16 to 20 carbons.

For some aspects of the present invention, the lipid may be selected from lipids having a fatty acid chain length of no greater than 14 carbons, suitably from lipids having a fatty acid chain length of from 4 to 14 carbons, suitably 4 to 10 carbons, suitably 4 to 8 carbons.

Suitably, the lipolytic enzyme according to the present invention exhibits at least glycolipase activity (E.C. 3.1.1.26). Suitably, the lipolytic enzyme according to the present invention may also exhibit phospholipase A2 activity (E.C. 3.1.1.4) and/or phospholipase A1 activity (E.C. 3.1.1.32).

For some aspects, the lipolytic enzyme according to the present invention may solely have glycolipase activity (E.C. 3.1.1.26).

For some aspects, the lipolytic enzyme according to the present invention is a galactolipase (E.C. 3.1.1.26). The fact that the enzyme is designated at a galactolipase does not, however, prevent it from having other side-activities, such as activity towards other polar lipids for example.

The terms "glycolipase activity" and "galactolipase activity" as used herein are used interchangeably.

Suitably, for some aspects the lipolytic enzyme according to the present invention may be capable of transferring an acyl group from a glycolipid and/or a phospholipid to one or more acceptor substrates.

Suitably the acceptor substrate may be one or more of the following substrates: a sterol, a stanol, a carbohydrate, a protein, glycerol.

The term "polar lipids" as used herein means phospholipids and/or glycolipids. In some aspects, the term polar lipids preferably means at least glycolipids.

The glycolipase activity; phospholipase activity and/or triacylglycerol lipase activity of an enzyme can be determined using the assays presented hereinbelow.

Determination of Galactolipase Activity (Glycolipase Activity Assay (GLU-7)):

Substrate 0.6% digalactosyldiglyceride (Sigma D 4651), 0.4% Triton-X 100 (Sigma X-100) and 5 mM $CaCl_2$ was dissolved in 0.05M HEPES buffer pH 7.

Assay Procedure:

400 µL substrate was added to an 1.5 mL Eppendorf tube and placed in an Eppendorf Thermomixer at 37° C. for 5 minutes. At time t=0 min, 50 µL enzyme solution was added. Also a blank with water instead of enzyme was analyzed. The sample was mixed at 10×100 rpm in an Eppendorf Thermomixer at 37° C. for 10 minutes. At time t=10 min the Eppendorf tube was placed in another thermomixer at 99° C. for 10 minutes to stop the reaction.

Free fatty acid in the samples was analyzed by using the NEFA C kit from WAKO GmbH.

Enzyme activity GLU at pH 7 was calculated as micromole fatty acid produced per minute under assay conditions Determination of Phospholipase Activity (Phospholipase Activity Assay (PLU-7)):

Substrate 0.6% L-α Phosphatidylcholine 95% Plant (Avanti #441601), 0.4% Triton-X 100 (Sigma X-100) and 5 mM $CaCl_2$ was dispersed in 0.05M HEPES buffer pH 7.

Assay Procedure:

400 μL substrate was added to a 1.5 mL Eppendorf tube and placed in an Eppendorf Thermomixer at 37° C. for 5 minutes. At time t=0 min, 50 μL enzyme solution was added. Also a blank with water instead of enzyme was analyzed. The sample was mixed at 10×100 rpm in an Eppendorf Thermomixer at 37° C. for 10 minutes. At time t=10 min the Eppendorf tube was placed in another thermomixer at 99° C. for 10 minutes to stop the reaction.

Free fatty acid in the samples was analyzed by using the NEFA C kit from WAKO GmbH.

Enzyme activity PLU-7 at pH 7 was calculated as micromole fatty acid produced per minute under assay conditions Determination of Triacylglyceride Lipase Activity: Assay Based on Triglyceride (Tributyrin) as Substrate (LIPU):

Lipase activity based on tributyrin is measured according to Food Chemical Codex, Forth Edition, National Academy Press, 1996, p 803. With the modification that the sample is dissolved in deionized water in stead of glycine buffer, and the pH stat set point is 5.5 instead of 7.

1 LIPU is defined as the quantity of enzyme which can liberate 1 micromole butyric acid per min. under assay conditions.

In one embodiment, preferably the lipolytic enzyme according to the present invention is a wild-type lipolytic enzyme.

The terms "natural" and "wild type" as used herein mean a naturally-occurring enzyme. That is to say an enzyme expressed from the endogenous genetic code and isolated from its endogenous host organism and/or a heterologously produced enzyme which has not been mutated (i.e. does not contain amino acid deletions, additions or substitutions) when compared with the mature protein sequence (after co- and post-translational cleavage events) endogenously produced. Natural and wild-type proteins of the present invention may be encoded by codon optimised polynucleotides for heterologous expression, and may also comprise a non-endogenous signal peptide selected for expression in that host.

The term "variant" as used herein means a protein expressed from a non-endogenous genetic code resulting in one or more amino acid alterations (i.e. amino acid deletions, additions or substitutions) when compared with the natural or wild-type sequence within the mature protein sequence.

Preferably, the lipolytic enzyme according to the present invention is obtainable (suitably may be obtained) from a bacterium.

Preferably, the lipolytic enzyme according to the present invention may be obtainable (preferably obtained) from Streptomyces spp. Preferably, the lipolytic enzyme according to the present invention may be obtainable (preferably obtained) from Streptomyces strain L131 or Streptomyces strain L130.

Preferably, the lipolytic enzyme according to the present invention comprises an amino acid sequence which has at least 70%, preferably at least 75%, preferably at least 80%, preferably at least 90%, preferably at least 95%, preferably at least 98%, preferably at least 99% identity with the amino acid sequence shown as SEQ ID No. 4.

Preferably, the nucleic acid encoding the lipolytic enzyme according to the present invention comprises a nucleotide sequence which has at least 75%, preferably at least 80%, preferably at least 85%, preferably at least 90%, preferably at least 95%, preferably at least 98%, preferably at least 99% identity with the nucleotide sequence shown in SEQ ID No. 3.

In one embodiment suitably the pH optimum of the enzyme on a galactolipid substrate is about 6-8, preferably about 6.5 to 7.5, more preferably about 7.

Suitably, the lipolytic enzyme according to the present invention may not be inhibited or not significantly be inhibited by lipases inhibitors present in wheat flour. The term "not significantly inhibited" as used herein means that the enzyme is less sensitive to lipase inhibitors present in the wheat flour when compared to an equivalent dosage (PLU) of LipopanF™ (Novozymes A/S, Denmark), as based on the standard phospholipase (PLU-7) assay defined herein.

Suitably, the lipolytic enzyme according to the present invention is capable of hydrolysing at least 10% of the galactolipid diester in the substrate (i.e. in the foodstuff, e.g. dough, for instance) to the monoester. Preferably, the enzyme is capable of hydrolysing at least 20%, more preferably at least 30%, at least 40%, at least 50%, at least 60%, at least 70%, at least 80% or at least 90% of the galactolipid diester to the mono ester. Suitably, the galactolipid diester may be one or more of MGDG or DGDG and the monoester may be one or more of MGMG or DGMG, respectively.

Suitably, the lipolytic enzyme according to the present invention may be isolated from a fermentation broth of Streptomyces strain L131 or Streptomyces strain L130.

Suitably, the enzyme may be purified by liquid chromatography.

The amino acid sequence of the purified lipolytic enzyme may be determined by Edman degradation, LC-MS and MALDI-TOF analysis.

Suitably, the enzyme as defined herein may catalyse one or more of the following reactions: interesterification, transesterification, alcoholysis, hydrolysis.

The term "interesterification" refers to the enzymatic catalysed transfer of acyl groups between a lipid donor and lipid acceptor, wherein the lipid donor is not a free acyl group.

The term "transesterification" as used herein means the enzymatic catalysed transfer of an acyl group from a lipid donor (other than a free fatty acid) to an acyl acceptor (other than water).

As used herein, the term "alcoholysis" refers to the enzymatic cleavage of a covalent bond of an acid derivative by reaction with an alcohol ROH so that one of the products combines with the H of the alcohol and the other product combines with the OR group of the alcohol.

As used herein, the term "alcohol" refers to an alkyl compound containing a hydroxyl group.

As used herein, the term "hydrolysis" refers to the enzymatic catalysed transfer of an acyl group from a lipid to the OH group of a water molecule. Acyl transfer which results from hydrolysis requires the separation of the water molecule.

The term "foodstuff" as used herein means a substance which is suitable for human and/or animal consumption.

Suitably, the term "foodstuff" as used herein may mean a foodstuff in a form which is ready for consumption. Alternatively or in addition, however, the term foodstuff as used herein may mean one or more food materials which are used in the preparation of a foodstuff. By way of example only, the term foodstuff encompasses both baked goods produced from dough as well as the dough used in the preparation of said baked goods.

In a preferred aspect the present invention provides a foodstuff as defined above wherein the foodstuff is selected from one or more of the following: eggs, egg-based products, including but not limited to mayonnaise, salad dressings, sauces, ice creams, egg powder, modified egg yolk and products made therefrom; baked goods, including breads, cakes, sweet dough products, laminated doughs, liquid batters, muffins, doughnuts, biscuits, crackers and cookies; confectionery, including chocolate, candies, caramels, halawa, gums, including sugar free and sugar sweetened gums, bubble gum, soft bubble gum, chewing gum and puddings; frozen products including sorbets, preferably frozen dairy products, including ice cream and ice milk; dairy products, including cheese, butter, milk, coffee cream, whipped cream, custard cream, milk drinks and yoghurts; mousses, whipped vegetable creams, meat products, including processed meat products; edible oils and fats, aerated and non-aerated whipped products, oil-in-water emulsions, water-in-oil emulsions, margarine, shortening and spreads including low fat and very low fat spreads; dressings, mayonnaise, dips, cream based sauces, cream based soups, beverages, spice emulsions and sauces.

Suitably the foodstuff in accordance with the present invention may be a "fine foods", including cakes, pastry, confectionery, chocolates, fudge and the like.

In one aspect the foodstuff in accordance with the present invention may be a dough product or a baked product, such as a bread, a fried product, a snack, cakes, pies, brownies, cookies, noodles, snack items such as crackers, graham crackers, pretzels, and potato chips, and pasta.

In a further aspect, the foodstuff in accordance with the present invention may be a plant derived food product such as flours, pre-mixes, oils, fats, cocoa butter, coffee whitener, salad dressings, margarine, spreads, peanut butter, shortenings, ice cream, cooking oils.

In another aspect, the foodstuff in accordance with the present invention may be a dairy product, including butter, milk, cream, cheese such as natural, processed, and imitation cheeses in a variety of forms (including shredded, block, slices or grated), cream cheese, ice cream, frozen desserts, yoghurt, yoghurt drinks, butter fat, anhydrous milk fat, other dairy products. The enzyme according to the present invention may improve fat stability in dairy products.

It is particularly advantageous to utilise the enzyme according to the present invention in cheese. Thus, a lipolytic enzyme in accordance with the present invention can advantageously be used to produce cheese. The lipolytic enzyme catalyses the hydrolysis of phospholipids in the milk which contributes to increased cheese yield. Preferably the lipolytic enzyme according to the present invention may be added to milk (referred to as cheese milk) prior to or during the cheese making process.

In another aspect, the foodstuff in accordance with the present invention may be a food product containing animal derived ingredients, such as processed meat products, cooking oils, shortenings.

In a further aspect, the foodstuff in accordance with the present invention may be a beverage, a fruit, mixed fruit, a vegetable or wine. In some cases the beverage may contain up to 20 g/l of added phytosterols.

In another aspect, the foodstuff in accordance with the present invention may be an animal feed. The animal feed may be enriched with phytosterol and/or phytostanols, preferably with beta-sitosterol/stanol. Suitably, the animal feed may be a poultry feed. When the foodstuff is poultry feed, the present invention may be used to lower the cholesterol content of eggs produced by poultry fed on the foodstuff according to the present invention.

In one aspect preferably the foodstuff is selected from one or more of the following: eggs, egg-based products, including mayonnaise, salad dressings, sauces, ice cream, egg powder, modified egg yolk and products made therefrom.

Preferably the foodstuff according to the present invention is a water containing foodstuff. Suitably the foodstuff may be comprised of 10-98% water, suitably 14-98%, suitably of 18-98% water, suitably of 20-98%, suitably of 40-98%, suitably of 50-98%, suitably of 70-98%, suitably of 75-98%.

For some aspects, the foodstuff in accordance with the present invention may not be a pure plant derived oil, such as olive oil, sunflower oil, peanut oil, rapeseed oil for instance. For the avoidance of doubt, in some aspects of the present invention the foodstuff according to the present invention may comprise an oil, but the foodstuff is not primarily composed of oil or mixtures of oil. For some aspects, preferably the foodstuff comprises less than 95% lipids, preferably less than 90% lipids, preferably less than 85%, preferably less than 80% lipids. Thus, for some aspects of the present invention oil may be a component of the foodstuff, but preferably the foodstuff is not an oil per se.

The advantages of using a lipolytic enzyme capable of transferring an acyl group in food applications is taught in patent applications WO2004/064987, WO2004/064537, PCT/IB2004/004374 and GB0513859.9 which are incorporated herein by reference.

The production of free fatty acids can be detrimental to foodstuffs. Free fatty acids have been linked with off-odours and/or off-flavours in foodstuffs, as well other detrimental effects, including a soapy taste in dairy products such as cheese for instance. Suitably in some embodiments of the present invention the lipolytic enzyme is capable of transferring the fatty acid from the lipid to an acyl acceptor, for example a sterol and/or a stanol. Hence, the overall level of free fatty acids in the foodstuff does not increase or increases only to an insignificant degree. Thus, a lipolytic enzyme capable of transferring an acyl group according to the present invention may provide one or more of the following unexpected technical effects in the production of cheese: a decrease in the oiling-off effect in cheese; an increase in cheese yield; an improvement in flavour; a reduced malodour; a reduced "soapy" taste.

The utilisation of a lipolytic enzyme taught herein which can transfer the acyl group to a carbohydrate as well as to a sterol and/or a stanol is particularly advantageous for foodstuffs comprising eggs. In particular, the presence of sugars, in particular glucose, in eggs and egg products is often seen as disadvantageous. Egg yolk may comprise up to 1% glucose. In accordance with the present invention this unwanted sugar can be readily removed by "esterifying" the sugar to form a sugar ester.

The presence of diglycerides in edible oils is disadvantageous. In particular, diglycerides in edible oils (in particular palm oil) can lead to a low quality oil. Suitably in some embodiments of the present invention a lipolytic enzyme taught herein is capable of transferring the fatty acid from the lipid to an acyl acceptor which reduces the level of diglycerides in the oil without increasing or significantly increasing the level of free fatty acids.

A lipolytic enzyme taught herein is able to hydrolyse a major part of the phospholipids in an edible or vegetable oil. This is highly advantageous in the enzymatic degumming of vegetable or edible oils. Suitably in some embodiments of the present invention the lipolytic enzyme may be capable of transferring the fatty acid from the lipid to an acyl acceptor. Hence, advantageously the overall level of free fatty acids in the oil does not increase or increases only to an insignificant degree. The production of free fatty acids can be detrimental in the edible oil. Preferably, the method according to the present invention results in the degumming of an edible oil wherein the accumulation of free fatty acids is reduced and/or eliminated.

The claims of the present invention are to be construed to include each of the foodstuffs listed above.

In some of the applications mentioned herein, particularly the food applications, such as the bakery applications, the lipolytic enzyme according to the present invention may be used with one or more conventional emulsifiers, including for example monoglycerides, diacetyl tartaric acid esters of mono- and diglycerides of fatty acids, sugar esters, sodium stearoyl lactylate (SSL) and lecithins.

In addition or alternatively, the enzyme according to the present invention may be used with one or more other suitable food grade enzymes. Thus, it is within the scope of the present invention that, in addition to the lipolytic enzyme of the present invention, at least one further enzyme may be added to the baked product and/or the dough. Such further enzymes include starch degrading enzymes such as endo- or exoamylases, pullulanases, debranching enzymes, hemicellulases including xylanases, cellulases, oxidoreductases, e.g. glucose oxidase, pyranose oxidase, sulfhydryl oxidase or a carbohydrate oxidase such as one which oxidises maltose, for example hexose oxidase (HOX), lipases, phospholipases and hexose oxidase, proteases, and acyltransferases (such as those described in PCT/IB2004/000575 for instance).

The present invention encompasses food enzyme compositions, including bread and/or dough improving compositions comprising the enzyme according to the present invention, and optionally further comprising another enzyme, such as one or more other suitable food grade enzymes, including starch degrading enzymes such as endo- or exoamylases, pullulanases, debranching enzymes, hemicellulases including xylanases, cellulases, oxidoreductases, e.g. glucose oxidase, pyranose oxidase, sulfhydryl oxidase or a carbohydrate oxidase such as one which oxidises maltose, for example hexose oxidase (HOX), lipases, phospholipases and hexose oxidase, proteases and acyltransferases (such as those described in PCT/IB2004/000575 for instance).

In some applications mentioned herein, particularly in food applications, such as the bakery applications, the lipolytic enzyme according to the present invention may be added in combination or sequentially with one or more enzyme substrates. By way of example only, the lipolytic enzyme according to the present invention may be added together with one or more polar lipid substrates and/or one or more acyl acceptor substrates.

In some applications mentioned herein, particularly in food applications, such as the bakery applications, the lipolytic enzyme according to the present invention may be used with one or more hydroxy acids, including for example tartaric acid, citric acid, lactic acid, succinic acid or ascorbic acid for example.

The term "improved properties" as used herein means any property which may be improved by the action of the lipolytic enzyme of the present invention. In particular, the use of the lipolytic enzyme according to the present invention results in one or more of the following characteristics: increased volume of the baked product; improved crumb structure of the baked product; anti-staling properties in the baked product; increased strength, increased stability, reduced stickiness and/or improved machinability of the dough.

The improved properties are evaluated by comparison with a dough and/or a baked product prepared without addition of the lipolytic enzyme according to the present invention.

The term "baked product" as used herein includes a product prepared from a dough. Examples of baked products (whether of white, light or dark type) which may advantageously produced by the present invention include one or more of the following: bread (including white, whole-meal and rye bread), typically in the form of loaves or rolls, steam buns, French baguette-type bread, pita bread, tacos, corn tortilla, wheat tortilla, cakes, pancakes, biscuits, crisp bread, pasta, noodles and the like.

The dough in accordance with the present invention may be a leavened dough or a dough to be subjected to leavening. The dough may be leavened in various ways such as by adding sodium bicarbonate or the like, or by adding a suitable yeast culture such as a culture of *Saccharomyces cerevisiae* (baker's yeast).

The present invention further relates to the use of the lipolytic enzyme in accordance with the present invention to produce a pasta dough, preferably prepared from durum flour or a flour of comparable quality.

The lipolytic enzyme according to the present invention is suitable for use in the enzymatic degumming of vegetable or edible oils. In processing of vegetable or edible oil the edible or vegetable oil is treated with lipolytic enzyme according to the present invention so as to hydrolyse a major part of the polar lipids (e.g. phospholipid). Preferably, the fatty acyl groups are hydrolysed from the polar lipids. The degumming process typically results in the reduction of the content of the polar lipids, particularly of phospholipids, in an edible oil due to hydrolyse of a major part (i.e. more than 50%) of the polar lipid, e.g. phospholipid. Typically, the aqueous phase containing the hydrolysed polar lipid (e.g. phospholipid) is separated from the oil. Suitably, the edible or vegetable oil may initially (pre-treatment with the enzyme according to the present invention) have a phosphorus content of 50-250 ppm.

In one embodiment, the present invention relates to the use of the lipolytic enzyme in accordance with the present invention in the bioconversion of polar lipids (preferably glycolipids) to make high value products, such as carbohydrate esters and/or protein esters and/or protein subunit esters and/or a hydroxy acid ester. The use of a lipolytic enzyme, particularly a lipolytic enzyme capable of transferring acyl groups from a polar lipid substrate (preferably a glycolipid) to a acyl acceptor, in the bioconversion of polar lipids and the advantages thereof is detailed in PCT/IB2004/004374 incorporated herein by reference.

In one embodiment the lipolytic enzyme for use in the methods of the present invention may be immobilised. When it is the case that the enzyme is immobilised the admixture comprising an acyl donor, optionally an acyl acceptor, and optionally water may be passed through a column for example comprising the immobilised enzyme. By immobilising the enzyme it is possible to easily reuse it.

Suitably, the immobilised enzyme may be used in a flow reactor or in a batch reactor containing a reaction mixture which comprises a lipid acyl donor and optionally an acyl acceptor dissolved in water. When the acyl acceptor is present the donor and acceptor are in a two-phase system or an emulsion. The reaction mixture may be optionally stirred or sonicated. Once the reaction has reached equilibrium for example, the reaction mixture and the immobilised enzyme may be separated. Suitably, the reaction product may be fractionated for example by hydrophobic interaction chromatography, crystallisation or high vacuum distillation.

Immobilised lipid acyl transferase can be prepared using immobilisation techniques known in the art. There are numerous methods of preparing immobilised enzymes, which will be apparent to a person skilled in the art (for example the techniques referred to in EP 0 746 608; or Balcao V. M. et al Enzyme Microb Technol. 1996 May 1; 18 (6):392-416; or Retz et al Chem Phys Lipids 1998 June:93 (1-2): 3-14; Bornscheuer et al Trends Biotechnol. 2002 October; 20 (10):433-7; Plou et al Biotechnology 92 (2002) 55-66; Warmuth et al 1992 Bio Forum 9, 282-283; Ferrer et al 2000 J. Chem. Technol. Biotechnol. 75, 1-8; or Christensen et al 1998 Nachwachsende Rohstoff 10, 98-105; Petersen and Christenen 2000 Applied Biocatalysis Harwood Academic Publishers, Amsterdam (each of which is incorporated herein by reference).

Techniques which may be used herein include covalent coupling to Eupergit C, adsorption on polypropylene and silica-granulation for example.

Lipolytic Enzymes in Accordance with the Present Invention

The lipolytic enzyme for use in accordance with the present invention and/or the methods described herein is preferably a lipolytic enzyme capable of hydrolysing at least galactolipids and/or capable of transferring an acyl group from at least a galactolipid to one or more acyl acceptor substrates, wherein the enzyme is encoded by a nucleic acid selected from the group consisting of:

d) a nucleic acid comprising a nucleotide sequence shown in SEQ ID No. 3;

e) a nucleic acid which is related to the nucleotide sequence of SEQ ID No. 3 by the degeneration of the genetic code; and f) a nucleic acid comprising a nucleotide sequence which has at least 70% identity with the nucleotide sequence shown in SEQ ID No. 3.

Preferably, the lipolytic enzyme used in accordance with the present invention and/or in the methods described herein is a lipolytic enzyme comprising an amino acid sequence as shown in SEQ ID No. 4 or an amino acid sequence which has at least 60% identity thereto.

However, the lipolytic enzyme for use in accordance with the present invention and/or in the methods of the present invention may be any lipolytic enzyme obtainable from *Streptomyces* species which is capable of hydrolysing at least a galactolipid and/or capable of transferring an acyl group from a galactolipid to one or more acyl acceptor substrates.

Suitable lipolytic enzymes having galactolipase activity for use in accordance with the present invention and/or in the methods of the present invention may comprise any one of the following amino acid sequences and/or be encoded by the following nucleotide sequences:

```
Thermobifida\fusca GDSx (SEQ ID NO: 31) 548 aa
                                                                SEQ ID No. 5
ZP_00058717
     1 mlphpagerg evgaffallv gtpqdrrlrl echetrplrg rcgcgerrvp pltlpgdgvl
    61 cttsstrdae tvwrkhlqpr pdggfrphlg vgcllagqgs pgvlwcgreg crfevcrrdt
   121 pglsrtrngd ssppfragws lppkcgeisq sarktpavpr ysllrtdrpd gprgrfvgsg
   181 cgcgccttcg cccgcggctt cgaactccgc ccaggacagg gtgtcggcga caggccgca
   181 praatrrrlf lgipalvlvt altlvlavpt gretlwrmwc eatqdwclgv pvdsrgqpae
   241 dgeflllspv qaatwgnyya lgdsyssgdg ardyypgtav kggcwrsana ypelvaeayd
   301 faghlsflac sgqrgyamld aidevgsqld wnsphtslvt igiggndlgf stvlktcmvr
   361 vplldskact dqedairkrm akfettfeel isevrtrapd arilvvgypr ifpeeptgay
   421 ytltasnqrw lnetiqefnq qlaeavavhd eeiaasggvg svefvdvyha ldgheigsde
   481 pwvngvqlrd latgvtvdrs tfhpnaaghr avgervieqi etgpgrplya tfavvagatv
   541 dtlagevg SEQ ID No. 6
     1 ggtggtgaac cagaacaccc ggtcgtcggc gtgggcgtcc aggtgcaggt gcaggttctt
    61 caactgctcc agcaggatgc cgccgtggcc gtgcacgatg gccttgggca ggcctgtggt
   121 ccccgacgag tacagcaccc atagcggatg gtcgaaccgc agcggggtga actccagttc
   181 cgcgccttcg cccgcggctt cgaactccgc ccaggacagg gtgtcggcga cagggccgca
   241 gcccaggtac ggcaggacga cggtgtgctg caggctgggc atgccgtcgc gcagggcttt
   301 gagcacgtca cggcggtcga agtccttacc gccgtagccg tagccgtcca cggccagcag
   361 cactttcggt tcgatctgcg cgaaccggtc gaggacgctg cgcaccccga agtcggggga
   421 acaggacgac caggtcgcac cgatcgcggc gcaggcgagg aatgcggccg tcgcctcggc
   481 gatgttcggc aggtaggcca cgacccggtc gccggggccc accccgaggc tgcggagggc
   541 cgcagcgatc gcggcggtgc gggtccgcag ttctccccag gtccactcgg tcaacggccg
   601 gagttcggac gcgtgccgga tcgccacggc tgatgggtca cggtcgcgga agatgtgctc
   661 ggcgtagttg agggtggcgc cggggaacca gacggcgccg ggcatggcgt cggaggcgag
   721 cactgtggtg tacggggtgg cggcgcgcac ccggtagtac tcccagatcg cggaccagaa
   781 tccttcgagg tcggttaccg accagcgcca cagtgcctcg tagtccggtg cgtccacacc
   841 gcggtgctcc cgcacccagc gggtgaacgc ggtgaggttg gcgcgttctt tgcgctcctc
   901 gtcgggactc cacaggatcg gcggctgcgg cttgagtgtc atgaaacgcg acccttcgt
   961 ggacggtgcg gatgcggtga gcgtcgggtg cctcccctaa cgctccccgg tgacggagtg
  1021 ttgtgcacca catctagcac gcgggacgcg gaaaccgtat ggagaaaaca cctacaaccc
  1081 cggccggacg gtggtttcg gccacactta ggggtcgggt gcctgcttgc cgggcagggc
  1141 agtcccgggg tgctgtggtg cgggcgggag ggctgtcgct tcgaggtgtg ccggcgggac
  1201 actccgggcc tcagccgtac ccgcaacggg gacagttctc ctcccttccg ggctggatgg
  1261 tcccttcccc cgaaatgcgg cgagatctcc cagtcagccc ggaaaacacc cgctgtgccc
  1321 aggtactctt tgcttcgaac agacaggccg gacggtccac ggggagggtt tgtgggcagc
  1381 ggaccacgtg cggcgaccag acgacggttg ttcctcggta tccccgctct tgtacttgtg
  1441 acagcgctca cgctggtctt ggctgtcccg acggggcgcg agacgctgtg gcgcatgtgg
  1501 tgtgaggcca cccaggactg gtgcctgggg gtgccggtcg actcccgcgg acagcctgcg
  1561 gaggacggcg agtttctgct gctttctccg gtccaggcag cgacctgggg gaactattac
  1621 gcgctcgggg attcgtactc ttcggggggac ggggcccgcg actactatcc cggcaccgcg
  1681 gtgaagggcg gttgctggcg gtccgctaac gcctatccgg agctggtcgc cgaagcctac
  1741 gacttcgccg gacacttgtc gttcctggcc tgcagcggcc agcgcggcta cgccatgctt
  1801 gacgctatcg acgaggtcgg ctcgcagctg gactggaact cccctcacac gtcgctggtg
  1861 acgatcggga tcggcggcaa cgatctgggg ttctccacgg ttttgaagac ctgcatggtg
  1921 cgggtgccgc tgctgacaga caaggcgtgc acggaccagg aggacgctat cgccaagcgg
  1981 atggcgaaat tcgagacgac gtttgaagag ctcatcagcg aagtgcgcac ccgcgcgccg
  2041 gacgcccgga tccttgtcgt gggctacccc cggattttc cggaggaacc gaccggcgcc
  2101 tactacacgc tgaccgcgag caaccagcgg tggctcaacg aaaccattca ggagttcaac
  2161 cagcagctcg ccgaggctgt cgcggtccac gacgaggaga ttgccgcgtc gggcggggtg
  2221 ggcagcgtgg agttcgtgga cgtctaccac gcgttggacg gccacgagat cggctcggac
```

-continued

```
2281 gagccgtggg tgaacggggt gcagttgcgg gacctcgcca ccggggtgac tgtggaccgc
2341 agtaccttcc accccaacgc cgctgggcac cgggcggtcg gtgagcggt catcgagcag
2401 atcgaaaccg gcccgggccg tccgctctat gccactttcg cggtggtggc gggggcgacc
2461 gtggacactc tcgcgggcga ggtggggtga cccggcttac cgtccggccc gcaggtctgc
2521 gagcactgcg gcgatctggt ccactgccca gtgcagttcg tcttcggtga tgaccagcgg
2581 cggggagagc cggatcggtg agccgtgcgt gtctttgacg agcacacccc gctgcaggag
2641 ccgttcgcac agttctcttc cggtggccag agtcgggtcg acgtcgatcc cagcccacag
2701 gccgatgctg cgggccgcga ccacgccgtt gccgaccagt tggtcgaggc gggcgcgcag
2761 cacggggggcg agggcgcgga catggtccag gtaagggccg tcgcggacga ggctcaccac
2821 ggcagtgccg accgcgcagg cgagggcgtt gccgccgaag gtgctgcccgg gctggccggg
2881 gcggatcacg tcgaagactt ccgcgtcgcc taccgccgcc gccacgggca ggatgccgcc
2941 gcccagcgct tgccgaaca ggtagatatc ggcgtcgact ccgctgtggt cgcaggcccg
//
```

Thermobifida\fusca\-GDSx (SEQ ID NO: 31)
SEQ ID No. 7
```
  1 vgsgpraatr rrlflgipal vlvtaltlvl avptgretlw rmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkrmakfett feelisevrt rapdarilvv gyprifpeep
241 tgayytltas nqrwlnetiq efnqqlaeav avhdeeiaas ggvgsvefvd vyhaldghei
301 gsdepwvngv qlrdlatgvt vdrstfhpna aghravgerv ieqietgpgr plyatfavva
361 gatvdtlage vg
```

Corynebacterium\effciens\GDSx (SEQ ID NO: 31) 300 aa
SEQ ID No. 8
```
  1 mrttviaasa llllagcadg areetagapp gesssggiree gaeastsitd vyialgdsya
 61 amggrdqplr gepfclrssg nypellhaev tdltcqgavt gdlleprtlg ertlpaqvda
121 ltedttlvtl siggndlgfg evagcireri agenaddcvd llgetigeql dqlppqldrv
181 heairdragd aqvvvtgylp lvsagdcpel gdvseadrrw aveltgqine tvreaaerhd
241 alfvlpddad ehtscappqq rwadiqgqqt dayplhptsa gheamaaavr dalglepvqp
//
```

SEQ ID No. 9
```
   1 ttctggggtg ttatggggtt gttatcggct cgtcctgggt ggatcccgcc aggtggggta
  61 ttcacggggg acttttgtgt ccaacagccg agaatgagtg ccctgagcgg tgggaatgag
 121 gtgggcgggg ctgtgtcgcc atgaggggggc ggcgggctct gtggtgcccc gcgacccccg
 181 gccccggtga gcggtgaatg aaatccggct gtaatcagca tcccgtgccc acccccgtcgg
 241 ggaggtcagc gcccggacgg tctacgcagt cggatccctc cggactcggc catgctgtcg
 301 gcagcatcgc gctcccgggt cttggcgtcc ctcggctgtt ctgcctgctg tccctggaag
 361 gcgaaatgat caccggggag tgatacaccg gtggtctcat cccggatgcc cacttcggcg
 421 ccatccggca attcgggcag ctccgggtgg aagtaggtgg catccgatgc gtcggtgacg
 481 ccatagtggg cgaagatctc atcctgctcg agggtgctca ggcactctc cggatcgata
 541 tcgggggcgt ccttgatggc gtccttgctg aaaccgaggt gcagcttgtg ggcttccaat
 601 ttcgcaccac ggagcgggac gaggctggaa tgacggccga agagcccgtg gtggacctca
 661 acgaaggtgg gtagtcccgt gtcatcattg aggaacacgc cctccaccgc acccagcttg
 721 tggccggagt tgtcgtaggc gctggcatcc agaagggaaa cgatctcata tttgtcggtg
 781 tgctcagaca tgatcttcct ttgctgtcgg tgtctggtac taccacggta gggctgaatg
 841 caactgttat ttttctgtta ttttaggaat tggtccatat cccacaggct ggctgtggtc
 901 aaatcgtcat caagtaatcc ctgtcacaca aaatgggtgg tgggagcct ggtcgcggtt
 961 ccgtggggag gcgccgtgcc cgcaggatcg tcggcatcgg cggatctgc cggtacccg
1021 cggtgaataa aatcattctg taaccttcat cacggttggt tttaggtatc cgccccttc
1081 gtcctgaccc cgtcccggc gcgcgggagc ccgcgggttg cggtagacag gggagacgtg
1141 gacaccatga ggacaacggt catcgcagca agcgcattac tccttctcgc cggatgcgcg
1201 gatggggcc gggaggagac cgccggtgca ccgccgggtg agtcctccgg gggcatccgg
1261 gaggagggg cggaggcgtc gacaagcatc accgacgtc acatcgcct cggggattcc
1321 tatgcggcga tgggcgggcg ggatcagccg ttacggggtg agccgttctg cctgcgctcg
1381 tccggtaatt acccggaact cctccacgca gaggtcaccg atctcacctg caggggggcg
1441 gtgaccgggg atctgctcga acccaggacg ctgggggagc gcacgctgcc ggcgcaggtg
1501 gatgcgctga cggaggacac caccctggtc ccctctccca tcgggggcaa tgacctcgga
1561 ttcgggggagg tggcgggatg catccgggaa cggatccgcc gggagaacgc tgatgattgc
1621 gtggacctgc tgggggaaac catccgggag cagctcgatc agcttccccc gcagctggac
1681 cgcgtgcacg aggctatccg ggaccgcgcc ggggacgcgc aggttgtggt caccggttac
1741 ctgccgctcg tgtctgccgg cgatgccccc gaactgggag atgtctccga ggcggatcgt
1801 cgttgggcgg ttgagctgac cgggcagatc aacgagaccg tgcgcgaggc ggccgaacga
1861 cacgatgccc tctttgtcct gcccgacgat gccgatgagc acaccagttg tgcacccca
1921 cagcagcgct gggcggatat ccaggccaa cagaccatg cctatccgct gcacccgacc
1981 tccgccggcc atgaggcgat ggccgccgcc gtccgggaca cgctgggcct ggaaccggtc
2041 cagccgtagc gccgggcgcg cgcttgtcga cgaccaaccc atgccaggct gcagtcacat
2101 ccgcacatag cgcgcgcggg cgatggagta cgcaccatag aggatgagcc cgatgccgac
2161 gatgatgagc agcacactgc cgaagggttg ttccccgagg gtgcgcagag ccgagtccag
2221 acctgcggcc tgctccgat catgggccca ggcagcaggg acgatcaaca ccccccaggat
2281 cccgaaggcg ataccacggc cgacataacc ggctgttccg gtgatgatga tcgcggtccc
2341 gacctgcct gacccgcac ccgcctccag atcctcccg aaatccgggg tggcccccctt
2401 ccagaggttg tagacacccg cccccagtac caccagcccg gcgaccacaa ccagcaccac
2461 acccagggt tgggataggga cggtgcggt gacatcggtg gcggtctcc catcggaggt
2521 gctgccgcc cgggcgaagg tggaggtggt caccgcaggg gagaagtaga ccatggccat
2581 gaccgccccc ttggccctttt ccttgaggtc ctcgccgcc agcagtggc tcaattgcca
2641 gagtcccagg gccgccaggg cgatgacggc aacccacagg aggaactgcc cacccggagc
2701 ctccgcgatg gtggccaggg cacctgaatt cgaggcctca tcacccgaac cgccggatcc
2761 agtggcgatg cgcaccgcga tccacccgat gaggatgtgc agtatgccca ggacaatgaa
```

-continued

```
2821 accacctctg gccagggtgg tcagcgcggg gtggtcctcg gcctggtcgg cagcccgttc
2881 gatcgtccgt ttcgcggatc tggtgtcgcc cttatccata gctcccattg aaccgccttg
2941 aggggtgggc ggccactgtc agggcggatt gtgatctgaa ctgtgatgtt ccatcaaccc
//
```

*S. coelicolor*\GDSx (SEQ ID NO: 31) 268 aa

SEQ ID No. 12

NP_625998.
```
  1 mrrfrlvgfl sslvlaagaa ltgaataqaa qpaaadgyva lgdsyssgvg agsyissssgd
 61 ckrstkahpy lwaaahspst fdftacsgar tgdvlsgqlg plssgtglvs isiggndagf
121 adtmttcvlq sessclsria taeayvdstl pgkldgvysa isdkapnahv vvigyprfyk
181 lgttciglse tkrtainkas dhlntvlaqr aaahgftfgd vrttftghel csgspwlhsv
241 nwlnigesyh ptaagqsggy lpvlngaa
//
```

SEQ ID No. 13
```
   1 cccggcggcc cgtgcaggag cagcagccgg cccgcgatgt cctcgggcgt cgtcttcatc
  61 aggccgtcca tcgcgtcggc gaccggcgcc gtgtagttgg cccggacctc gtcccaggtg
 121 cccgcggcga tctggccggt ggtgcggtgc ggccgcgcc gaggggagac gtaccagaag
 181 cccatcgtca cgttctccgg ctgcggttcg ggctcgtccg ccgctccgtc cgtcgcctcg
 241 ccgagcacct tctcggcgag gtcggcgctg gtcgccgtca ccgtgacgtc ggcgccccgg
 301 ctccagcgcg agatcagcag cgtccagccg tcgccctccg ccagcgtcgc gctgcggtcg
 361 tcgtcgcggg cgatccgccg cagcgcgcg cgggcgggca gcagcgtggc gccggaccgt
 421 acgcggtcga tgttcgccgc gtgcgagtac ggctgctcac ccgtggcgaa acggccgagg
 481 aacagcgcgt cgacgacgtc ggacggggag tcgctgtcgt ccacgttgag ccggatcggc
 541 agggcttcgt gcgggttcac ggacatgtcg ccatgatcgg cacccggcc gccgcgtgca
 601 cccgcttttc cgggcacgca cgacagggc tttctcgcgtcc gaacttgaac
 661 gagtgtcagc catttcttgg catggacact tccagtcaac gcgcgtagct gctaccacgc
 721 ttgtggcagc aatcctgcta agggaggttc catgagacgt ttccgacttg tcggcttcct
 781 gagttcgctc gtcctcgccg ccggcgccgc cctcaccggg gcagcgaccg cccaggcggc
 841 ccaacccgcc gccgccgacg gctatgtggc cctcggcgac tcctactcct ccggggtcgg
 901 agcgggcagc tacatcagct cgagcggcga ctgcaagcga agcacgaagg cccatccta
 961 cctgtgggcg ccgcccact cgcccccac gttcgacttc accgcctgtt ccggcgcccg
1021 tacggtgat gttctctccg gacagctcgg cccgctcagc tccggcaccg gctcgtctc
1081 gatcagcatc ggcggcaacg acgccggttt cgccgacacc atgacgacct gtgtgctcca
1141 gtccgagagc tcctgcctgt cgcggatcgc cacggccgag gcgtacgtcg actcgacgct
1201 gcccggcaag ctcgacggcg tctactcgg aatcagcgac aaggcgccga acgcccacgt
1261 cgtcgtcatc ggctaccgc gcttctacaa gctcggcacc acctgcatcg gcctgtccga
1321 gaccaagcgg acggcgatca caaggcctc cgaccactc aacaccgtcc tcgcccagcg
1381 cgccgcccgc cacggcttca ccttcggcga cgtacgacc accttcaccg gccacgagct
1441 gtgctccggc agccccggc tgcacagcgt caactggctg aacatcggcg agtcgtacca
1501 cccaccgcg gccggcagt ccggtggcta cctgccggtc ctcaacggcg ccgctgacc
1561 tcaggcgaa ggagaagaag aaggagcgga gggagacgag gagtgggagg ccccgcccga
1621 cggggtcccc gtccccgtc ccgtctccgt ccagtccgtc caagtccgtc agaacgccac
1681 cgcgtcggac gtgccccgca ccggactccg cacctccacg cgcacggcac tctcgaacgc
1741 gccggtgtcg tcgtgcgtcg tcaccaccac gccgtcctgg cgcgagcgct cgccgcccga
1801 cgggaaggac agcgtccgcc accccggatc ggagaccgac cgtccgcgg tcacccaccg
1861 gtagccgacc tccgcgggca gccgcccgac cgtgaacgtc gccgtgaacg cgggtgcccg
1921 gtcgtgcggc ggcggacagg ccccgagta gtgggtgcgc gagcccacca cggtcacctc
1981 caccgactgc gctgcggggc
//
```

*S. avermitilis*\GDSx (SEQ ID NO: 31) 269 aa

SEQ ID No. 14

NP__827753.
```
  1 mrrsritayv tsllavgca ltgaataqas paaaatgyva lgdsyssgvg agsylsssgd
 61 ckrsskaypy lwqaahspss fsfmacsgar tgdvlanqlg tlnsstglvs ltiggndagf
121 sdvmttcvlq sdsaclsrin takayvdstl pgqldsvyta istkapsahv avlgyprfyk
181 lggsclagls etkrsainda adylnsaiak raadhgftfg dvkstftghe icssstwlhs
241 ldllnigqsy hptaagqsgg ylpvmnsva
//
```

SEQ ID No. 15
```
   1 ccaccgccgg gtcggcggcg agtctcctgg cctcggtcgc ggagaggttg gccgtgtagc
  61 cgttcagccg ggcgccgaac gtcttcttca ccgtgccgcc gtactcgttg atcaggccgt
 121 tgcccttgct cgacgcggcc ttgaagccgg tgcccttctt gagcgtgacg atgtagctgc
 181 ccttgatcgc ggtgggggag ccgcggcga gcaccgtgcc ctcgccgggg gtggcctggg
 241 cggcagtgc ggtgaatccg cccacgaggg cgccggtcgc acggcggtt atcgcggcga
 301 tccggatctt cttgctacgc agctgtgcca tacgagggag tcctcctctg agcagtcgct
 361 cgcctggtgt gggcgcacgg ctgtgggggg tgcgcgcgtc atcacgcaca cggccctgga
 421 gcgtcgtgtt ccgccctggg ttgagtaaag cctcggccat tacggggt ggctcaaggg
 481 agttgagacc ctgtcatgag tctgacatga gcacgcaatc aacggggccg tgagcacccc
 541 ggggcgacc cggaaagtgc cgagaagtct tggcatggac acttcctgct aacacgcgta
 601 gctggtacga cggttacggc agagatcctg ctaaaggag gttccatgag acgttcccga
 661 attacggcat acgtgacctc actcctcctc gccgtcggct gcgcccccac cggggcagcg
 721 acggcgcagg cgtcccagc cgccgcggcc acgggctatg tggccctcgg cgactcgtac
 781 tcgtccggcg tcggcgccgg cagctacctc agctcgagcg gcgactgcaa gcgcagttcg
 841 aaggcctatc cgtacctctg caggccgcg cattcaccct cgtcgttcag tttcatggct
 901 tgctcggcg ctcgtacggg tgatgtcctg gccaatcagc tcggcaccct gaactcgtcc
 961 accggcctgg tctccctcac catcggaggc aacgacgcgg gcttctccga cgtcatgacg
1021 acctgtgtgc tccagtccga cagcgcctgc ctctccccgca tcaacacggc gaaggcgtac
1081 gtcgactcca ccctgccccg ccaactcgac agcgtgtaca cggcgatcag cacgaaggcc
```

-continued

```
    1141 ccgtcggccc atgtggccgt gctgggctac ccccgcttct acaaactggg cggctcctgc
    1201 ctcgcgggcc tctcggagac caagcggtcc gccatcaacg acgcggccga ctatctgaac
    1261 agcgccatcg ccaagcgcgc cgccgaccac ggcttcacct tcggcgacgt caagagcacc
    1321 ttcaccggcc atgagatctg ctccagcagc acctggctgc acagtctcga cctgctgaac
    1381 atcggccagt cctaccaccc gaccgcggcc ggccagtccg gcggctatct gccggtcatg
    1441 aacagcgtgg cctgagctcc cacggcctga attttaaggg cctgaatttt taaggcgaag
    1501 gtgaaccgga agcggaggcc ccgtccgtcg gggtctccgt cgcacaggtc accgagaacg
    1561 gcacggagtt ggacgtcgtg cgcaccgggt cgcgcacctc gacggcgatc tcgttcgaga
    1621 tcgttccgct cgtgtcgtac gtggtgacga acacctgctt ctgctgggtc tttccgccgc
    1681 tcgccgggaa ggacagcgtc ttccagcccg gatccgggac ctcgcccttc ttggtcaccc
    1741 agcggtactc cacctcgacc ggcacccggc ccaccgtgaa ggtcgccgtg aacgtgggcg
    1801 cctgggcggt gggcggcggg caggcaccgg agtagtcggt gtgcacgccg gtgaccgtca
    1861 ccttcacgga ctgggccggc ggggtcgtcg taccgccgcc gccaccgccg cctcccggag
    1921 tggagcccga gctgtggtcg ccccgccgt cggcgttgtc gtcctcgggg gttttcgaac
//
```

Thermobifida\fusca\-GDSx (SEQ ID NO: 31)

SEQ ID No. 16
```
      1 mgsgpraatr rrlflgipal vlvtaltlvl avptgretlw rmwceatqdw clgvpvdsrg
     61 qpaedgefll lspvqaatwg nyyalgdsys sgdgardyyp gtavkggcwr sanaypelva
    121 eaydfaghls flacsgqrgy amldaidevg sqldwnspht slvtigiggn dlgfstvlkt
    181 cmvrvpllds kactdqedai rkrmakfett feelisevrt rapdarilvv gyprifpeep
    241 tgayytltas nqrwlnetiq efnqqlaeav avhdeeiaas ggvgsvefvd vyhaldghei
    301 gsdepwvngv qlrdlatgvt vdrstfhpna aghravgerv ieqietgpgr plyatfavva
    361 gatvdtlage vg
//
```

Thermobifida\fusca\-GDSx (SEQ ID NO: 31)

SEQ ID No. 17
```
      1 ctgcagacac ccgccccgcc ttctcccgga tcgtcatgtt cggcgactcc ctcagcgaca
     61 ccggcaagat gtactccaag atgcgcggct acctgccgtc ctccccgccg tactacgagg
    121 gccgcttctc gaacggcccg gtctggctgg agcagctgac gaagcagttc cccggcctga
    181 cgatcgccaa cgaggccgag gggggcgcga ccgcagtcgc ctacaacaag atctcctgga
    241 acccgaagta ccaggtcatt aacaacctcg actacgaggt cacccagttc ttgcagaagg
    301 actcgttcaa gcccgacgac ctggtcatcc tgtgggtggg cgccaacgac tacctggcct
    361 acggttggaa cacggagcag gacgccaagc gggtgcgcga cgccatctcg gacgcggcaa
    421 accgcatggt cctgaacggc gcgaagcaga tcctgctgtt caacctgccc gacctgggcc
    481 agaacccgtc cgcccgctcc cagaaggtcg tcgaggccgt ctcgcacgtg tccgcctacc
    541 acaacaagct gctcctcaac ctcgcccggc agctcgcccc gacgggcatg gtcaagctgt
    601 tcgagatcga caagcagttc gcggagatgc tgcgcgaccc ccagaacttc ggcctgagcg
    661 acgtggagaa cccgtgctac gacggcggct acgtgtggaa gccgttcgcc acccggtccg
    721 tctcgaccga ccggcagctg tcggccttct cgccccagga gcgcctggcg atcgctggca
    781 acccgctcct ggcacaggcg gtagcttcgc cgatggcccg ccgctcggcc tcgcccctca
    841 actgcgaggg caagatgttc tgggaccagg tccacccac caccgtggtc cacgccgccc
    901 tctcggagcg cgccgccacc ttcatcgaga cccagtacga gttcctcgcc cactagtcta
    961 gaggatcc
```

Thus, in a further aspect, the present invention provides the use of a lipolytic enzyme comprising any one of the amino acid sequences shown as SEQ ID No. 4, 5, 7, 8, 12, 14, or 16 or an amino acid sequence which has at least 70%, 75%, 80%, 85%, 90%, 95%, 96%, 97% or 98% identity therewith, or encoded by any one of the nucleotide sequences shown as SEQ ID No. 3, 6, 9, 13, 15 or 17 or a nucleotide sequence which has at least 70%, 75%, 80%, 85%, 90%, 95%, 96%, 97% or 98% identity therewith, in a foodstuff for the preparation of a lyso-glycolipid, for example digalactosyl monoglyceride (DGMG) or monogalactosyl monoglyceride (MGMG) by treatment of a glycolipid (e.g. digalactosyl diglyceride (DGDG) or monogalactosyl diglyceride (MGDG)) with the lipolytic enzyme according to the present invention to produce the partial hydrolysis product, i.e. the lyso-glycolipid.

In a further aspect, the present invention yet further provides the use of a lipolytic enzyme comprising any one of the amino acid sequences shown as SEQ ID No. 4, 5, 7, 8, 12, 14 or 16 or an amino acid sequence which has at least 70%, 75%, 80%, 85%, 90%, 95%, 96%, 97% or 98% identity therewith, or encoded by any one of the nucleotide sequences shown as SEQ ID No. 3, 6, 9, 13, 15 or 17 or a nucleotide sequence which has at least 70%, 75%, 80%, 85%, 90%, 95%, 96%, 97% or 98% identity therewith, in a foodstuff for the preparation of a lyso-phospholipid, for example lysolecithin, by treatment of a phospholipid (e.g. lecithin) with the enzyme to produce the partial hydrolysis product, i.e. a lyso-phospholipid.

In another aspect, the present invention yet further provides the use of a lipolytic enzyme comprising any one of the amino acid sequences shown as SEQ ID No. 4, 5, 7, 8, 12, 14 or 16 or an amino acid sequence which has at least 70%, 75%, 80%, 85%, 90%, 95%, 96%, 97% or 98% identity therewith, or encoded by any one of the nucleotide sequences shown as SEQ ID No. 3, 6, 9, 13, 15 or 17 or a nucleotide sequence which has at least 70%, 75%, 80%, 85%, 90%, 95%, 96%, 97% or 98% identity therewith, in an egg or an egg-based product for the hydrolysis of phospholipids and/or glycolipids.

In another aspect the present invention provides the use of a lipolytic enzyme comprising any one of the amino acid sequences shown as SEQ ID No. 4, 5, 7, 8, 12, 14 or 16 or an amino acid sequence which has at least 70%, 75%, 80%, 85%, 90%, 95%, 96%, 97% or 98% identity therewith, or encoded by any one of the nucleotide sequences shown as SEQ ID No. 3, 6, 9, 13, 15 or 17 or a nucleotide sequence which has at least 70%, 75%, 80%, 85%, 90%, 95%, 96%, 97% or 98% identity therewith, in a substrate (preferably a foodstuff) for hydrolysing fatty acyl groups.

In another aspect the present invention provides the use of a lipolytic enzyme comprising any one of the amino acid sequences shown as SEQ ID No. 4, 5, 7, 8, 12, 14 or 16 or an amino acid sequence which has at least 70%, 75%, 80%, 85%, 90%, 95%, 96%, 97% or 98% identity therewith, or encoded by any one of the nucleotide sequences shown as SEQ ID No.

3, 6, 9, 13, 15 or 17 or a nucleotide sequence which has at least 70%, 75%, 80%, 85%, 90%, 95%, 96%, 97% or 98% identity therewith, in an edible oil for reducing the content of a phospholipid.

In a further aspect the present invention relates to the use of the lipolytic enzyme comprising any one of the amino acid sequences shown as SEQ ID No. 4, 5, 7, 8, 12, 14 or 16 or an amino acid sequence which has at least 70%, 75%, 80%, 85%, 90%, 95%, 96%, 97% or 98% identity therewith, or encoded by any one of the nucleotide sequences shown as SEQ ID No. 3, 6, 9, 13, 15 or 17 or a nucleotide sequence which has at least 70%, 75%, 80%, 85%, 90%, 95%, 96%, 97% or 98% identity therewith, in a substrate (preferably a bioconversion mixture comprising polar lipids (preferably glycolipids)) for the production of make high value products, such as carbohydrate esters and/or protein esters and/or protein subunit esters and/or a hydroxy acid ester.

In a preferable aspect, the present invention relates to a lipolytic enzyme comprising any one of amino sequences shown as SEQ ID No. 8, 14 or 16 or an amino acid sequence which has at least 70%, 75%, 80%, 85%, 90%, 95%, 96%, 97% or 98% identity therewith for the uses described herein.

More preferably the present invention relates to the use of a lipolytic enzyme comprising the amino acid sequence shown as SEQ ID No. 16 or an amino acid sequence which has at least 70%, 75%, 80%, 85%, 90%, 95%, 96%, 97% or 98% identity therewith.

In a broad aspect the present invention may provide a lipolytic enzyme capable of hydrolysing at least a glycolipid and/or capable of transferring an acyl group from at least a galactolipid to one or more acyl acceptors, wherein the enzyme is obtainable, preferably obtained, from *Thermobifida* spp, preferably *T. fusca*.

In another broad aspect the present invention may provide a lipolytic enzyme capable of hydrolysing at least a glycolipid and/or capable of transferring an acyl group from at least a galactolipid to one or more acyl acceptors, wherein the enzyme is obtainable, preferably obtained, from *Corynebacterium* spp, preferably *C. efficiens*.

In another broad aspect the present invention may provide a lipolytic enzyme capable of hydrolysing at least a glycolipid and/or capable of transferring an acyl group from at least a galactolipid to one or more acyl acceptors, wherein the enzyme is obtainable, preferably obtained, from *Streptomyces avermitilis*.

In a further aspect the present invention may provide a lipolytic enzyme capable of hydrolysing at least a glycolipid and/or capable of transferring an acyl group from at least a galactolipid to one or more acyl acceptors, wherein the enzyme comprises SEQ ID No. 5, 7, 8, 12, or 16 or an amino acid sequence which has at least 70%, 75%, 80%, 85%, 90%, 95%, 96%, 97% or 98% identity therewith, or the enzyme is encoded by any one of the nucleotide sequences shown as SEQ ID No. 6, 9, 13, or 17 or a nucleotide sequence which has at least 70%, 75%, 80%, 85%, 90%, 95%, 96%, 97% or 98% identity therewith.

In a further aspect the present invention may provide a lipolytic enzyme capable of hydrolysing at least a glycolipid and/or capable of transferring an acyl group from at least a galactolipid to one or more acyl acceptors, wherein the enzyme comprises SEQ ID No. 14 or an amino acid sequence which has at least 80%, 85%, 90%, 95%, 96%, 97% or 98% identity therewith, or the enzyme is encoded by any one of the nucleotide sequences shown as SEQ ID No. 15 or a nucleotide sequence which has at least 80%, 85%, 90%, 95%, 96%, 97% or 98% identity therewith.

In a further aspect the present invention may provide a lipolytic enzyme capable of hydrolysing at least a glycolipid and/or capable of transferring an acyl group from at least a galactolipid to one or more acyl acceptors, wherein the enzyme comprises SEQ ID No. 16 or an amino acid sequence which has at least 70%, 75%, 80%, 85%, 90%, 95%, 96%, 97% or 98% identity therewith, or the enzyme is encoded by any one of the nucleotide sequences shown as SEQ ID No. 17 or a nucleotide sequence which has at least 70%, 75%, 80%, 85%, 90%, 95%, 96%, 97% or 98% identity therewith.

In one embodiment of the present invention preferably the *Streptomyces* species from which the lipolytic enzyme is obtainable (or obtained) is not *Streptomyces rimosus*.

In one embodiment of the present invention preferably the *Streptomyces* species from which the lipolytic enzyme is obtainable (or obtained) is not *Streptomyces coelicolor*.

Advantages

One advantage of the present invention is that the lipolytic enzyme has significant glycolipid hydrolysing activity. This was surprising for a lipolytic enzyme from *Streptomyces* spp. In addition, this was surprising for a lipolytic enzyme from *Thermobifida* and *Corynebacterium* spp.

A further advantage of the present invention is that the lipolytic enzyme has no or no significant triacylglycerol hydrolysing activity.

Isolated

In one aspect, preferably the sequence is in an isolated form. The term "isolated" means that the sequence is at least substantially free from at least one other component with which the sequence is naturally associated in nature and as found in nature.

Purified

In one aspect, preferably the sequence is in a purified form. The term "purified" means that the sequence is in a relatively pure state—e.g. at least about 90% pure, or at least about 95% pure or at least about 98% pure.

Nucleotide Sequence

The scope of the present invention encompasses nucleotide sequences encoding enzymes having the specific properties as defined herein.

The term "nucleotide sequence" as used herein refers to an oligonucleotide sequence or polynucleotide sequence, and variants, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention does not include the native nucleotide sequence according to the present invention when in its natural environment and when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. However, the amino acid sequence encompassed by scope the present invention can be isolated and/or purified post expression of a nucleotide sequence in its native organism. Preferably, however, the amino acid sequence encompassed by scope of the present invention may be expressed by a nucleotide sequence in its native organism but wherein the nucleotide sequence is not under the control of the promoter with which it is naturally associated within that organism.

Preparation of the Nucleotide Sequence

Typically, the nucleotide sequence encompassed by scope of the present invention is prepared using recombinant DNA techniques (i.e. recombinant DNA). However, in an alternative embodiment of the invention, the nucleotide sequence could be synthesised, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232).

A nucleotide sequence encoding an enzyme which has the specific properties as defined herein may be identified and/or isolated and/or purified from any cell or organism producing said enzyme. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme or a part of the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for the enzyme (e.g. maltose for a glucosidase (maltase) producing enzyme), thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al., (1981) *Tetrahedron Letters* 22, p 1859-1869, or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science* (1988) 239, pp 487-491).

Due to degeneracy in the genetic code, nucleotide sequences may be readily produced in which the triplet codon usage, for some or all of the amino acids encoded by the original nucleotide sequence, has been changed thereby producing a nucleotide sequence with low homology to the original nucleotide sequence but which encodes the same, or a variant, amino acid sequence as encoded by the original nucleotide sequence. For example, for most amino acids the degeneracy of the genetic code is at the third position in the triplet codon (wobble position) (for reference see Stryer, Lubert, Biochemistry, Third Edition, Freeman Press, ISBN 0-7167-1920-7) therefore, a nucleotide sequence in which all triplet codons have been "wobbled" in the third position would be about 66% identical to the original nucleotide sequence however, the amended nucleotide sequence would encode for the same, or a variant, primary amino acid sequence as the original nucleotide sequence.

Therefore, the present invention further relates to any nucleotide sequence that has alternative triplet codon usage for at least one amino acid encoding triplet codon, but which encodes the same, or a variant, polypeptide sequence as the polypeptide sequence encoded by the original nucleotide sequence.

Furthermore, specific organisms typically have a bias as to which triplet codons are used to encode amino acids. Preferred codon usage tables are widely available, and can be used to prepare codon optimised genes. Such codon optimisation techniques are routinely used to optimise expression of transgenes in a heterologous host.

Molecular Evolution

Once an enzyme-encoding nucleotide sequence has been isolated, or a putative enzyme-encoding nucleotide sequence has been identified, it may be desirable to modify the selected nucleotide sequence, for example it may be desirable to mutate the sequence in order to prepare an enzyme in accordance with the present invention.

Mutations may be introduced using synthetic oligonucleotides. These oligonucleotides contain nucleotide sequences flanking the desired mutation sites.

A suitable method is disclosed in Morinaga et al (Biotechnology (1984) 2, p 646-649). Another method of introducing mutations into enzyme-encoding nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796. Error prone PCR technologies are suitable for the production of variants of lipolytic enzymes with preferred characteristics. WO0206457 refers to molecular evolution of lipases.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. DNA shuffling and family shuffling technologies are suitable for the production of variants of lipid acyl transferases with preferred characteristics. Suitable methods for performing 'shuffling' can be found in EP0 752 008, EP1 138 763, EP1 103 606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo mediated recombination methods (see WO 00/58517, U.S. Pat. No. 6,344,328, U.S. Pat. No. 6,361,974), for example, molecular evolution can be performed where the variant produced retains very low homology to known enzymes or proteins. Such variants thereby obtained may have significant structural analogy to known lipolytic enzymes, but have very low amino acid sequence homology.

As a non-limiting example, In addition, mutations or natural variants of a polynucleotide sequence can be recombined with either the wild type or other mutations or natural variants to produce new variants. Such new variants can also be screened for improved functionality of the encoded polypeptide.

The application of the above-mentioned and similar molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimisation or alteration of enzyme activity, such examples include, but are not limited to one or more of the following: optimised expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, substrate As will be apparent to a person skilled in the art, using molecular evolution tools an enzyme may be altered to improve the functionality of the enzyme.

Suitably, the lipolytic enzyme used in the invention may be a variant, i.e. may contain at least one amino acid substitution, deletion or addition, when compared to a parental enzyme. Variant enzymes retain at least 20%, 30%, 40%, 50%, 60%, 70%, 80%, 90%, 95%, 97%, 99% homology with the parent enzyme. Suitable parent enzymes may include any enzyme with esterase or lipase activity. Preferably, the parent enzyme aligns to the pfam00657 consensus sequence.

In a preferable embodiment a variant lipolytic enzyme retains or incorporates at least one or more of the pfam00657 consensus sequence amino acid residues found in the GDSx (SEQ ID NO: 31), GANDY (SEQ ID NO: 35) and HPT blocks.

Enzymes, such as lipases with no or low galactolipase and/or phospholipase activity in an aqueous environment may be mutated using molecular evolution tools to introduce or enhance the galactolipase and/or phospholipase activity, thereby producing a lipolytic enzyme with significant galactolipase and/or phospholipase activity suitable for use in the compositions and methods of the present invention.

Suitably the variant enzyme may have no activity on triglycerides and/or monoglycerides and/or diglycerides.

Alternatively, the variant enzyme for use in the invention may have increased activity on triglycerides, and/or may also have increased activity on one or more of the following, polar lipids, phospholipids, lecithin, phosphatidylcholine, glycolipids, digalactosyl monoglyceride, monogalactosyl monoglyceride.

Amino Acid Sequences

The scope of the present invention also encompasses amino acid sequences of enzymes having the specific properties as defined herein.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

The enzyme encompassed in the present invention may be used in conjunction with other enzymes. Thus the present invention also covers a combination of enzymes wherein the combination comprises the enzyme of the present invention and another enzyme, which may be another enzyme according to the present invention. This aspect is discussed in a later section.

Preferably the amino acid sequence when relating to and when encompassed by the per se scope of the present invention is not a native enzyme. In this regard, the term "native enzyme" means an entire enzyme that is in its native environment and when it has been expressed by its native nucleotide sequence.

Identity/Homology

The present invention also encompasses the use of homologues of any amino acid sequence of an enzyme or of any nucleotide sequence encoding such an enzyme.

Here, the term "homologue" means an entity having a certain homology with the amino acid sequences and the nucleotide sequences. Here, the term "homology" can be equated with "identity". These terms will be used interchangeably herein.

In the present context, a homologous amino acid sequence is taken to include an amino acid sequence which may be at least 87 or 90% identical, preferably at least 95, 96, 97, 98 or 99% identical to the sequence. Typically, the homologues will comprise the same active sites etc.—e.g. as the subject amino acid sequence. Although homology can also be considered in terms of similarity (i.e. amino acid residues having similar chemical properties/functions), in the context of the present invention it is preferred to express homology in terms of sequence identity.

In the present context, an homologous nucleotide sequence is taken to include a nucleotide sequence which may be at least 85 or 90% identical, preferably at least 95, 96, 97, 98 or 99% identical to a nucleotide sequence encoding an enzyme of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

For the amino acid sequences and the nucleotide sequences, homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p 387). Examples of other software than can perform sequence comparisons include, but are not limited to, the BLAST package (see Ausubel et al., 1999 *Short Protocols in Molecular Biology*, 4$^{th}$ Ed—Chapter 18), FASTA (Altschul et al., 1990 *J. Mol. Biol.* 403-410) and the GENEWORKS suite of comparison tools. Both BLAST and FASTA are available for offline and online searching (see Ausubel et al., 1999, *Short Protocols in Molecular Biology*, pages 7-58 to 7-60).

However, for some applications, it is preferred to use the GCG Bestfit program. A new tool, called BLAST 2 Sequences is also available for comparing protein and nucleotide sequence (see *FEMS Microbiol Lett* 1999 174 (2): 247-50; and *FEMS Microbiol Lett* 1999 177 (1): 187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), *Gene* 73 (1), 237-244).

Once the software has produced an optimal alignment, it is possible to calculate % homology, preferably % sequence identity. The software typically does this as part of the sequence comparison and generates a numerical result.

In a preferable aspect of the present invention the following software and settings for calculating percentage sequence homology/identity are used. For amino acid sequences percentage of identities (homology) or "positives" are calculated by the AlignX Vector NTI (Vector NTI Advance 9.1 from Invitrogen Corporation, Carlsbad, Calif., USA.) for each possible pair of amino acid sequences. Settings are default parameters (Gap opening penalty −10, Gap extension penalty 0.1).

For nucleic acid sequences percentage of identities (homology) or "positives" are calculated by the AlignX VectorNTI programme from Informax Inc. (USA) for each possible pair of nucleic acid sequences. Settings are default settings which for DNA is: Gap opening penalty: 15 and Gap extension penalty: 6.66. (same settings for multiple alignments).

Preferably the amino acid identity (homology) is calculated across the full-length amino acid sequence (e.g. SEQ IDs 4, 5, 7, 8, 10, 12 and 14), or for nucleic acid to a corresponding polynucleotide which encodes the respective the full-length amino acid sequence. Amino acid or nucleic acid identity (homology) may be, preferably, calculated by comparing the homology/identity over the mature polypeptide sequence, i.e. a polypeptide sequence which has been co- or post-translationally processed, for example by cleavage of an N-terminal signal peptide, or a C-terminal cleavage event.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids can be grouped together based on the properties of their side chain alone. However it is more useful to include mutation data as well. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" *Comput. Appl Biosci.* 9: 745-756) (Taylor W. R. (1986) "The classification of amino acid conservation" *J. Theor. Biol.* 119; 205-218). Conservative substitutions may be made, for example according to the table below which describes a generally accepted Venn diagram grouping of amino acids.

| | SET | | SUB-SET | |
|---|---|---|---|---|
| Hydro-phobic | F W Y H K M I L V A G C | | Aromatic Aliphatic | F W Y H I L V |
| Polar | W Y H K R E D C S T N Q | | Charged Positively charged Negatively charged | H K R E D H K R E D |
| Small | V C A G S P T N D | | Tiny | A G S |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation involves the presence of one or more amino acid residues in peptoid form, and will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89 (20), 9367-9371 and Horwell D C, *Trends Biotechnol.* (1995) 13 (4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector.

Biologically Active

Preferably, the variant sequences etc. are at least as biologically active as the sequences presented herein.

As used herein "biologically active" refers to a sequence having a similar structural function (but not necessarily to the same degree), and/or similar regulatory function (but not necessarily to the same degree), and/or similar biochemical function (but not necessarily to the same degree) of the naturally occurring sequence.

Hybridisation

The present invention also encompasses sequences that are complementary to the nucleic acid sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the sequences presented herein, or any derivative, fragment or derivative thereof.

The term "variant" also encompasses sequences that are complementary to sequences that are capable of hybridising to the nucleotide sequences presented herein.

Preferably, the term "variant" encompasses sequences that are complementary to sequences that are capable of hybridising under stringent conditions (e.g. 50° C. and 0.2×SSC {1×SSC=0.15 M NaCl, 0.015 M Na$_3$citrate pH 7.0}) to the nucleotide sequences presented herein.

More preferably, the term "variant" encompasses sequences that are complementary to sequences that are capable of hybridising under high stringent conditions (e.g.

65° C. and 0.1×SSC {1×SSC=0.15 M NaCl, 0.015 M Na₃citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

Also included within the scope of the present invention are polynucleotide sequences that are capable of hybridising to the nucleotide sequences presented herein under conditions of intermediate to maximal stringency.

In a preferred aspect, the present invention covers nucleotide sequences that can hybridise to the nucleotide sequence of the present invention, or the complement thereof, under stringent conditions (e.g. 50° C. and 0.2×SSC).

In a more preferred aspect, the present invention covers nucleotide sequences that can hybridise to the nucleotide sequence of the present invention, or the complement thereof, under high stringent conditions (e.g. 65° C. and 0.1×SSC).

Recombinant

In one aspect the sequence for use in the present invention is a recombinant sequence—i.e. a sequence that has been prepared using recombinant DNA techniques.

These recombinant DNA techniques are within the capabilities of a person of ordinary skill in the art. Such techniques are explained in the literature, for example, J. Sambrook, E. F. Fritsch, and T. Maniatis, 1989, *Molecular Cloning: A Laboratory Manual*, Second Edition, Books 1-3, Cold Spring Harbor Laboratory Press.

Synthetic

In one aspect the sequence for use in the present invention is a synthetic sequence—i.e. a sequence that has been prepared by in vitro chemical or enzymatic synthesis. It includes, but is not limited to, sequences made with optimal codon usage for host organisms—such as the methylotrophic yeasts *Pichia* and *Hansenula*.

Expression of Enzymes

The nucleotide sequence for use in the present invention may be incorporated into a recombinant replicable vector. The vector may be used to replicate and express the nucleotide sequence, in enzyme form, in and/or from a compatible host cell.

Expression may be controlled using control sequences e.g. regulatory sequences.

The enzyme produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated into the genome of a suitable host organism. The term "incorporated" preferably covers stable incorporation into the genome.

The nucleotide sequence of the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described below to provide for expression of a polypeptide of the present invention.

The choice of vector e.g. a plasmid, cosmid, or phage vector will often depend on the host cell into which it is to be introduced.

The vectors for use in the present invention may contain one or more selectable marker genes-such as a gene, which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme of the present invention may also be achieved by the selection of heterologous regulatory regions, e.g. promoter, secretion leader and terminator regions.

Preferably, the nucleotide sequence according to the present invention is operably linked to at least a promoter.

Examples of suitable promoters for directing the transcription of the nucleotide sequence in a bacterial, fungal or yeast host are well known in the art.

Constructs

The term "construct"—which is synonymous with terms such as "conjugate", "cassette" and "hybrid"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct of the present invention comprises at least the nucleotide sequence of the present invention operably linked to a promoter.

Host Cells

The term "host cell"—in relation to the present invention includes any cell that comprises either the nucleotide sequence or an expression vector as described above and which is used in the recombinant production of an enzyme having the specific properties as defined herein.

Thus, a further embodiment of the present invention provides host cells transformed or transfected with a nucleotide sequence that expresses the enzyme of the present invention. The cells will be chosen to be compatible with the said vector and may for example be prokaryotic (for example bacterial), fungal, yeast or plant cells. Preferably, the host cells are not human cells.

Examples of suitable bacterial host organisms are gram positive or gram negative bacterial species.

Depending on the nature of the nucleotide sequence encoding the enzyme of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

The host cell may be a protease deficient or protease minus strain.

The genotype of the host cell may be modified to improve expression.

Examples of host cell modifications include protease deficiency, supplementation of rare tRNA's, and modification of the reductive potential in the cytoplasm to enhance disulphide bond formation.

For example, the host cell *E. coli* may overexpress rare tRNA's to improve expression of heterologous proteins as exemplified/described in Kane (*Curr Opin Biotechnol* (1995), 6, 494-500 "Effects of rare codon clusters on high-level expression of heterologous proteins in *E. coli*"). The host cell may be deficient in a number of reducing enzymes thus favouring formation of stable disulphide bonds as exemplified/described in Bessette (*Proc Natl Acad Sci USA* (1999), 96, 13703-13708 "Efficient folding of proteins with multiple disulphide bonds in the *Escherichia coli* cytoplasm").

In one embodiment the host cell is a bacteria, preferably a gram-positive bacteria, preferably a host cell selected from Actinobacteria, such as *Biofidobacteria* and *Aeromonas*, particularly preferably *Aeromonas salmonicida*. Still more preferred are Actinomicetales such as Corynebacteria, in particular *Corynebacterium glutamicum* and *Nocardia*. Particularly preferred are Streptomycetaceae, such as *Streptomyces*, especially *S. lividans*.

A microbial host can be used for expression of the galactolipase gene, e.g. Eubacteria, Archea or Fungi, including yeast. Preferred are Eubacteria, for example, Firmicutes (low GC-Gram positive bacteria), such as *Bacillus subtilis* and other *bacillus* species, lactic acid bacteria such as species of genera *Lactobacillus* and *Lactococcus*.

Also preferred are Gram-negative Proteobacteria, in particular Gammaproteobacteria, such as host species belonging to the genera *Pseudomonas, Xanthomonas, Citrobacter* and *Escherichia*, especially *Escherichia coli*.

In another embodiment the host cell is the same genus as the native host species, i.e. the recombinant gene is re-introduced and expressed in a species from the same genus as the species from which the recombinant gene was isolated.

In another embodiment the host cell is the native host species, i.e. the recombinant gene is re-introduced and expressed in the same species from which the recombinant gene was isolated.

Organism

The term "organism" in relation to the present invention includes any organism that could comprise the nucleotide sequence coding for the enzyme according to the present invention and/or products obtained therefrom, and/or wherein a promoter can allow expression of the nucleotide sequence according to the present invention when present in the organism.

Suitable organisms may include a prokaryote, fungus, yeast or a plant.

The term "transgenic organism" in relation to the present invention includes any organism that comprises the nucleotide sequence coding for the enzyme according to the present invention and/or the products obtained therefrom, and/or wherein a promoter can allow expression of the nucleotide sequence according to the present invention within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, the nucleotide sequence coding for the enzyme according to the present invention, constructs according to the present invention, vectors according to the present invention, plasmids according to the present invention, cells according to the present invention, tissues according to the present invention, or the products thereof.

For example the transgenic organism may also comprise the nucleotide sequence coding for the enzyme of the present invention under the control of a heterologous promoter.

Transformation of Host Cells/Organism

As indicated earlier, the host organism can be a prokaryotic or a eukaryotic organism. Examples of suitable prokaryotic hosts include *E. coli* and *Bacillus subtilis*.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol* [1991] 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

Transformed Fungus

A host organism may be a fungus—such as a filamentous fungus. Examples of suitable such hosts include any member belonging to the genera *Thermomyces, Acremonium, Aspergillus, Penicillium, Mucor, Neurospora, Trichoderma* and the like.

Teachings on transforming filamentous fungi are reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings on transforming filamentous fungi are reviewed in U.S. Pat. No. 5,674,707.

In one aspect, the host organism can be of the genus *Aspergillus*, such as *Aspergillus niger*.

A transgenic *Aspergillus* according to the present invention can also be prepared by following, for example, the teachings of Turner G. 1994 (Vectors for genetic manipulation. In: Martinelli S. D., Kinghorn J. R. (Editors) *Aspergillus:* 50 years on. Progress in industrial microbiology vol 29. Elsevier Amsterdam 1994. pp. 641-666). Gene expression in filamentous fungi has been reviewed in Punt et al. (2002) Trends Biotechnol 2002 May; 20(5):200-6, Archer & Peberdy Crit. Rev Biotechnol (1997) 17 (4):273-306.

Transformed Yeast

In another embodiment, the transgenic organism can be a yeast.

A review of the principles of heterologous gene expression in yeast are provided in, for example, *Methods Mol Biol* (1995), 49:341-54, and *Curr Opin Biotechnol* (1997) October; 8 (5):554-60

In this regard, yeast—such as the species *Saccharomyces cereviseae* or *Pichia pastoris* (see FEMS Microbiol Rev (2000 24 (1):45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", *Yeasts*, Vol 5, Anthony H Rose and J Stuart Harrison, eds, 2nd edition, Academic Press Ltd.).

For the transformation of yeast, several transformation protocols have been developed. For example, a transgenic *Saccharomyces* according to the present invention can be prepared by following the teachings of Hinnen et al., (1978, *Proceedings of the National Academy of Sciences of the USA* 75, 1929); Beggs, J D (1978, *Nature*, London, 275, 104); and Ito, H et al (1983, J Bacteriology 153, 163-168).

The transformed yeast cells may be selected using various selective markers—such as auxotrophic markers dominant antibiotic resistance markers.

Transformed Plants/Plant Cells

A host organism suitable for the present invention may be a plant. A review of the general techniques may be found in articles by Potrykus (*Annu Rev Plant Physiol Plant Mol Biol* [1991] 42:205-225) and Christou (Agro-Food-Industry Hi-Tech March/April 1994 17-27).

Culturing and Production

Host cells transformed with the nucleotide sequence of the present invention may be cultured under conditions conducive to the production of the encoded enzyme and which facilitate recovery of the enzyme from the cells and/or culture medium.

The medium used to cultivate the cells may be any conventional medium suitable for growing the host cell in questions and obtaining expression of the enzyme.

The protein produced by a recombinant cell may be displayed on the surface of the cell.

The enzyme may be secreted from the host cells and may conveniently be recovered from the culture medium using well-known procedures.

Secretion

Often, it is desirable for the enzyme to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces, Kluyveromyces* and *Hansenula*) or the α-amylase gene (*Bacillus*).

By way of example, the secretion of heterologous proteins in *E. coli* is reviewed in Methods Enzymol (1990) 182:132-43.

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Also, recombinant immunoglobulins may be produced as shown in U.S. Pat. No. 4,816,567.

Fusion Proteins

The amino acid sequence for use according to the present invention may be produced as a fusion protein, for example to aid in extraction and purification. Examples of fusion protein partners include glutathione-S-transferase (GST), 6×His (SEQ ID NO: 33), GAL4 (DNA binding and/or transcriptional activation domains) and (β-galactosidase). It may also be convenient to include a proteolytic cleavage site between the fusion protein partner and the protein sequence of interest to allow removal of fusion protein sequences.

Preferably, the fusion protein will not hinder the activity of the protein sequence.

Gene fusion expression systems in *E. coli* have been reviewed in *Curr Opin Biotechnol* (1995) 6 (5):501-6.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

Large Scale Application

In one preferred embodiment of the present invention, the amino acid sequence is used for large scale applications.

Preferably the amino acid sequence is produced in a quantity of from 1 g per liter to about 2 g per liter of the total cell culture volume after cultivation of the host organism.

Preferably the amino acid sequence is produced in a quantity of from 100 mg per liter to about 900 mg per liter of the total cell culture volume after cultivation of the host organism.

Preferably the amino acid sequence is produced in a quantity of from 250 mg per liter to about 500 mg per liter of the total cell culture volume after cultivation of the host organism.

Food

The composition of the present invention may be used as—or in the preparation of—a food. Here, the term "food" is used in a broad sense—and covers food for humans as well as food for animals (i.e. a feed). In a preferred aspect, the food is for human consumption.

The food may be in the form of a solution or as a solid—depending on the use and/or the mode of application and/or the mode of administration.

Food Ingredient

The composition of the present invention may be used as a food ingredient.

As used herein the term "food ingredient" includes a formulation, which is or can be added to functional foods or foodstuffs and includes formulations which can be used at low levels in a wide variety of products that require, for example, acidifying or emulsifying.

The food ingredient may be in the form of a solution or as a solid—depending on the use and/or the mode of application and/or the mode of administration.

Food Products

The composition of the present invention can be used in the preparation of food products such as one or more of: confectionery products, dairy products, meat products, poultry products, fish products and bakery products.

The present invention also provides a method of preparing a food or a food ingredient, the method comprising admixing a lipolytic enzyme according to the present invention with another food ingredient.

Further preferable aspects are presented in the accompanying claims and in the following Figures and examples.

FIG. 1 shows PCR fragment SEQ ID No. 1, which is a partial non-enzyme encoding polynucleotide; this sequence is a ribosomal 16S RNA gene widely used for taxonomic comparisons;

FIG. 2 shows PCR fragment SEQ ID No. 2, which is a partial non-enzyme encoding polynucleotide; this sequence is a ribosomal 16S RNA gene widely used for taxonomic comparisons;

FIG. 3 shows a polynucleotide encoding a lipolytic enzyme according to the present invention (SEQ ID No. 3);

FIG. 4 shows an amino acid sequence of a lipolytic enzyme according to the present invention (SEQ ID No. 4);

Figure 10:
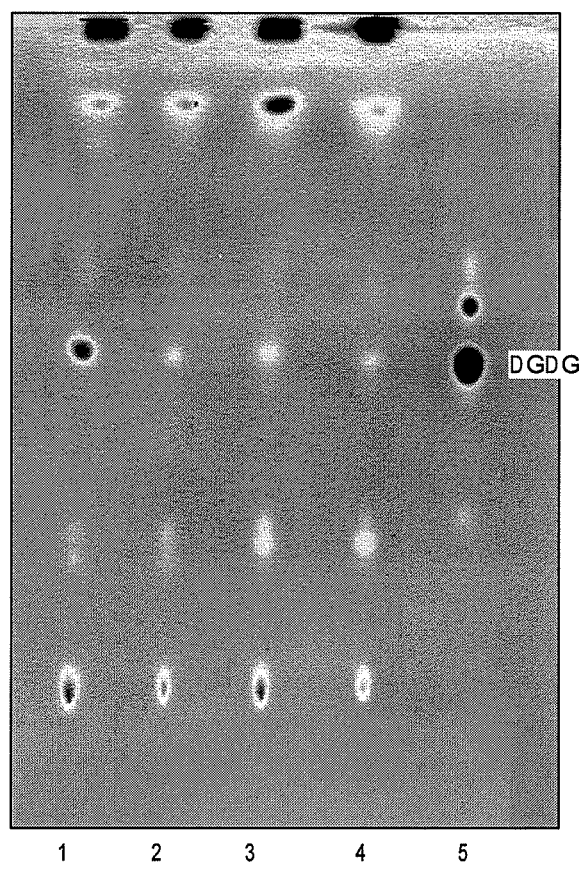

FIG. 10 shows a TLC plate of lipids extracted from dough treated with a lipolytic enzyme from *Streptomyces* expressed in *E. coli* labelled #236; Lane 1=control; Lane 2=#236, 0.225PLU-7/g flour; Lane 3=#236, 0.45 PLU-7/g flour; Lane 4=#236, 0.675 PLU-7/g flour; Lane 5=DGDG reference material.

Figure 11:
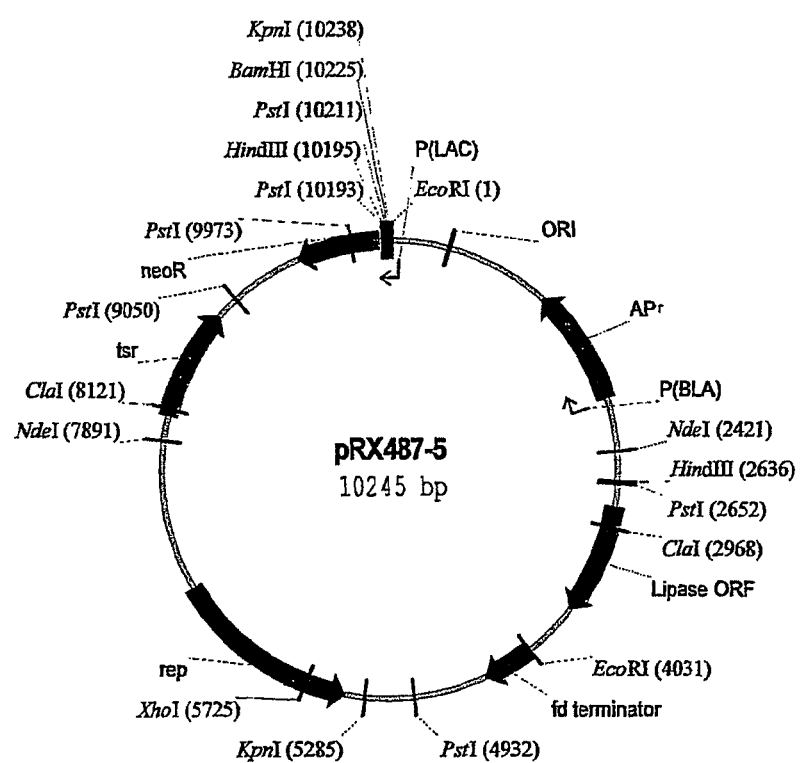
Figure 12:
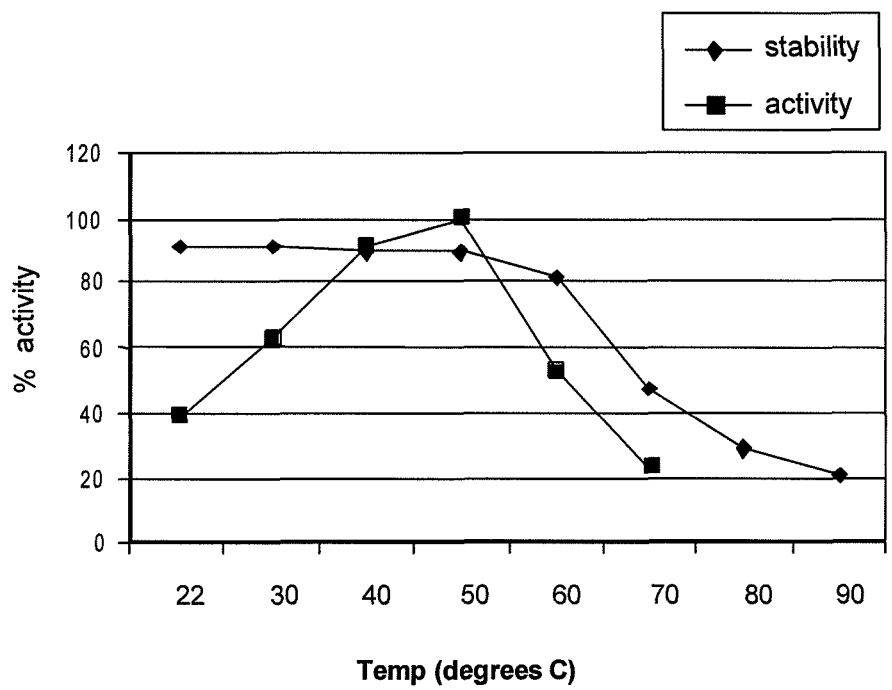
Figure 13:
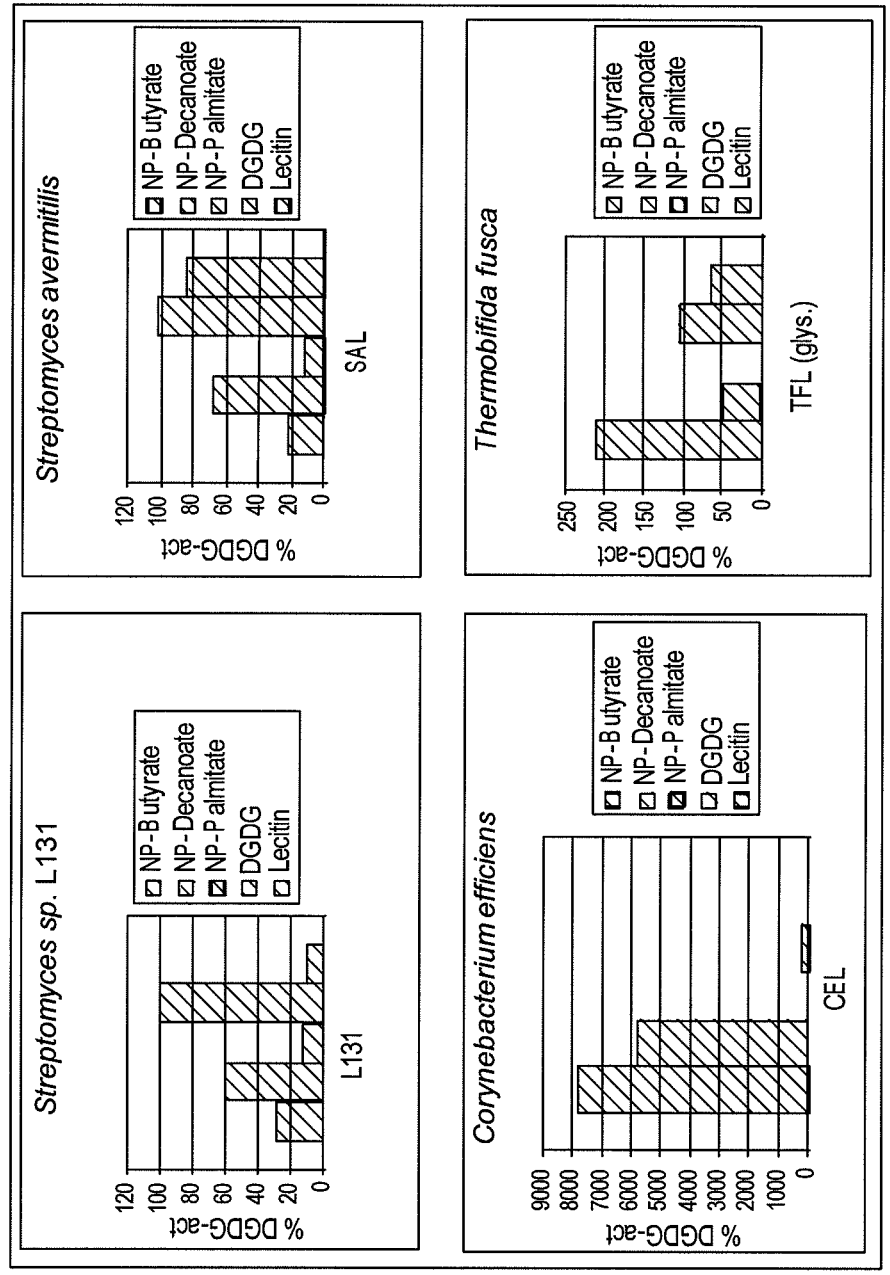

FIG. 11 shows the construction of expression vector pRX487 from pUC18(L131R) and pIJ48;

FIG. 12 shows in graphical form the effect of temperature on stability and activity of a lipolytic enzyme from *Streptomyces* sp L131;

FIG. 13 shows in graphical form the substrate specificities of galactolipases from *Streptomyces* sp L131, *Streptomyces avermitillis, Corynebacterium efficiens* and *Thermobifida fusca;*

Figure 14:
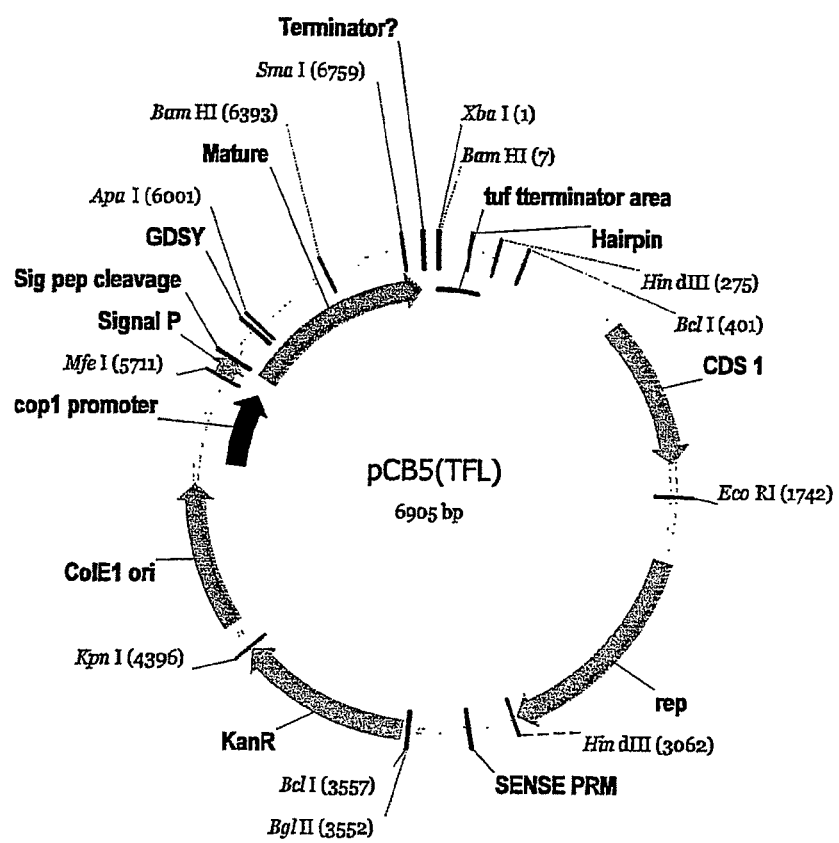

FIG. 14 shows the structure of an expression vector pCB5 (TF) for expression of *Thermobifida fusca* lipase in *C. glutamicum;*

Figure 16:
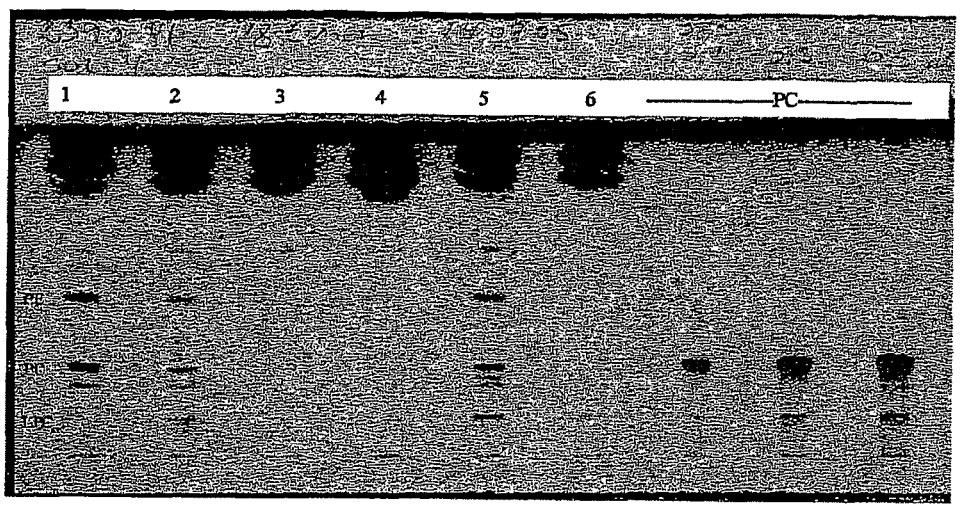
Figure 17:
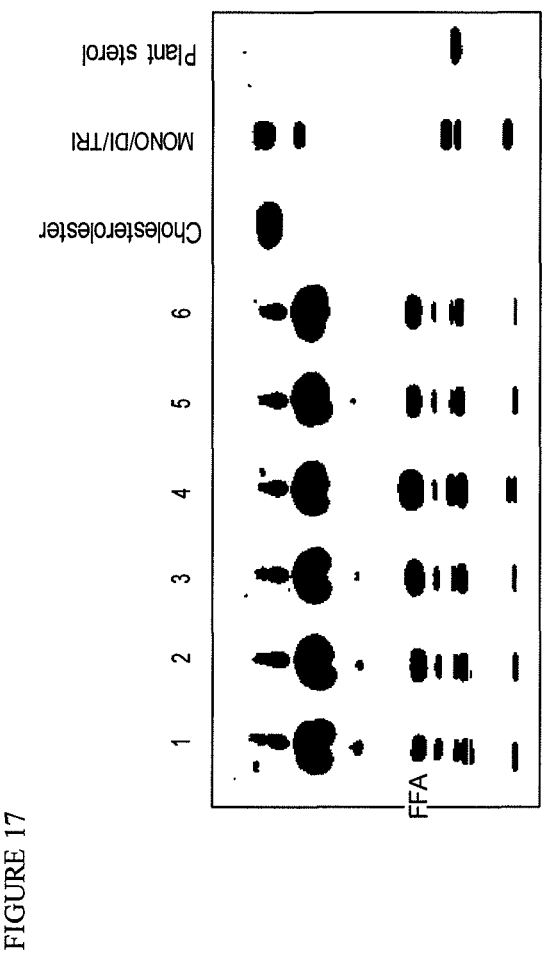

FIG. 15 shows a sequence alignment of L131 (SEQ ID NO: 4) and homologues *S. avermitilis* (SEQ ID NO: 14) and *T. fusca* (Residues 177-548 of SEQ ID NO: 5). Figure also discloses a consensus sequence disclosed as SEQ ID NO: 30);

FIG. 16 shows a HPTLC plate of reaction products from enzyme treatment of crude soya oil samples. Lane 1=control, Lane 2=99% crude oil and 1% K371 10% in water, Lane 3=98% crude oil and 2% K371 10% in water, Lane 4=97% crude oil and 3% K371 10% in water, Lane 5=99.7% crude oil and 0.3% Lecitase Ultra™ #3108 1% in water, Lane 6=99% crude oil, 0.3% Lecitase Ultra™ #3108 1% in water and 0.7% water. As reference phoshpatidylcholine (PC) is analysed; and FIG. 17 shows a HPTLC plate of reaction products from enzyme treatment of crude soya oil samples. Lane 1=control, Lane 2=99% crude oil and 1% K371 10% in water, Lane 3=98% crude oil and 2% K371 10% in water, Lane 4=97% crude oil and 3% K371 10% in water, Lane 5=99.7% crude oil and 0.3% Lecitase Ultra™ #3108 1% in water, Lane 6=99% crude oil, 0.3% Lecitase Ultra™ #3108 1% in water and 0.7% water, together with reference lanes of cholesterol ester, monoglyceride, diglyceride, triglyceride and plant sterol.

EXAMPLE 1

Identification of a Galactolipase Producing Bacterial Strain

Two microbial strains with a similar phenotype coded L130 and L131 were isolated from soil collected in Southern Finland. The 16s RNA genes of these two strains were amplified by standard PCR using oligonucleotide primers 536f (CAGCMGCCGCGGTAATWC) (SEQ ID NO: 18) and 1392r-primer (ACGGGCGGTGTGTRC) (SEQ ID NO: 19). The resulting PCR fragments were partially sequenced. SEQ ID Nos. 1 and 2 are non-enzyme encoding polynucleotides.

These sequences are ribosomal 16s RNA genes widely used for taxonomic comparisons. SEQ ID No. 1 and SEQ ID No. 2 were found 15 to have a high similarity. The sequences were then compared to the 16s RNA gene sequences in GenBank. For both isolates the highest homology (97%) was observed with the sequence of a 16s RNA gene from *Streptomyces thermosacchari* Thus, the strains were named *Streptomyces* sp. L130 and *Streptomyces* sp. L131.

EXAMPLE 2

Preparation of Lipolytic Enzyme (Galactolipase) Samples from Strains *Streptomyces* sp. L130 and L131

0.5 l of LB medium was inoculated with *Streptomyces* L130 and cultivated on a rotary shaker at 200 rpm and 30° C. for 2 days. This culture was used as inoculum for a 10 l fermentor containing the same medium. The cultivation was continued for 3 days at 30° C., 600 rpm stirring rate and 0.5 v/v aeration. The fermentation broth was cleared by centrifugation (15 min at 5000 rpm) and Triton X-100 was added to final concentration of 0.1%. The solution was concentrated using Vivaflow 200 ultrafiltration cell (Vivascience AG, Hannover, Germany) to 300 ml. The concentrate was dialysed against 10 l of 20 mM Tris HCl buffer, pH 7 containing 2 mM $CaCl_2$ and 2 mM $MgCl_2$ followed by dialysis against 0.5 l ml of 85% glycerol. The resulting preparations contained 90 U of galactolipase activity assay as defined above (GLU-7). The strain *Streptomyces* L131 was cultivated under the same conditions and its culture broth was concentrated by the same procedure. The resulting galactolipase preparation contained 70 U of activity.

EXAMPLE 3

Baking Experiments

The galactolipases from bacterial isolates L130 and L131 indicated a high activity on polar lipid substrates, galactolipids (DGDG) and phospholipids, (galactolipase and phospholipase activity), equivalent to that of a *Fusarium oxysporum* lipase (Lipopan F™ Novozymes A/S Denmark): however the galactolipase from bacterial isolates L130 and L131 (i.e. the lipolytic enzyme according to the present invention) were found to have no significant activity of triglycerides. This contrasts sharply with the activity *Fusarium oxysporum* lipase—LipopanF™.

The lipolytic enzymes from bacterial isolates L130 and L131 were prepared as described in Example 2 and were analysed for characterisation of their activity on glycolipids, phospholipids and triglycerides, both in standard assay conditions and within a dough.

Small scale baking experiments and a model dough system. Both enzymes are very active on galactolipids in flour.

Materials and Methods

Three samples of each enzyme were prepared as in Example 3. Each sample was labelled as shown in table 1:

TABLE 1

| ID | Organism | Label | GLU-7 | PLU-7 |
|---|---|---|---|---|
| 180 | *Streptomyces* spp L 130 A | Lipolytic enzyme 0.58 PLU/mL | 0.95 | 1.31 |
| 181 | *Streptomyces* spp L 130 B | Lipolytic enzyme 0.44 PLU/mL. | 0.91 | 1.31 |

TABLE 1-continued

| ID | Organism | Label | GLU-7 | PLU-7 |
|---|---|---|---|---|
| 182 | *Streptomyces* spp L 130 C | Lipolytic enzyme 1.8 PLU/mL. | 1.21 | 1.53 |
| 183 | *Streptomyces* spp L 131 A | Lipolytic enzyme 0.54 PLU/mL. | 0.63 | 1.29 |
| 184 | *Streptomyces* spp L 131 B | Lipolytic enzyme 0.64 PLU/mL. | 0.84 | 1.16 |
| 185 | *Streptomyces* spp L 131 C | Lipolytic enzyme 0.85 PLU/mL. | 1.35 | 1.17 |

The phospholipase and galactolipase activity of the enzymes were assessed using the phospholipase activity assay (PLU-7) and the galactolipase activity assay (GLU-7) mentioned herein above.

Dough Slurry Experiment 0.8 gram Wheat flour was scaled in a 12 ml centrifuge tube with lid. 1.5 ml water containing the enzyme was added. The sample was mixed on a Whirley and placed in a heating cabinet at 30° C. for 60 minutes. 6 ml n-Butanol:Ethanol 9:1 was added, and the sample was mixed again until the flour was finely distributed in the solvent. The tubes were the placed in a water bath at 95° C. for 10 minutes. Then mixed again and placed on a rotation device 45 rpm, for 45 minutes.

The sample was then centrifuged at 2000 g for 10 minutes. And 2 ml supernatant was transferred to a 10 ml dram glass. The solvent was evaporated at 70° C. under a steam of nitrogen.

The isolated lipids are analysed by GLC.

Gas Chromatography

Perkin Elmer 8420 Capillary Gas Chromatography equipped with WCOT fused silica column 12.5 m×0.25 mm ID×0.1 μm 5% phenyl-methyl-silicone (CP Sil 8 CB from Crompack).

| Carrier: Helium. Injection: 1.5 μL with split. Detector: FID. 385° C. | | | | |
|---|---|---|---|---|
| Oven program: | 1 | 2 | 3 | 4 |
| Oven temperature [° C.] | 80 | 200 | 240 | 360 |
| Isothermal, time [min] | 2 | 0 | 0 | 10 |
| Temperature rate [° C./min] | 20 | 10 | 12 | |

Sample preparation: Lipid extracted from 0.2 gram flour was dissolved in 2 mL heptane:pyridine 2:1 containing an internal standard heptadecane, 2 mg/mL. 500 μL of the sample was transferred to a crimp vial. 100 μL MSTFA (N-Methyl-N-trimethylsilyl-trifluoracetamid) was added and the reaction incubated for 15 minutes at 90° C.

Calculation: Response factors for monoglycerides, diglycerides, triglycerides, free fatty acid and galactolipids were determined from reference mixtures of these components. Based on these response factors the lipids in the dough were calculated.

Results.

The samples of enzyme from *Streptomyces* were analyzed for phospholipase and galactolipase activity with results shown in table 2. The activity ratio PLU-7/GLU-7 was also calculated. The mean ratio for the samples was 1.4, but with some deviation in some of the samples, which might be explained by analytical deviations.

TABLE 2

| Sample ID | Organism | GLU-7 | PLU-7 | Ratio PLU-7/GLU-7 |
|---|---|---|---|---|
| 180 | L 130 A | 0.95 | 1.31 | 1.4 |
| 181 | L 130 B | 0.91 | 1.31 | 1.4 |
| 182 | L 130 C | 1.21 | 1.53 | 1.3 |
| 183 | L 131 A | 0.63 | 1.29 | 2.0 |
| 184 | L 131 B | 0.84 | 1.16 | 1.4 |
| 185 | L 131 C | 1.35 | 1.17 | 0.9 |

Dough Experiment.

The activity of the enzyme on wheat lipids was tested in the dough slurry experiment as mentioned under materials and Methods. The isolated lipids from the dough were analysed by GLC as shown in table 3

TABLE 3

GLC analysis of dough lipids (% based on flour weight).

| Sample ID | Enzyme dosage PLU/g flour | FFA | MGMG | DGMG | MGDG | DGDG | TRI |
|---|---|---|---|---|---|---|---|
| 185 | 0.105 | 0.1642 | 0.0042 | 0.0380 | 0.0345 | 0.1520 | 0.5515 |
| 185 | 0.263 | 0.1687 | 0.0130 | 0.0670 | 0.0239 | 0.0941 | 0.5470 |
| 185 | 0.526 | 0.2096 | 0.0121 | 0.0664 | 0.0158 | 0.0617 | 0.5460 |
| 185 | 1.05 | 0.2597 | 0.0036 | 0.0546 | 0.0068 | 0.0303 | 0.5301 |
| 182 | 0.097 | 0.1542 | 0.0051 | 0.0563 | 0.0313 | 0.1148 | 0.5475 |
| 182 | 0.244 | 0.1687 | 0.0159 | 0.0785 | 0.0200 | 0.0566 | 0.5280 |
| 182 | 0.488 | 0.2095 | 0.0055 | 0.0646 | 0.0098 | 0.0219 | 0.5418 |
| 182 | 0.976 | 0.2581 | 0.0092 | 0.0439 | 0.0043 | 0.0045 | 0.5579 |
| Control | 0 | 0.1529 | 0.0006 | 0.0188 | 0.0440 | 0.1443 | 0.5054 |
| Lipopan F™ | 1.47 | 0.23 | 0.03 | 0.10 | 0.01 | 0.07 | 0.44 |

FFA = free fatty acids. MGMG = monogalactosylmonoglyceride. DGMG = digalactosyldiglyceride. MGDG = monogalactosyldiglyceride. DGDG = digalactosyldiglyceride. TRI = triglyceride.

Figure 6:
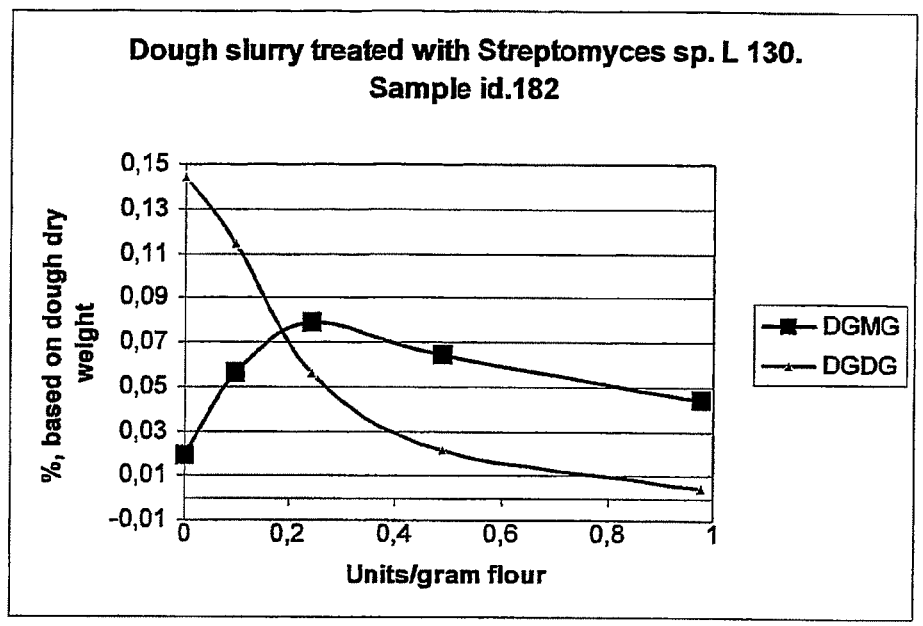
FIG. 6 shows a graph of the effect of a lipolytic enzyme from *Streptomyces* sp. L130 on digalactosyldiglyceride in dough.
Figure 7:
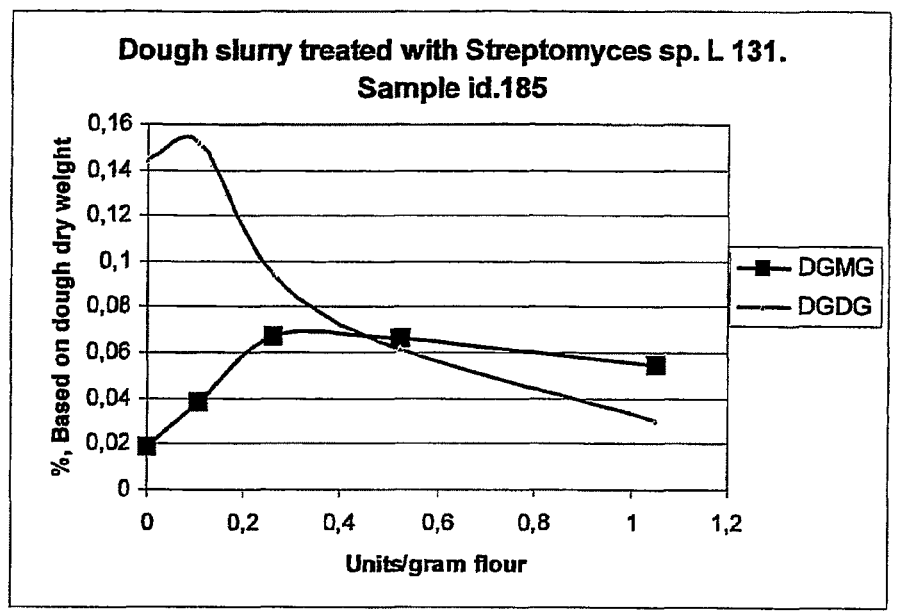
FIG. 7 shows in graphical form the effect of a lipolytic enzyme from *Streptomyces* sp. L131 on digalactosyldiglyceride in dough.

The results from table 3 and table 4 confirm that the enzymes isolated in the supernatant from fermentation of Streptomyces sp L130 and L131 are very active on galactolipids in a dough. The diesters DGDG and MGDG are hydrolyzed to the corresponding monoesters DGMG and MGMG. The results are also illustrated graphically in FIGS. 6 and 7. These results confirm that both enzymes are very active at low dosage 0-0.2 Units/g flour and corresponding amount of monoester is produced. At higher dosage 0.4-1 Units/gram flour DGDG is further degraded but also some hydrolysis of the monoesters are observed. This may indicate the enzymes are not specific to the position of the fatty acid in the galactolipid molecule.

Figure 8:
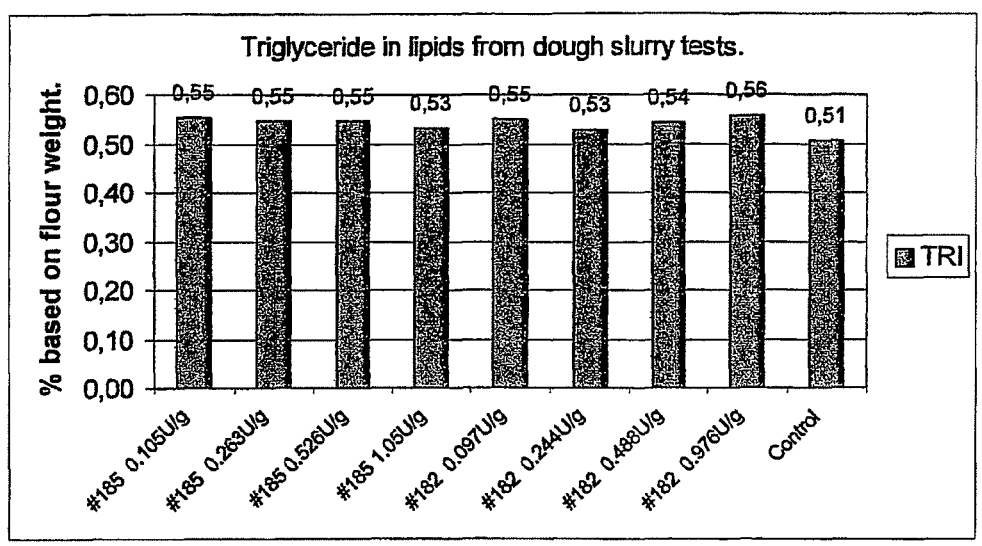
FIG. 8 shows in graphical form the effect of a lipolytic enzyme from *Streptomyces* on triglyceride in dough.

The activity of the enzymes on triglyceride, as illustrated in FIG. 8, is almost not existent. It is therefore concluded that the enzymes tested have no significant effect on triglyceride. This is also in agreement with some experiments conducted on tributyrin as substrate, where no activity was observed.

Summary

A lipolytic enzyme was isolated in the supernatant from fermentation of Streptomyces sp.

The lipolytic enzyme was found to have both phospholipase and galactolipase activity, but no significant activity on triglycerides. The ratio of phospholipase:galactolipase activity was approx. 1.4 for the samples tested.

Dough slurry experiments confirms that the enzymes were active on galactolipids in the flour. The enzymes were active in dough at a very low dosage 0-0.2 Units/g flour. Commercial phospholipases like Lipopan F™ (Novozymes A/S, Denmark) need to be dosed in 3-4 times higher dosage in order to obtain the same effect on galactolipids. The dough slurry experiments also confirmed that the enzymes from Streptomyces sp. had no measurable activity on triglycerides.

EXAMPLE 4

Cloning of the Lipolytic Enzyme Gene from Streptomyces sp. L131

The chromosomal DNA was isolated from Streptomyces sp. L131 using a modification of a standard method. Bacteria were grown on a rotary shaker in LB medium at 30° C. and high aeration (100 ml of medium per 0.51 baffled flask, 200 rpm) to early stationary phase. From 500 ml bacterial culture cells were collected with centrifugation and washed once with lysis buffer (550 mM glucose, 100 mM Tris, 2 mM EDTA, pH 8.0).

Cell pellet was re-suspended in 10 ml of lysis buffer and lysozyme was added to 1 mg/ml. Cells were incubated at 37° C. for at least 15 min. The progress of lysozyme digestion was followed by transferring aliquots of bacterial suspension into 1% SDS solution and measuring the absorption of the resulting mixture at 600 nm. The amount of lysozyme and incubation time were adjusted so that at least 70-90% of all cells were lysed as evidenced by the decrease in $A_{600}$. At this point of time, SDS was added to the bacterial suspension to 1% and proteinase K to 0.1 mg/ml. The suspension was incubated at 56° C. for 30 min followed by extractions with phenol and chloroform. After chloroform extraction, DNA was precipitated with sodium acetate (0.5M final concentration) and isopropanol (0.6 vol/vol) and the DNA pellet was washed with 70% ethanol, dried in vacuum and dissolved in TE buffer (10 mM Tris, 1 mM EDTA) containing RNAse A (0.01 mg/ml).

The DNA was partially digested with restriction endonuclease Sau3A and the hydrolysates fractionated on a 0.8% agarose gel. The 3-10 kb fraction of the Sau3A was isolated from agarose gels by electroelution. This DNA preparation was used to construct a gene library using Stratagene's (LaJolla, USA) ZAP Express/Predigested Vector/Gigapack Cloning Kit (product #239615). Ligation, packaging, amplification of library and its conversion to the phagemid form were carried out according to the protocols provided by Stratagene. Plasmid form of the resulting gene library was screened on indicator plates prepared as follows. 80 ml of sterile LB agar containing 25 mg/l of kanamycin was placed into each 15 cm Petri dish and allowed to solidify. Subsequently, 10 ml top agar layer was added containing 0.5% DGDG and 0.0005% Safranine O. The gene library was plated at a density of approximately 5000 colonies per 15 cm plate. The plates were incubated at 37° C. for 24 h followed by a four-day incubation at room temperature. A clone forming red halo on indicator plate was selected from the library and purified by cloning on a new indicator plate.

The plasmid isolated from this clone (named pBK(L131)) was used to re-transform E. coli strain XL1-Blue MRF' to kanamycin resistance. All such transformants displayed galactolipase-positive phenotype. pBK(L131) contained an approximately 7.5 kb insert. This insert was sequenced. One sequenced region (SEQ ID No. 3) was found to contain an open reading frame encoding a protein (SEQ ID No. 4) showing homology to a known lipase from Streptomyces rimosus. This lipase, a member of so-called GDSX (SEQ ID NO: 31) family of lipases/esterases/acyl transferases is only known to be able to hydrolyse neutral lipids and artificial lipase substrates.

A series of deletions and sub-clones of the original insert were constructed and tested for galactolipase activity. It was found that a deletion derivative carrying 3 kb EcoRI—SacI fragment of the original insert still retains full DGDGse activity. This data correlated well with the results of partial DNA. One area demonstrated homology to known lipases. This area was subsequently sequenced completely. Comparison of this sequence with the GenBank revealed that the closest homologue (58.5%) of the L131 galactolipase that has been biochemically characterised is a lipase from *S. rimosus*, and identified as a lipid:acyl transferase in WO04/064987 and WO04/064537.

Expression of L131 Galactolipase in *E. coli*.

The standard pET-system, in which the gene is under control of the T7 phage promoter, was used in to express the L131 galactolipase in *E. coli*.

Expression of L131 Galactolipase in *Streptomyces lividans*.

The shuttle vector pRX487-5 (FIG. 11) (derived from pIJ4987: Kieser T. et al Practical *Streptomyces* genetics. The John Innes Foundation, Crowes, Norwich, England (2000)) used for expression of L131 galactolipase in *S. lividans* combines *E. coli* plasmid pUC18 and the *S. lividans* plasmid IJ487. In pRX487-5, the lac promoter of pUC18 is placed upstream of promoter-less kanamycin phosphotransferase gene of pIJ487. Indeed, the plasmid transformed *E. coli* not only to ampicillin but also to at least a low level (5 mg/l) of kanamycin resistance. The vector contains unmodified EcoRI-XbaI fragment of the chromosomal DNA of *S. thermosacchari* comprising the complete coding sequence of the galactolipase gene, about 160 bp of upstream non-coding sequence and 420 bp of downstream non-coding sequence. All transformants displayed similar levels of galactolipase activity as judged by the halo formation on indicator plates. Similarly, when *S. lividans* carrying pRX487-5 was cultivated at 10 l level and the resulting culture was cloned on indicator plates, all clones appeared to produce equal amounts of galactolipase activity. In small shake-flask cultures inoculated by vegetative cells directly from plates, the transformants typically produced about 10-20 mU/ml of galactolipase activity after 3 days of cultivation. When shake-flask cultures were inoculated with spores of the recombinant *S. lvividans*, higher galactolipase activities were measured (about 30 mU/ml), correlating with higher biomass accumulation. In an experiment where *S. lividans* carrying pRX487-5 was grown in fermentor under high aeration conditions and fed-batch mode (see material and methods for details) biomass accumulation reached 170 g/l (wet weight). Accordingly, much higher galactolipase activity—about 1 U/ml was detected.

Biochemical Properties of L131.

Figure 9:
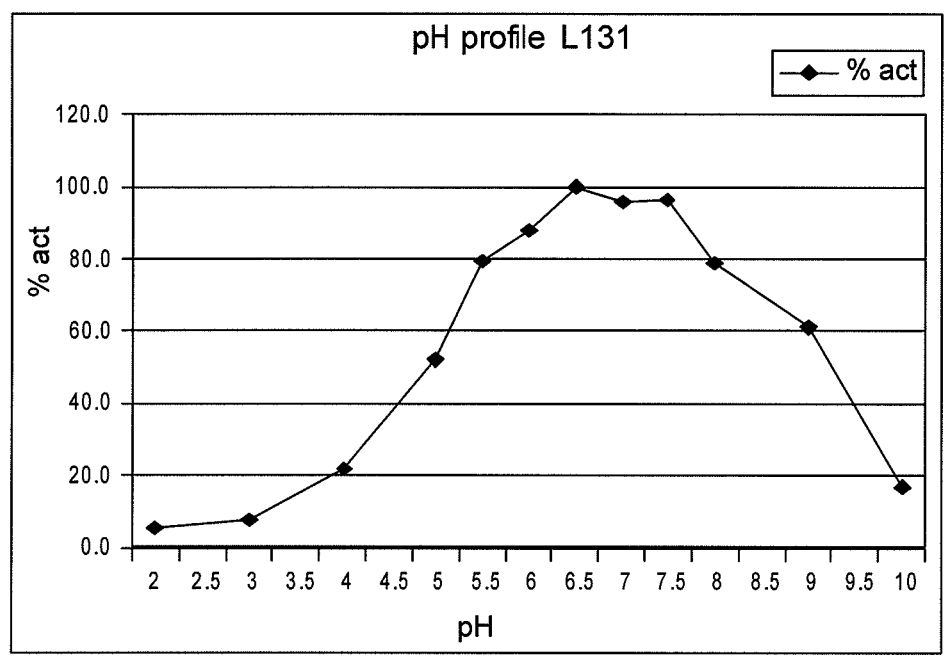
FIG. 9 shows the pH profile of the lipolytic enzyme obtained from *Streptomyces* sp. L131 on galactolipid substrate.

Some biochemical properties of L131 were tested. The pH optimum of the enzyme was found to be around 6.5-7.5 (FIG. 9). The enzyme exhibited maximum activity towards DGDG at a temperature ~50° C. Above this temperature inactivation occurred, but not sharply, and after 20 min incubation in 90° C., ~10% of residual activity was detected (FIG. 12).

EXAMPLE 5

Expression of *Streptomyces* L131 Lipolytic Enzyme According to the Present Invention Gene in *E. coli*

The open reading frame of pBK(L131) encoding presumptive lipolytic enzyme according to the present invention was amplified by PCR using primers oL131-5 (GGTGAATT'CATGAGATTGACCCGATCCCTGTCGG, sense primer) (SEQ ID NO: 20) and oL131-3 (ACTTCTA-GAGCGGCGCCACCGTGACGTACA, anti-sense primer) (SEQ ID NO: 21). The amplified DNA fragment was digested with EcoRI and XbaI and cloned into a *B. subtilis-E. coli* shuttle vector pGTK44. This vector has been constructed by substituting the SalI-EcoRI fragment of plasmid pGTK44 (Povelainen et al., Biochem J. 371, 191-197 (2003)) containing degQ36 promoter with EcoRI-SalI fragment of pGT44 (Kerovuo J. et al. Biotechnology Letters 22, 1311-1317 (2000)).

Figure 5:
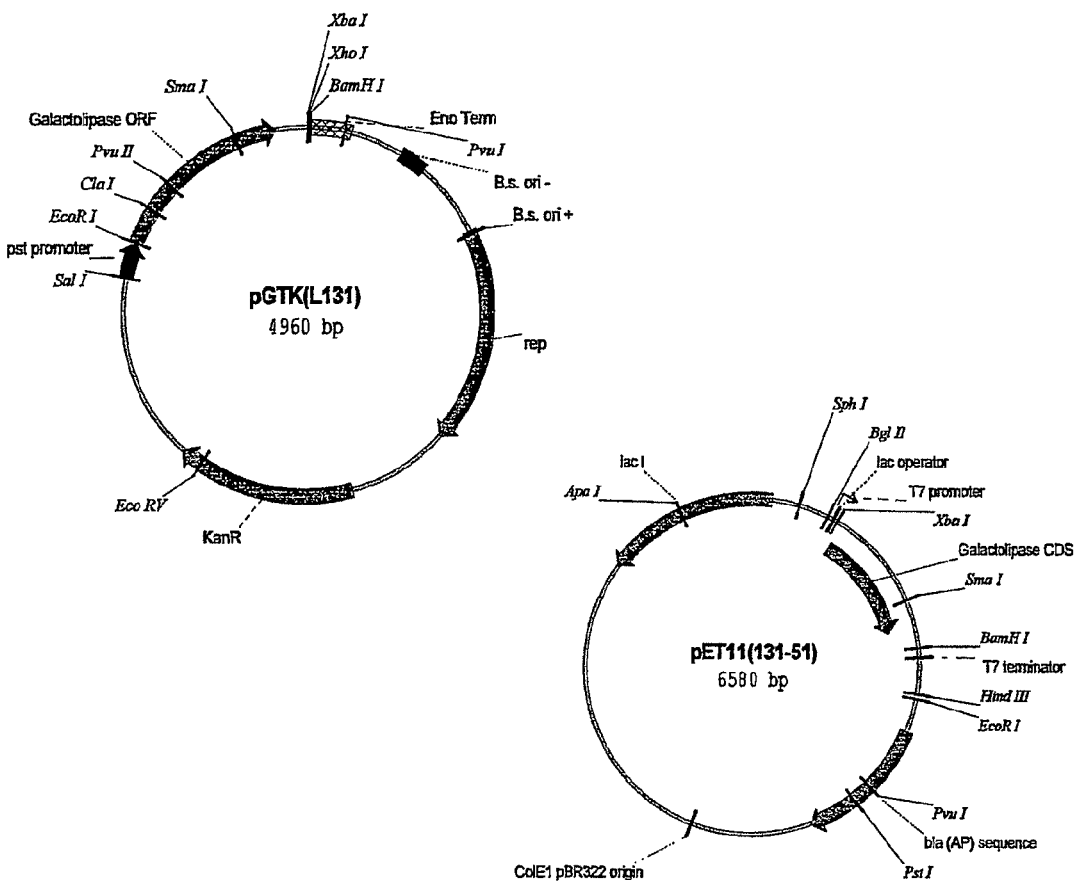
FIG. 5 shows the structure of the lipolytic enzyme expression vectors pGTK(L131) and pET11(131-51)

Galactolipase activity was detected in *E. coli* transformed with the resulting plasmid pGTK44(L131) (FIG. 5) using indicator plates. Control transformants (containing parent plasmid pGTK44) were galactolipase-negative. Thus, protein sequence represented by SEQ ID No 4 indeed possesses galactolipase activity. The same pair of primers amplified a fragment of the same size (by agarose gel electrophoresis) with chromosomal DNA of *Streptomyces* sp. L130 further confirming earlier observations about close similarity of the two isolated strains and their galactolipase genes.

For expression in *E. coli* under control of the T7 phage promoter, the deduced galactolipase coding region was amplified by PCR using chromosomal DNA of the *Streptomyces* sp. L131 as template and the two oligonucleotide primers (oL131-51 GGTCATGCTAGCATGAGATTGAC-CCGATCCCTGTCGG (SEQ ID NO: 22) and oL131-31 GCATGGATCCGCGGCGCCACCGTGACGTACA) (SEQ ID NO: 23). The PCR product was digested with NheI and BamHI and ligated with pET11a (Novagen, USA) vector digested with the same restriction endonucleases. The ligation mixture was used to transform the *E. coli* strain XL-Blue1 MRF' and 12 different plasmid clones with restriction patterns corresponding to the structure of pET11(131-51) (FIG. 4) were isolated. Each plasmid clone was used to separately transform the *E. coli* strain BL21(DE3) and the resulting transformants were grown on LB-ampicilin containing galactolipase activity indicator layer (Example 4). Most clones did express active galactolipase. One clone (pET11 (131-51)-12) was selected as a source of recombinant galactolipase for subsequent characterisation.

The enzyme expressed in *E. coli* (labelled #236) was analysed and found to have: 0.33 GLU/ml and 0.36 PLU/ml, when analysed using the GLU-7 assay and PLU-7 assay taught herein.

In liquid culture *E. coli* BL21(DE3) expressed about 2 mU/ml of galactolipase activity after 40 h cultivation in LB-ampicillin broth (37° C., 200 rpm shaking). Essentially all of the activity was found in the culture broth. No galactolipase activity was detected in *E. coli* BL21(DE3) transformed with pET11a (Novagen, USA) and cultivated under the same conditions.

About four liters of galactolipase-containing culture broth culture was concentrated on a rotary evaporator to about 300 ml and dialysed against 15 l of 20 mM Tris HCl buffer, pH 7 containing 2 mM $CaCl_2$ and 2 mM $MgCl_2$. The dialysed material was again concentrated on a rotary evaporator to about 30 ml and dialysed against 2 l of 50% glycerol. The resulting preparation (18 ml) contained about 100 mU/ml of galactolipase activity.

The enzyme expressed in *E. coli* (labelled #236) was also tested in dough. High activity on galactolipids was observed in dough as can be seen from FIG. 10, which shows a TLC plate.

EXAMPLE 6

Expression of the Lipolytic Enzyme According to the Present Invention Gene from *Streptomyces* sp. L131 in Different Hosts Construction of the vector pGTK44(L131) has been outlined in the Example 5. Besides *E. coli*, this vector can be used to produce *Streptomyces* L131 lipolytic enzyme according to the present invention in *Bacillus*. Using this vector is only one of many possible ways to express the L131 lipolytic enzyme according to the present invention in *Bacillus*. For example, the pst promoter employed in pGTK44(L131) may be replaced by any other strong constitutive or regulated promoter active in *Bacillus*. Many such promoters are known in the art. For example, degQ36 promoter (Yang M et al. J. Bacteriol. 166, 113-119 (1986)), cdd promoter, also known as p43 (Wang P Z, Doi R H. J. Biol. Chem. 259, 8619-8625 (1984), amylase or neutral protease promoters etc. In addition to pGTK44(L131) and other *Bacillus* vectors based on pTZ12 replicon (Aoki T. et al., Mol. Gen. Genet. 208, 348-352 (1987)) any other plasmid vector (e.g pUB110, Gryczan T J et al. J. Bacteriol. 134, 318-29 (1978) and its derivatives) can be used.

Other preferred hosts for expression of the *Streptomyces* L131 lipolytic enzyme according to the present invention gene are high-GC Gram positive bacteria, in particular, *Streptomyces*, (for example, *S. lividans, S. coelicolor, S. griseus, S. natalensis, S. rubiginosus, S. olivaceus, S. olivochromogenes, S. violaceoruber*), In such hosts, the lipolytic enzyme according to the present invention gene can be introduced under its own promoter on a multi-copy vector (e.g. using pIJ110 derivatives such as pIJ486, Ward et al. Mol. Gen. Genet. 203, 468-478 (1986)) or placed under control of a strong *Streptomyces* promoter, for example ermE* (Schmitt-John T, Engels J W. Appl. Microbiol. Biotechnol. 36, 493-498 (1992)) or thiostreptone-inducinbe tipA promoter (Kieser T et al. in Practical *Streptomyces* Genetics, p. 386, The John Innes Foundation, Norwich UK (2000)).

In addition to prokaryotic hosts, L131 lipolytic enzyme gene may be expressed in one of the many suitable fungal species. In particular, yeasts such as *Saccharomyces cerevisiae, Schizosaccharomyces pombe, Pichia pastoris, Hansenula polymorpha* are suitable. In yeast, the lipolytic enzyme gene may be placed under control of any of the known strong yeast promoters, such glycolytic promoters (PGK, GDH, ENO etc) phosphate starvation induced promoters such as PHO5, the promoters of ethanol/methanol metabolism such as ADH1 promoter in *S. cerevisiae* or methanol-inducible promoters in *H. polymorpha* or *P. pastoris*.

When expressing the lipolytic enzyme gene in any host, construction of a synthetic or semi-synthetic gene encoding the sequence of SEQ ID 4 would be advantageous. Likewise, partly or completely synthetic genes may be designed based on sequences available through homology searches in silico as explained in Example 4. Such sequences, may incorporate a number of useful features that are absent in wild-type lipolytic enzyme genes. For, example, the codon bias can be corrected to better correspond codon preferences of the expression hosts. One special case of codon bias correction useful for all hosts is to convert the GTG initiation codon of SEQ ID No 3 into ATG. Another typical modification obvious for a man skilled in the art is to exchange the native *Streptomyces* signal sequence of the L131 lipolytic enzyme with a signal sequence native to or known to be functional in the chosen expression host.

Previous examples of useful expression systems for L131 lipolytic enzyme focused on using plasmid vectors for the introduction of the lipolytic enzyme gene into the expression host. This is indeed the preferred mode to implement current invention. However, an alternative approach of integrating the expression cassette (including promoter, lipolytic enzyme gene coding region and an optional transcription terminator) into a chromosome is also feasible. In particular, multi-copy integration of the expression cassette into the host chromosome would be efficient.

The recombinant hosts expressing the lipolytic enzyme gene can be, advantageously, mutated to reduce the level of protease activity in the culture broth. The cultivation of any of such recombinant hosts can be carried out in the presence of compounds stabilising the enzyme. Such compounds may be various proteins (e.g. casein, peptone of serum albumin) or different lipids, lysolipids or detergents (e.g. galactolipids, mono- and diacylglycerols or Triton X-100).

EXAMPLE 7

Acyl-Transferase Activity of *Streptomyces* L131 Lipolytic Enzyme and its Derivatives Some lipases may also possess acyl-transferase activity. In particular, some members of the GDSX (SEQ ID NO: 31) family, for example, *Aeromonas hydrophila* acyltransferase (P10480) (taught in copending International Application No. PCT/IB2004/000655) have high acyl-transferase activity. Thus, *Streptomyces* L131 lipolytic enzyme may be predicted to have also the acyl-transferase activity as well. This activity can be further enhanced through random mutagenesis/directed evolution. Moreover, since *A. hydrophila* acyl-transferase and *Streptomyces* L131 lipolytic enzyme share the same overall protein fold, combining the substrate specificity of *Streptomyces* L131 lipolytic enzyme with high transferase efficiency of the *Aeromonas* enzyme is possible. This combination may be achieved through the known techniques of targeted mutagenesis/protein design or by gene shuffling.

EXAMPLE 8

Identification of Alternative Lipolytic Enzymes from Other *Streptomyces* Species The GDSX (SEQ ID NO: 31) family of esterase's (Upton C, Buckley J T. Trends Biochem. Sic. 20, 178-179 (1995), pfam00657.11) is a group of esterases/lipases/acyl transferases sharing a specific sequence motif around the active site serine (GDSX (SEQ ID NO: 31) where X is a hydrophobic amino acid residue). This group of enzymes is also known as lipase family 11 (Arpigny J L, Jaeger K-E. Biochem. J. 343, 177-183 (1999)). Although this family includes many different types of esterases, lipases and acyl-transferases, the lipolytic enzyme according to the present invention is a GDSX (SEQ ID NO: 31) enzyme.

Thus, the sequences taught in the present invention of the *Streptomyces* sp. L131 lipolytic enzyme (galactolipase) can be used in silico to identify other galactolipases from other species of *Streptomyces*.

To determine if a protein has the GDSX (SEQ ID NO: 31) motif according to the present invention, the sequence is preferably compared with the hidden markov model profiles (HMM profiles) of the pfam database.

Pfam is a database of protein domain families. Pfam contains curated multiple sequence alignments for each family as well as profile hidden Markov models (profile HMMs) for identifying these domains in new sequences. An introduction to Pfam can be found in Bateman A et al. (2002) Nucleic Acids Res. 30; 276-280. Hidden Markov models are used in a number of databases that aim at classifying proteins, for review see Bateman A and Haft D H (2002) Brief Bioinform 3; 236-245.

For a detailed explanation of hidden Markov models and how they are applied in the Pfam database see Durbin R, Eddy S, and Krogh A (1998) Biological sequence analysis; probabilistic models of proteins and nucleic acids. Cambridge University Press, ISBN 0-521-62041-4. The Hammer software package can be obtained from Washington University, St Louis, USA.

Alternatively, the GDSX (SEQ ID NO: 31) motif can be identified using the Hammer software package, the instructions are provided in Durbin R, Eddy S, and Krogh A (1998) Biological sequence analysis; probabilistic models of proteins and nucleic acids. Cambridge University Press, ISBN 0-521-62041-4 and the references therein, and the HMMER2 profile provided within this specification.

The PFAM database can be accessed, for example, through several servers which are currently located at websites maintained by the Sanger Institute (UK) in conjunction with Wellcome Trust Institute, the Institut National de la Recherche Agronomique, and the Center for Genomics and Bioinformatics of the Karolinska Institutet, among others.

The database offers a search facility where one can enter a protein sequence. Using the default parameters of the database the protein sequence will then be analysed for the presence of Pfam domains. The GDSX (SEQ ID NO: 31) domain is an established domain in the database and as such its presence in any query sequence will be recognised. The database will return the alignment of the Pfam00657 consensus sequence to the query sequence.

Preferably when aligned with the Pfam00657 consensus sequence the lipolytic enzyme for use in the compositions/methods of the invention have at least one, preferably more than one, preferably more than two, of the following, a GDSx (SEQ ID NO: 31) block, a GANDY (SEQ ID NO: 35) block, a HPT block. Suitably, the lipolytic enzyme may have a GDSx (SEQ ID NO: 31) block and a GANDY (SEQ ID NO: 35) block. Alternatively, the enzyme may have a GDSx (SEQ ID NO: 31) block and a HPT block. Preferably the enzyme comprises at least a GDSx (SEQ ID NO: 31) block.

The pfam00657 GDSX (SEQ ID NO: 31) domain is a unique identifier which distinguishes proteins possessing this domain from other enzymes.

In addition or as an alternative thereto, alternative lipolytic enzymes from other *Streptomyces* species can be identified by conducting a sequence identity comparison and/or hybridisation with one or more of the PCR sequence fragments shown as SEQ ID No. 1 or SEQ ID No. 2. Suitably, the comparisons may be carried out with fragments comprising over 15 nucleotides of SEQ ID No. 1 or SEQ ID No. 2, preferably with fragments comprising over 20 nucleotides of SEQ ID No. 1 or SEQ ID No. 2. Suitably, the complete sequences shown as SEQ ID No. 1 or SEQ ID No. 2 could be used. Preferably, the hybridisation is carried out at high or very high stringency conditions. Nucleotide sequences having at least 80%, preferably at least 85%, at least 90%, at least 95%, at least 97%, at least 98% or at least 99% identity to SEQ ID No. 1 or SEQ ID No. 2 indicate strains of *Streptomyces* which may be sources of the lipolytic enzyme, i.e. the galactolipase, according to the present invention.

EXAMPLE 9

Identification of Galactolipases for Use in the Methods and Uses of the Present Application As mentioned above, the sequence of the novel *Streptomyces thermosacchari* L131 offers for the possibility for in silico identification of new family II galactolipases. In this regard, one particular region which may be of particular interest is the GDSX (SEQ ID NO: 31) motif.

The GDSX (SEQ ID NO: 31) motif is comprised of four conserved amino acids. Preferably, the serine within the motif is a catalytic serine of the lipid acyltransferase enzyme. Suitably, the serine of the GDSX (SEQ ID NO: 31) motif may be in a position corresponding to Ser-16 in *Aeromonas hydrophila* lipolytic enzyme taught in Brumlik & Buckley (Journal of Bacteriology April 1996, Vol. 178, No. 7, p 2060-2064).

To determine if a protein has the GDSX (SEQ ID NO: 31) motif, the sequence is preferably compared with the hidden markov model profiles (HMM profiles) of the pfam database. As mentioned in Example 8, pfam is a database of protein domain families. Thus, the pfam database may also be used to identify suitable enzymes from genera other than *Streptomyces*.

Alternatively, the GDSX (SEQ ID NO: 31) motif can be identified using the Hammer software package, the instructions are provided in Durbin R, Eddy S, and Krogh A (1998) Biological sequence analysis; probabilistic models of proteins and nucleic acids. Cambridge University Press, ISBN 0-521-62041-4 and the references therein, and the HMMER2 profile provided within this specification.

Preferably, the lipolytic enzyme in accordance with the present invention comprises the GDSX (SEQ ID NO: 31) motif.

When aligned to either the pfam Pfam00657 consensus sequence (as described in WO04/064987) and/or the L131 sequence herein disclosed (SEQ ID No 4)

i) The galactolipase/lipid acyl-transferase enzyme enzyme of the invention, or for use in methods of the invention, has preferably a GDSx (SEQ ID NO: 31) motif, more preferably a GDSY (SEQ ID NO: 34) motif.

and/or ii) The galactolipase/lipid acyl-transferase enzyme enzyme of the invention, or for use in methods of the invention, has preferably a GANDY (SEQ ID NO: 35) block, more preferably a GANDY (SEQ ID NO: 35) block comprising amino GGNDx (SEQ ID NO: 36), more preferably GGNDA (SEQ ID NO: 37) or GGNDL (SEQ ID NO: 38).

and/or iii) The enzyme of the invention, or for use in methods of the invention, has preferable an HPT block.

and preferably iv) The galactolipase/lipid acyl-transferase enzyme of the invention, or for use in methods of the invention, has preferably a GDSY motif and a GANDY block comprising amino GGNDx, preferably GGNDA or GGNDL, and a HPT block (conserved histadine).

In this regard, the inventors identified a homologous sequence to *Streptomyces* L131 which did not comprise a GDSX (SEQ ID NO: 31) motif: namely *Novosphingobium aromaticivorans* (NAL)

Novosphingobium\aromaticivorans\ GDSx (SEQ ID NO: 31) 284 aa

SEQ ID No. 10

ZP_00094165
```
  1 mgqvklfarr capvllalag lapaatvare aplaegaryv algssfaagp gvgpnapgsp
 61 ercgrgtlny phllaealkl dlvdatcsga tthhvlgpwn evppqidsvn gdtrlvtlti
121 ggndvsfvgn ifaaacekma spdprcgkwr eiteeewqad eermrsivrq iharaplarv
181 vvvdyitvlp psgtcaamai spdrlaqsrs aakrlarita rvareegasl lkfshisrrh
241 hpcsakpwsn glsapaddgi pvhpnrlgha eaaaalvklv klmk
```
/

SEQ ID No. 11
```
   1 tgccggaact caagcggcgt ctagccgaac tcatgcccga aagcgcgtgg cactatcccg
  61 aagaccaggt ctcggacgcc agcgagcgcc tgatggccgc cgaaatcacg cgcgaacagc
 121 tctaccgcca gctccacgac gagctgccct atgacagtac cgtacgtccc gagaagtacc
 181 tccatcgcaa ggacggttcg atcgaatcc ccagcagat cgtgattgcc cgcgagacac
 241 agcgtccgat cgtgctgggc aagggtggcg cgaagatcaa ggcgatcgga gaggccgcac
 301 gcaaggaact ttcgcaattg ctcgacacca aggtgcacct gttcctgcat gtgaaggtcg
 361 acgagcgctg ggccgacgcc aaggaaatct acgaggaaat cggcctcgaa tgggtcaagt
 421 gaagctcttc gcgcgccgct gcgccccagt acttctcgcc cttgccgggc tggctccggc
 481 ggctacggtc gcgcgggaag caccgctggc cgaaggcgcg cgttacgttg cgctgggaag
 541 ctccttcgcc gcaggtccgg gcgtggggcc caacgcgccc ggatcgcccg aacgctgcgg
 601 ccggggcacg ctcaactacc cgcacctgct cgccgaggcg ctcaagctcg atctcgtcga
 661 tgcgacctgc agcggcgca cgaccacca cgtgctgggc ccctggaacg aggttccccc
 721 tcagatcgac agcgtgaatg gcgacacccg cctcgtcacc ctgaccatcg gcggaaacga
 781 tgtgtcgttc gtcggcaaca tcttcgccgc cgcttgcgag aagatggcgt cgcccgatcc
 841 gcgctgcggc aagtggcggg agatcaccga ggaagagtgg caggccgacg aggagcggat
 901 gcgctccatc gtacgccaga tccacgcccg cgcgcctctc gcccgggtgg tggtggtcga
 961 ttacatcacg gtcctgccgc catcaggcac ttgcgctgcc atggcgattt cgccggaccg
1021 gctggcccag agccgcagcg ccgcgaaacg gcttgccggg attaccgcac gggtcgcgcg
1081 agaagagggt gcatcgctgc tcaagttctc gcatatctcg cgccggcacc atccatgctc
1141 tgccaagccc tggagcaacg gcctttccgc cccggccgac gacggcatcc cggtccatcc
1201 gaaccggctc ggacatgctg aagcggccgc ggcgctggtc aagcttgtga aattgatgaa
1261 gtagctactg cactgatttc aaatagtatt gcctgtcagc tttccagccc ggattgttgc
1321 agcgcaacag aaacttgtcc gtaatggatt gatggtttat gtcgctcgca aattgccgtc
1381 gaagggaacg ggcgcgtcgc tcgttaacgt cctgggtgca gcagtgacgg agcgcgtgga
1441 tgagtgatac tggcggtgtc atcggtgtac gcgccgccat tccatgcct gtacgcgccg
```
//

This enzyme comprises the sequence "GSSF" (SEQ ID NO: 39) as opposed to GDSX (SEQ ID NO: 31).

When tested it was found that this enzyme does not comprise glycolipase activity in accordance with the present invention.

Therefore, the GDSx (SEQ ID NO: 31) motif may be important when attempting to identify other suitable galactolipases.

Notably, the enzyme from *S. rimosus* that has been purified and characterised biochemically and shows about 56% sequence homology to *Streptomyces* L131 (Abramić M., et al. (1999); Vujaklija D. et al. (2002)) is known to hydrolyse neutral lipids such as triolein or nitrophenyl esters of fatty. The enzyme from *S. rimosus* may also hydrolyse galactolipase in accordance with the present invention. Similarly, two other *Streptomyces* species for which genome sequence data is available—*S. coelicolor* A2(3) and *S. avermitilis* may contain enzymes having galactolipase activity, for example (NP_625998 and NP_827753) are currently annotated in GenBank as "putative secreted hydrolases".

Many other useful homologues of *Streptomyces* L131 galactolipase can be identified by a similar approach. Suitable galactolipase/lipid acyl-transferase enzyme enzymes for use in the methods of the invention may be identified by alignment to the L131 sequence using Align X, the Clustal W pairwise alignment algorithm of VectorNTI using default settings.

Alternatively, suitable galactolipase for use in the methods of the invention may be identified by alignment to the pfam Pfam00657 consensus sequence (as described in WO04/064987).

FIG. 15 shows an sequence alignment of the L131 and homologues from *S. avermitilis* and *T. fusca*. FIG. 15 illustrates the conservation of the GDSx (SEQ ID NO: 31) motif (GDSY (SEQ ID NO: 34) in L131 and *S. avermitilis* and *T. fusca*), the GANDY (SEQ ID NO: 35) box, which is either GGNDA (SEQ ID NO: 37) or GGNDL (SEQ ID NO: 38), and the HPT block (considered to be the conserved catalytic histadine). These three conserved blocks are highlighted in FIG. 15.

When aligned to either the pfam Pfam00657 consensus sequence (as described in WO04/064987) and/or the L131 sequence herein disclosed (SEQ ID No 4) it is possible to identify three conserved regions, the GDSx block, the GANDY block and the HPT block (see WO04/064987 for further details).

EXAMPLE 10

Gene Cloning and Construction of Expression Vectors

*Corynebacterium efficiens* DSM 44549, *Thermobifida fusca* DSM 43792 and *Streptomyces avermitilis* DSM46492 were used for isolating the genes homologous to the galactolipase gene of *S. thermosacchari* L131.

The strains accorded with a DSM number are deposited and publicly available with Deutsche Sammlung von Mikroorganismen and Zellkulturen GmbH (DSM).

*Escherichia coli* strains XL-Blue MRF', BL21(DE3) (Novagen) and S17-1 (Simon R. et al., 1983), *Bacillus subtilis* BD170, *Streptomyces lividans* strain 1326 (John Innes Centre), *Corynebacterium glutamicum* DSM20300 were used as the hosts for heterologous expression. The strain of *Aeromonas salmonicida* (DSM 12609) was also used as an expression host.

*S. thermosacchari* L131, *Citrobacter freundii* P3-42 and *Enterobacter nimipressuralis* P1-60 were isolated in our laboratory from natural environment and taxonomically identified by 16S rRNA gene sequencing.

The following culture media were used in this study. LB (5 g/l yeast extract, 10 g/l tryptone, 10 g/l NaCl, pH 7.0), 2×YT (10 g/l NaCl, 10 g/l yeast extract, 16 g/l tryptone) were used for cultivation of *E. coli* and other Gram-negative bacteria. Nutrient broth (3 g/l beef extract, 5 g/l peptone, pH 7.0) was used for growing *C. efficiens* and *N. aromaticivorans*, YM-broth (3 g/l yeast extract, 3 g/l malt extract, 5 g/l peptone, 10 g/l dextrose, pH 7.0) was used for cultivation of *S. avermitilis*, Medium 65 (4 g/l glucose, 4 g/l tryptone, 10 g/l malt extract, 2 g/l $CaCO_3$, pH 7.2) was used for *T. fusca*.

DNA Isolation.

Standard alkaline lysis procedure combined with Qiagen column purification method was used for plasmid isolation. One exception was the preparative isolation of plasmid DNA from *Streptomyces*. In this case, equilibrium centrifugation in CsCl gradient was used as the final purification step.

Methods for Introduction of DNA into Microbial Strains.

Both *E. coli* and *C. glutamicum* strains were transformed by electroporation using 1 mm cuvettes and the following electroporation parameter settings: 1800V, 25° F., 200 μl *B. subtilis* BD170 was transformed by "Paris" method based on natural competence (Harwood C. R. and Cutting S. M., 1990). *Streptomyces lividans* was transformed by protoplast method (Kieser T. et al., 2000). DNA was introduced into *A. salmonicida* by conjugation with *E. coli* using filter mating method of Harayama et al. (1980).

Construction of Rifampicin-Resistant Mutant of *A. salmonicida*.

About $10^8$ cells from overnight culture of *A. salmonicida* DSM12609 were plated on a series of LB agar plates containing 5-30 mg/l rifampicin. The plates were irradiated by short wave UV light using SpectroLinker XL-1500 device (Spectronics Corp. USA). The radiation dose was 4-6 $J/M^2$. The plates were incubated at 30° C. for 2 days. Several colonies growing on 30 mg/l rifampicin were selected and additionally tested on 50 mg/l rifampicin. One clone resistant to 50 mg/l rifampicin (named R1) was chosen for subsequent work.

Construction of *E. coli* Expression Vectors for L131 Galactolipase Homologues.

The lipase gene of *Streptomyces avermitilis* was amplified by PCR using chromosomal DNA as template and the two oligonucleotide primers oSAL-5 (GGGAATTCCATAT-GAGACGTTCCCGAATTACG) (SEQ ID NO: 24) and oSAL-3 (GCATGGATCCGGTGACCTGTGCGACGG) (SEQ ID NO: 25). For amplification of lipase genes of *Thermobifida fusca* and *Corynebacterium efficiens* the oligonucleotide primers used were oTFL-5 (GGGAATTC-CATATGGGCAGCGGACCACGTG) (SEQ ID NO: 26) and oTFL-3 (GCATGGATCCGACACGCACGGCTCAACG) (SEQ ID NO: 27), oCEL-5 (GGGAATTCCATATGAGGA-CAACGGTCATCG) (SEQ ID NO: 28) and oCEL-3 (GCATGGATCCGGCATCGGGCTCATCC) (SEQ ID NO: 29), respectively. The PCR products were digested with NdeI and BamHI and ligated with pET11 a (Novagen, USA) vector digested with the same restriction endonucleases.

L131 galactolipase expression vector for *S. lividans* was constructed as follows. Plasmid pUC18(L131RX) that contains the 1.37 kb EcoRI-XbaI fragment of the original cloned DNA fragment carrying L131 lipase gene (pBK(L131)) was digested with EcoRI and ligated with EcoRI digested pIJ487 (Kieser et al., 2000). This ligation leads to the formation of the two recombinant plasmids differing in relative orientation of pIJ487 and pUC18(L131RX). For subsequent work a variant where lac promoter of the pUC18 is flanking the promoterless $neo^R$ gene of pIJ487 has been selected based on restriction analysis. This construction was named pRX487-5 (FIG. 11). Besides ampicillin resistance, this plasmid also confers *E. coli* the resistance to at least 3 mg/l kanamycin. The protoplasts of *S. lividans* 1326 were transformed with 0.1-10 μg of pRX487-5 to thiostreptone (1.2 mg/l) and kanamycin (5 mg/l) resistance. These transformants produced active galactolipase as judged by the DGDG-safranine indicator plate assay. The transformants were plated on SM plates (Kieser et al., 2000) supplemented with 5 mg/ml of kanamycin and allowed to sporulate. The resulting spores were used for inoculating shake flask and fermentor cultures.

Construction of Expression Vectors for *Corynebacterium glutamicum*.

All expression vectors used in this work are based on the plasmid pCB5 which is a shuttle vector carrying *C. glutamicum* replicon from plasmid pSR1 (Yoshihama et al., 1985) and ColE1 replicon from *E. coli*. The promoter that is used in this vector is derived from the cop1 gene encoding the major secreted protein of *C. glutamicum*—PS1. Enzymes were expressed from their native genes including unmodified signal peptides, e.g. *T. fusca* (FIG. 14).

Fermentation Conditions

Fermentation of Lipase-Producing *Streptomyces* Strains.

In shake flasks, lipase-producing recombinant *S. lividans* strains were grown in a medium containing (per liter) 10 g peptone, 5 g yeast extract, 2 g $K_2HPO_4$ and 10 g glucose (pH 7.0) supplemented with appropriate antibiotics: thiostreptone was used at 1.2 mg/l, kanamycin at 20 mg/l, chloramphenicol at 1.5 mg/l and erythromycin at 1.5 mg/l. Spore suspensions produced by growing the transformants on SM plates were used to start the cultivations.

For fed-batch fermentations, Braun Biostat E fermentor (10 l) was used. The initial medium (7 l), contained (per liter): peptone 20 g, yeast extract, 10 g, glucose 20 g and appropriate antibiotics as described above (except for thiostreptone, which was not used in 10 l cultures). The cultivation was conducted at 30° C., constant 10 l/min aeration and 600 rpm stirring rate. Inocula (2×250 ml per fermentation) were grown in 2 l Erlenmeyer flasks as described in the previous paragraph. The fermentation was carried out in batch mode for 18-20 h after which time, a solution containing 30% glucose and 12.5% peptone was fed to the fermentor culture at a rate of 0.5 ml/min. Samples (30 ml) of the culture were withdrawn aseptically twice a day.

Fermentation of Recombinant *C. glutamicum* Strains.

Shake-flask cultures of *C. glutamicum* were grown in LB containing 50 mg/l kanamycin at 30° C. and 200 rpm agitation rate.

Fermentation of Recombinant *A. salmonicida* Strains.

In shake flasks, the recombinant *A. salmonicida* strains were cultivated in 2×YT medium supplemented with streptomycin and kanamycin (at 25 mg/l). To induce tac promoter, IPTG (1-5 mM) or lactose (1-10%) were added to the growth medium.

Two sets of conditions for production of recombinant acyltransferase in *A. salmonicida* were tested at fermentor scale. In the first experiment, the initial medium (7 l) was 2×YT supplemented with 2% glucose, 50 mg/l of kanamycin and 50 mg/l of streptomycin and the feeding solution (3 l) contained 25% glucose, 10% tryptone and 5% yeast extract, 100 mg/l of both kanamycin and streptomycin. Cultivation was carried out at 10 l/min aeration, 600 rpm stirring rate and 28° C. The pH was adjusted to 7.5 by 25% $NH_3$ and 10% phosphoric acid. The fermentor was inoculated with 0.5 l of overnight culture of *A. salmonicida* and grown in batch mode for 24 h. At this point IPTG was added to 5 mM and the feeding was started at a rate of 50 ml/h.

In the second experiment, the initial medium was modified by substituting glucose with lactose. Feeding solution was 2 l of 20% lactose. The fermentation temperature was increased to 30° C. and the pH of the culture medium decreased to 7.0. Inoculation was done as in the first experiment and the feeding (100 ml/h) was started after 20 h of cultivation in the initial medium Enzyme Assays Safranine Plate Screening Method.

In safranine plate screening the bottom layer contained culture medium+additive, 1.5% agarose and 0.002% safranine (0.2% stock solution in water, sterile filtered) and the top layer 0.7% agarose, 1% DGDG and 0.002% safranine.

Determination of Galactolipase Activity (Glycolipase Activity Assay (GLU-7)):

Substrate:

0.6% digalactosyldiglyceride (Sigma D 4651), 0.4% Triton-X 100 (Sigma X-100) and 5 mM $CaCl_2$ was dissolved in 0.05M HEPES buffer pH 7.

Assay Procedure:

400 µL substrate was added to an 1.5 mL Eppendorf tube and placed in an Eppendorf Thermomixer at 37° C. for 5 minutes. At time t=0 min, 50 µL enzyme solution was added. Also a blank with water instead of enzyme was analyzed. The sample was mixed at 10×100 rpm in an Eppendorf Thermomixer at 37° C. for 10 minutes. At time t=10 min the Eppendorf tube was placed in another thermomixer at 99° C. for 10 minutes to stop the reaction.

Free fatty acid in the samples was analyzed by using the NEFA C kit from WAKO GmbH.

Enzyme activity GLU at pH 7 was calculated as micromole fatty acid produced per minute under assay conditions Determination of Phospholipase Activity (Phospholipase Activity Assay (PLU-7)):

Substrate 0.6% L-α Phosphatidylcholine 95% Plant (Avanti #441601), 0.4% Triton-X 100 (Sigma X-100) and 5 mM $CaCl_2$ was dispersed in 0.05M HEPES buffer pH 7.

Assay Procedure:

400 µL substrate was added to an 1.5 mL Eppendorf tube and placed in an Eppendorf Thermomixer at 37° C. for 5 minutes. At time t=0 min, 50 µL enzyme solution was added. Also a blank with water instead of enzyme was analyzed. The sample was mixed at 10×100 rpm in an Eppendorf Thermomixer at 37° C. for 10 minutes. At time t=10 min the Eppendorf tube was placed in another thermomixer at 99° C. for 10 minutes to stop the reaction.

Free fatty acid in the samples was analyzed by using the NEFA C kit from WAKO GmbH.

Enzyme activity PLU-7 at pH 7 was calculated as micromole fatty acid produced per minute under assay conditions.

Spectrophotometric Assay with p-nitrophenyl Palmitate (pNPP).

Lipase activity was measured with a spectrophotometric assay at 30° C. with pNPP as substrate, by using 50 mM Tris-Maleate buffer (pH 6.5) with 0.4% Triton X-100 and 0.1% gum Arabic. The substrate stock solution (100 mM) was prepared in dioxane. The kinetic measurement was started by addition of enzyme to the reaction mixture. To evaluate the initial hydrolytic activity, the increase in absorption at 410 nm was followed with Spectramax plate reader every 20 s for 20 min. One unit of lipase activity was defined as the amount of enzyme that liberated 1 µmol of p-nitrophenol per min. The activity toward other p-NP esters was measured in the same manner, by using 1 mM each substrate. (Abramic M. et al. (1999))

Determination of Effects of pH and Temperature on Lipase Activity.

For the determination of the effect of pH on enzymatic activity, it was measured over a range of pH 2-10 by using the galactolipase activity assay except that the buffers used in the experiment were as follows: pH 2-3.5 Glycine-HCl; pH 4-5 NaOAc; pH 5.5-7.5 Tris-Maleate; pH 7.5-9 Tris-HCl; pH 10 CAPS.

The effect of temperature on galactolipase stability was determined by incubating aliquots of enzyme for 20 min at various temperatures (22° C.-90° C.) following incubation on ice for 60 min. Residual activity was analysed by galactolipase activity assay.

For detection of optimal temperature for galactolipase activity, the usual assay mixture was equilibrated at the required temperature (the range 20° C.-70° C.) and 2 or 4 µl of enzyme was added to start the reaction. The activity was analysed by galactolipase activity assay, but using a shorter period of time (20 min).

EXAMPLE 11

Characterisation of Galactolipase Candidates from Biodiversity Study

The sequence of *Streptomyces thermosacchari* L131 galactolipase offers for the possibility for in silico identification of new family II galactolipases.

Many other useful homologues of *Streptomyces* L131 galactolipase can be identified, for example, "hypothetical protein" from *Thermobifida fusca* (ZP_00058717) and "hypothetical protein" from *Corynebacterium efficiens* (NP_738716).

We cloned and expressed 3 homologues of *Streptomyces* L131 galactolipase: the genes of *Streptomyces avermitilis* (SAL), *Thermobifida fusca* (TFL), and *Corynebacterium efficiens* (CEL). All genes were expressed in *E. coli* by using pET expression system. The recombinant *E. coli* strains were first analysed using DGDG—indicator plates with safranine and the enzymes of *S. avermitilis*, *T. fusca* and *C. efficiens* were found to have galactolipase activity.

The enzymes showing galactolipase activity were further examined. Substrate specificities of those galactolipase candidates were studied (FIG. 13). The activity of candidate enzymes towards DGDG, lecithin, olive oil, nitrophenyl butyrate, nitrophenyl decanoate (NP-D) and nitrophenyl palmitate was tested. The enzymes were found to have very different substrate specificity profiles. Acyl-transferase activity was tested in an assay using NP-D as substrate and quantifying both the release of nitrophenol and free fatty acids by NEFA kit. Preliminary data suggests that at least the enzyme from *Thermobifida fusca* has transferase activity towards glycerol and glucose.

Thermo-stability of galactolipase candidates was tested. It was found that the *Corynebacterium efficiens* enzyme was the most thermostable while the enzyme of *Streptomyces avermitilis* was the most thermo-sensitive.

EXAMPLE 12

*Streptomyces thermosacchari* L131 Degumming Trial

A phospholipase from *Streptomyces thermosacchari* L131 was tested in crude soya oil.

Materials and Methods
K371: *Streptomyces thermosacchari* L131 enzyme expressed in *S. lividans* freeze dried on starch.
(Activity: 108 PLU-7/g).
Lecitase Ultra (#3108) from Novozymes, Denmark
Cholesterolester, Fluka 26950
Plant Sterol Generol 122 N from Henkel, Germany
Crude soya oil from The Solae Company, Aarhus Denmark
Lecithin: L-α Phosphatidylcholine 95% Plant (Avanti #441601)
Phospholipase Activity The phospholipase assay was the same as that used in Example 10.

HPTLC
Applicator: Automatic TLC Sampler 4, CAMAG
HPTLC plate: 20×10 cm, Merck no. 1.05641. Activated 30 minutes at 160° C. before use.
Application: 1 μl of a 8% solution of oil in buffer was applied to the HPTLC plate using Automatic TLC applicator.
Running buffer 4: Chloroform:Methanol:Water 75:25:4
Running buffer 5: P-ether:Methyl-tert-butyl ketone:Acetic acid 70:30:1
Application/Elution Time:
Running buffer 4: 20 min
Running buffer 5: 10 min
TLC Development The plate was dried in an oven for 10 minutes at 160° C., cooled, and dipped into 6% cupri acetate in 16% $H_3PO_4$. Dried additionally 10 minutes at 160° C. and evaluated directly.

Degumming Experiment

*Streptomyces thermosacchari* L131 (K371) was used for degumming studies in the formulations shown in table 4.

The samples were placed at 40° C. for 18 hours with agitation, after which time a sample was collected for HPTLC analysis by dissolving the sample in Chloroform:Methanol 2:1

TABLE 4

Degumming of crude soya oil with *Streptomyces thermosacchari* L131 And Lecitase Ultra ™

| Lane | | 1 | 2 | 3 | 4 | 5 | 6 |
|---|---|---|---|---|---|---|---|
| Crude soya oil | % | 99 | 99 | 98 | 97 | 99.7 | 99 |
| K371, 10% in water | % | | 1 | 2 | 3 | | |
| Lecitase Ultra ™ #3108, 1% in water | % | | | | | 0.3 | 0.3 |
| Water | % | 1 | 0 | 0 | 0 | | 0.7 |

The results from the HPTLC analysis are shown in FIG. 16 and FIG. 17.

FIG. 16 shows TLC plate (Buffer 4) of reaction products from enzyme treatment of crude soya oil samples according to table 4. As referenced, phosphatidylcholine (PC) was also analysed. Phosphatydylethanolamine (PE) and lysophosphatidylcholine (LPC) are also indicated.

The TLC results in FIG. 16 clearly show that phosphatidylcholine was completely removed by adding *Streptomyces thermosacchari* L131 to the oil. Only the lowest dosage (lane 2) did not completely hydrolyse the phospholipids. Lecitase Ultra™ also hydrolysed the phospholipids in the oil when 5% water was available (Lane 6) but without adding extra water (Lane 5) only part of the phospholipids were hydrolysed.

FIG. 17 shows TLC (Buffer 5) of reaction products from enzyme treatment of crude soya oil samples according to table 4. As referenced, cholesterolester, monoglyceride, diglyceride, triglyceride and plant sterol. Free fatty acid (FFA) is also indicated The results shown in FIG. 17 indicate that the hydrolysis of phospholipids is coincident with the formation of free fatty acid.

CONCLUSION

The results confirm that *Streptomyces thermosacchari* L131 effectively hydrolyses phospholipids in crude soya oil and is a suitable alternative enzyme for degumming of plant oils.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

REFERENCES

Abramic M., Lescic I., Korica T., Vitale L., Saenger W., Pigac J. Purification and properties of extracellular lipase from *Streptomyces rimosus*. Enzyme and Microbial Technology 25 522-529 (1999)

Harayama S., Masataka T., Iino T. High-frequency mobilisation of the chromosome of *Escherichia coli* by a mutant of plasmid RP4 temperature sensitive for maintenance. Mol. Gen. Genet. 180, 47-56 (1980).

Harwood C. R. and Cutting S. M. Molecular biological methods for *Bacillus*. John Wiley & Sons Ltd., West Sussex, England (1990)

Kieser T., Bibb M. J., Buttner M. J., Chater K. F., Hopwood D. A. Practical *Streptomyces* genetics. The John Innes Foundation, Crowes, Norwich, England (2000)

Vujaklija D., Schroder W., Abramic M., Zou P., Lescic I., Franke P., Pigac J. A novel streptomycete lipase: cloning, sequencing and high-level expression of the *Streptomyces rimosus* GDS(L)-lipase gene. Arch. Microbiol. 178, 124-130 (2002)

Yoshihama M, Higashiro K, Rao E A, Akedo M, Shanabruch W G, Follettie M T, Walker G C, Sinskey A J. Cloning vector system for *Corynebacterium glutamicum*. J. Bacteriol. 162 (2):591-597 (1985).

The invention claimed is:

1. A method of preparing a lysoglycolipid comprising treating a substrate comprising a glycolipid with at least one lipolytic enzyme to produce said lysoglycolipid, wherein said lipolytic enzyme has glycolipase activity and wherein said lipolytic enzyme is obtainable from the genus *Corynebacterium* and wherein said lipolytic enzyme comprises at least one GDSx motif, wherein G is glycine, D is aspartic acid, S is serine and x is a hydrophobic amino acid residue selected from the group consisting of F, W, Y, H, K, M, I, L, V, A and G;
- or a GANDY block, wherein the GANDY block comprises the amino acid motif GGNDA or GGNDL, wherein G is glycine, N is asparagine, D is aspartic acid, A is alanine and L is leucine;
- or a HPT block, wherein H is histidine, P is proline and T is threonine wherein said lipolytic enzyme comprises an amino acid sequence shown as SEQ ID NO: 8 or an amino acid sequence having at least 70% identity therewith or comprises a nucleotide sequence shown as SEQ ID NO: 9 or a nucleotide sequence which has at least 70% identity therewith and which encode the said lipolytic enzyme.

2. A method according to claim 1 wherein said lipolytic enzyme is capable of transferring an acyl group from a glycolipid to one or more acyl acceptor substrates.

3. A method according to claim 1 wherein said lipolytic enzyme comprises an amino acid sequence shown as SEQ ID NO: 8 or an amino acid sequence having at least 90% identity therewith.

4. The method according to claim 1 wherein said lysoglycolipid is DGMG or MGMG.

5. The method according to claim 1 wherein said substrate is an edible oil.

6. The method according to claim 1 wherein x is the hydrophobic amino acid residue Y.

* * * * *

SEQUENCE LISTING

<160> NUMBER OF SEQ ID NOS: 39

<210> SEQ ID NO 1
<211> LENGTH: 435

<212> TYPE: DNA
<213> ORGANISM: Streptomyces sp.

<400> SEQUENCE: 1

```
gacgctgagg agcgaaagcg tggggagcga acaggattag ataccctggt agtccacgcc    60
gtaaacggtg ggcactaggt gtgggcaaca ttccacgttg tccgtgccgc agctaacgca   120
ttaagtgccc cgcctgggga gtacggccgc aaggctaaaa ctcaaaggaa ttgacggggg   180
cccgcacaag cggcggagca tgtggcttaa ttcgacgcaa cgcgaagaac cttaccaagg   240
cttgacatac accggaaacg gccagagatg tcgccccct tgtggtcggt gtacaggtgg    300
tgcatggctg tcgtcagctc gtgtcgtgag atgttcgggt taagtcccgc aacgagcgca   360
acctatcct gtgttgccag cggatccctt cggggtgcc ggggactcac gggagactgc     420
cggggtcaac tcgga                                                    435
```

<210> SEQ ID NO 2
<211> LENGTH: 435
<212> TYPE: DNA
<213> ORGANISM: Streptomyces sp.

<400> SEQUENCE: 2

```
gacgctgagg agcgaaagcg tggggagcga acaggattag ataccctggt agtccacgcc    60
gtaaacggtg ggcactaggt gtgggcaaca ttccacgttg tccgtgccgc agctaacgca   120
ttaagtgccc cgcctgggga gtacggccgc aaggctaaaa ctcaaaggaa ttgacggggg   180
cccgcacaag cggcggagca tgtggcttaa ttcgacgcaa cgcgaagaac cttaccaagg   240
cttgacatac accggaaacg gccagagatg tcgccccct tgtggtcggt gtacaggtgg    300
tgcatggctg tcgtcagctc gtgtcgtgag atgttgggtt aagtcccgca acgagcgcaa   360
cccttatcct gtgttgccag cggatccctt cggggtgcc ggggactcac gggagactgc    420
cggggtcaac tcgga                                                    435
```

<210> SEQ ID NO 3
<211> LENGTH: 1371
<212> TYPE: DNA
<213> ORGANISM: Streptomyces sp.

<400> SEQUENCE: 3

```
acaggccgat gcacggaacc gtacctttcc gcagtgaagc gctctccccc catcgttcgc    60
cgggacttca tccgcgattt tggcatgaac acttccttca acgcgcgtag cttgctacaa   120
gtgcggcaga gaccgctc gttggaggct cagtgagatt gacccgatcc ctgtcggccg     180
catccgtcat cgtcttcgcc ctgctgctcg cgctgctggg catcagcccg gcccaggcag   240
ccggcccggc ctatgtggcc ctgggggatt cctattcctc gggcaacggc gccggaagtt   300
acatcgattc gagcggtgac tgtcaccgca gcaacaacgc gtaccccgcc cgctgggcgg   360
cggccaacgc accgtcctcc ttcacccttcg cggcctgctc gggagcggtg accacggatg   420
tgatcaacaa tcagctgggc gccctcaacg cgtccaccgg cctggtgagc atcaccatcg   480
gcggcaatga cgcgggcttc gcggacgcga tgaccctg cgtcaccagc tcggacagca    540
cctgcctcaa ccgctggcc accgccacca actacatcaa caccaccctg ctcgcccggc   600
tcgacgcggt ctacagccag atcaaggccc gtgcccccaa cgcccgcgtg gtcgtcctcg   660
gctacccgcg catgtacctg gcctcgaacc cctggtactg cctgggcctg agcaacacca   720
agcgcgcggc catcaacacc accgccgaca ccctcaactc ggtgatctcc tcccgggcca   780
```

```
ccgcccacgg attccgattc ggcgatgtcc gcccgacctt caacaaccac gaactgttct    840
tcggcaacga ctggctgcac tcactcaccc tgccggtgtg ggagtcgtac caccccacca    900
gcacgggcca tcagagcggc tatctgccgg tcctcaacgc caacagctcg acctgatcaa    960
cgcacggccg tgcccgcccc gcgcgtcacg ctcggcgcgg gcgccgcagc gcgttgatca   1020
gcccacagtg ccggtgacgg tcccaccgtc acggtcgagg gtgtacgtca cggtggcgcc   1080
gctccagaag tggaacgtca gcaggaccgt ggagccgtcc ctgacctcgt cgaagaactc   1140
cggggtcagc gtgatcaccc ctcccccgta gccggggcg aaggcggcgc cgaactcctt   1200
gtaggacgtc cagtcgtgcg gcccggcgtt gccaccgtcc gcgtagaccg cttccatggt   1260
cgccagccgg tccccgcgga actcggtggg gatgtccgtg cccaaggtgg tcccggtggt   1320
gtccgagagc accgggggct cgtaccggat gatgtgcaga tccaaagaat t            1371
```

<210> SEQ ID NO 4
<211> LENGTH: 267
<212> TYPE: PRT
<213> ORGANISM: Streptomyces sp.

<400> SEQUENCE: 4

```
Met Arg Leu Thr Arg Ser Leu Ser Ala Ala Ser Val Ile Val Phe Ala
 1               5                   10                  15

Leu Leu Leu Ala Leu Leu Gly Ile Ser Pro Ala Gln Ala Ala Gly Pro
             20                  25                  30

Ala Tyr Val Ala Leu Gly Asp Ser Tyr Ser Ser Gly Asn Gly Ala Gly
         35                  40                  45

Ser Tyr Ile Asp Ser Ser Gly Asp Cys His Arg Ser Asn Asn Ala Tyr
     50                  55                  60

Pro Ala Arg Trp Ala Ala Ala Asn Ala Pro Ser Ser Phe Thr Phe Ala
 65                  70                  75                  80

Ala Cys Ser Gly Ala Val Thr Thr Asp Val Ile Asn Asn Gln Leu Gly
                 85                  90                  95

Ala Leu Asn Ala Ser Thr Gly Leu Val Ser Ile Thr Ile Gly Gly Asn
            100                 105                 110

Asp Ala Gly Phe Ala Asp Ala Met Thr Thr Cys Val Thr Ser Ser Asp
        115                 120                 125

Ser Thr Cys Leu Asn Arg Leu Ala Thr Ala Thr Asn Tyr Ile Asn Thr
    130                 135                 140

Thr Leu Leu Ala Arg Leu Asp Ala Val Tyr Ser Gln Ile Lys Ala Arg
145                 150                 155                 160

Ala Pro Asn Ala Arg Val Val Val Leu Gly Tyr Pro Arg Met Tyr Leu
                165                 170                 175

Ala Ser Asn Pro Trp Tyr Cys Leu Gly Leu Ser Asn Thr Lys Arg Ala
            180                 185                 190

Ala Ile Asn Thr Thr Ala Asp Thr Leu Asn Ser Val Ile Ser Ser Arg
        195                 200                 205

Ala Thr Ala His Gly Phe Arg Phe Gly Asp Val Arg Pro Thr Phe Asn
    210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
            260                 265
```

<210> SEQ ID NO 5
<211> LENGTH: 548
<212> TYPE: PRT
<213> ORGANISM: Thermobifida Fusca

<400> SEQUENCE: 5

```
Met Leu Pro His Pro Ala Gly Glu Arg Gly Glu Val Gly Ala Phe Phe
 1               5                  10                  15

Ala Leu Leu Val Gly Thr Pro Gln Asp Arg Arg Leu Arg Leu Glu Cys
            20                  25                  30

His Glu Thr Arg Pro Leu Arg Gly Arg Cys Gly Cys Gly Glu Arg Arg
        35                  40                  45

Val Pro Pro Leu Thr Leu Pro Gly Asp Gly Val Leu Cys Thr Thr Ser
    50                  55                  60

Ser Thr Arg Asp Ala Glu Thr Val Trp Arg Lys His Leu Gln Pro Arg
65                  70                  75                  80

Pro Asp Gly Gly Phe Arg Pro His Leu Gly Val Gly Cys Leu Leu Ala
                85                  90                  95

Gly Gln Gly Ser Pro Gly Val Leu Trp Cys Gly Arg Glu Gly Cys Arg
            100                 105                 110

Phe Glu Val Cys Arg Arg Asp Thr Pro Gly Leu Ser Arg Thr Arg Asn
        115                 120                 125

Gly Asp Ser Ser Pro Pro Phe Arg Ala Gly Trp Ser Leu Pro Pro Lys
    130                 135                 140

Cys Gly Glu Ile Ser Gln Ser Ala Arg Lys Thr Pro Ala Val Pro Arg
145                 150                 155                 160

Tyr Ser Leu Leu Arg Thr Arg Pro Asp Gly Pro Arg Gly Arg Phe
                165                 170                 175

Val Gly Ser Gly Pro Arg Ala Ala Thr Arg Arg Leu Phe Leu Gly
            180                 185                 190

Ile Pro Ala Leu Val Leu Val Thr Ala Leu Thr Leu Val Leu Ala Val
        195                 200                 205

Pro Thr Gly Arg Glu Thr Leu Trp Arg Met Trp Cys Glu Ala Thr Gln
    210                 215                 220

Asp Trp Cys Leu Gly Val Pro Val Asp Ser Arg Gly Gln Pro Ala Glu
225                 230                 235                 240

Asp Gly Glu Phe Leu Leu Leu Ser Pro Val Gln Ala Ala Thr Trp Gly
                245                 250                 255

Asn Tyr Tyr Ala Leu Gly Asp Ser Tyr Ser Ser Gly Asp Gly Ala Arg
            260                 265                 270

Asp Tyr Tyr Pro Gly Thr Ala Val Lys Gly Gly Cys Trp Arg Ser Ala
        275                 280                 285

Asn Ala Tyr Pro Glu Leu Val Ala Glu Ala Tyr Asp Phe Ala Gly His
    290                 295                 300

Leu Ser Phe Leu Ala Cys Ser Gly Gln Arg Gly Tyr Ala Met Leu Asp
305                 310                 315                 320

Ala Ile Asp Glu Val Gly Ser Gln Leu Asp Trp Asn Ser Pro His Thr
                325                 330                 335

Ser Leu Val Thr Ile Gly Ile Gly Gly Asn Asp Leu Gly Phe Ser Thr
            340                 345                 350

Val Leu Lys Thr Cys Met Val Arg Val Pro Leu Leu Asp Ser Lys Ala
        355                 360                 365

Cys Thr Asp Gln Glu Asp Ala Ile Arg Lys Arg Met Ala Lys Phe Glu
    370                 375                 380
```

| | | | | | | | | | | | | | | |
|---|---|---|---|---|---|---|---|---|---|---|---|---|---|---|
|Thr|Thr|Phe|Glu|Glu|Leu|Ile|Ser|Glu|Val|Arg|Thr|Arg|Ala|Pro|Asp|
|385| | | | |390| | | | |395| | | | |400|

Ala Arg Ile Leu Val Val Gly Tyr Pro Arg Ile Phe Pro Glu Glu Pro
            405                 410                 415

Thr Gly Ala Tyr Tyr Thr Leu Thr Ala Ser Asn Gln Arg Trp Leu Asn
        420                 425                 430

Glu Thr Ile Gln Glu Phe Asn Gln Gln Leu Ala Glu Ala Val Ala Val
    435                 440                 445

His Asp Glu Glu Ile Ala Ala Ser Gly Gly Val Gly Ser Val Glu Phe
450                 455                 460

Val Asp Val Tyr His Ala Leu Asp Gly His Glu Ile Gly Ser Asp Glu
465                 470                 475                 480

Pro Trp Val Asn Gly Val Gln Leu Arg Asp Leu Ala Thr Gly Val Thr
                485                 490                 495

Val Asp Arg Ser Thr Phe His Pro Asn Ala Ala Gly His Arg Ala Val
            500                 505                 510

Gly Glu Arg Val Ile Glu Gln Ile Glu Thr Gly Pro Gly Arg Pro Leu
        515                 520                 525

Tyr Ala Thr Phe Ala Val Val Ala Gly Ala Thr Val Asp Thr Leu Ala
    530                 535                 540

Gly Glu Val Gly
545

<210> SEQ ID NO 6
<211> LENGTH: 3000
<212> TYPE: DNA
<213> ORGANISM: Thermobifida Fusca

<400> SEQUENCE: 6

```
ggtggtgaac cagaacaccc ggtcgtcggc gtgggcgtcc aggtgcaggt gcaggttctt      60
caactgctcc agcaggatgc cgccgtggcc gtgcacgatg ccttgggca ggcctgtggt      120
ccccgacgag tacagcaccc atagcggatg gtcgaacggc agcggggtga actccagttc     180
cgcgccttcg cccgcggctt cgaactccgc ccaggacagg gtgtcggcga cagggccgca     240
gcccaggtac ggcaggacga cggtgtgctg caggctgggc atgccgtcgc gcagggcttt     300
gagcacgtca cggcggtcga agtccttacc gccgtagcgg tagccgtcca ggccagcag     360
cactttcggt tcgatctgcg cgaaccggtc gaggacgctg cgcaccccga gtcggggga     420
acaggacgac caggtcgcac cgatcgcggc gcaggcgagg aatgcggccg tcgcctcggc     480
gatgttcggc aggtaggcca cgacccggtc gccggggccc accccgaggc tgcggagggc     540
cgcagcgatc gcggcggtgc gggtccgcag ttctccccag gtccactcgg tcaacgccg     600
gagttcggac gcgtgccgga tcgccacggc tgatgggtca cggtcgcgga agatgtgctc     660
ggcgtagttg agggtggcgc cggggaacca gacggcgccg gcatggcgt cggaggcgag     720
cactgtggtg tacggggtgg cggcgcgcac ccggtagtac tcccagatcg cggaccagaa     780
tccttcgagg tcggttaccg accagcgcca cagtgcctcg tagtccggtg cgtccacacc     840
gcggtgctcc cgcacccagc gggtgaacgc ggtgaggttg gcgcgttctt tgcgctcctc     900
gtcgggactc acaggatcg gcggctgcgg cttgagtgtc atgaaacgcg accccttcgt     960
ggacggtgcg gatgcggtga gcgtcgggtg cctcccctaa cgctcccgg tgacggagtg     1020
ttgtgcacca catctagcac gcgggacgcg gaaaccgtat ggagaaaaca cctacaaccc    1080
cggccggacg gtgggtttcg gccacactta ggggtcgggt gcctgcttgc cgggcagggc    1140
```

```
agtcccgggg tgctgtggtg cgggcgggag ggctgtcgct tcgaggtgtg ccggcgggac    1200
actccgggcc tcagccgtac ccgcaacggg gacagttctc ctcccttccg ggctggatgg    1260
tcccttcccc cgaaatgcgg cgagatctcc cagtcagccc ggaaaacacc cgctgtgccc    1320
aggtactctt tgcttcgaac agacaggccg gacggtccac gggggaggtt tgtgggcagc    1380
ggaccacgtg cggcgaccag acgacggttg ttcctcggta tccccgctct tgtacttgtg    1440
acagcgctca cgctggtctt ggctgtcccg acggggcgcg agacgctgtg cgcatgtgg     1500 tgtgaggcca cccaggactg gtgcctgggg gtgccggtcg actcccgcgg acagcctgcg    1560
gaggacggca gtttctgct gctttctccg gtccaggcag cgacctgggg gaactattac     1620
gcgctcgggg attcgtactc ttcggggggac ggggcccgcg actactatcc cggcaccgcg   1680
gtgaagggcg gttgctggcg gtccgctaac gcctatccgg agctggtcgc cgaagcctac    1740
gacttcgccg acacttgtc gttcctggcc tgcagcggcc agcgcggcta cgccatgctt     1800
gacgctatcg acgaggtcgg ctcgcagctg gactggaact cccctcacac gtcgctggtg    1860
acgatcggga tcggcggcaa cgatctgggg ttctccacgg tttttgaagac ctgcatggtg   1920 cgggtgccgc tgctggacag caaggcgtgc acggaccagg aggacgctat ccgcaagcgg    1980
atggcgaaat tcgagacgac gtttgaagag ctcatcagcg aagtgcgcac ccgcgcgccg    2040
gacgcccgga tccttgtcgt gggctacccc cggatttttc cggaggaacc gaccggcgcc    2100
tactacacgc tgaccgcgag caaccagcgg tggctcaacg aaaccattca ggagttcaac    2160
cagcagctcg ccgaggctgt cgcggtccac gacgaggaga ttgccgcgtc gggcggggtg    2220
ggcagcgtgg agttcgtgga cgtctaccac gcgttggacg ccacgagat cggctcggac     2280 gagccgtggg tgaacggggt gcagttgcgg gacctcgcca ccggggtgac tgtgaccgc     2340 agtaccttcc accccaacgc cgctgggcac cgggcggtcg gtgagcgggt catcgagcag    2400
atcgaaaccg gccgggccg tccgctctat gccactttcg cggtggtggc ggggcgacc     2460 gtggacactc tcgcgggcga ggtggggtga cccggcttac cgtccggccc gcaggtctgc    2520
gagcactgcg gcgatctggt ccactgccca gtgcagttcg tcttcggtga tgaccagcgg    2580
cggggagagc cggatcgttg agccgtgcgt gtctttgacg agcacacccc gctgcaggag    2640
ccgttcgcac agttctcttc cggtggccag agtcgggtcg acgtcgatcc cagcccacag    2700
gccgatgctg cgggccgcga ccacgccgtt gccgaccagt tggtcgaggc gggcgcgcag    2760
cacgggggcg agggcgcgga catggtccag gtaagggccg tcgcggacga ggctcaccac    2820
ggcagtgccg accgcgcagg cgagggcgtt gccgccgaag tgctgccgt gctggccggg     2880 gcggatcacg tcgaagactt ccgcgtcgcc taccgccgcc gcacgggca ggatgccgcc     2940 gcccagcgct tgccgaaaca ggtagatatc ggcgtcgact ccgctgtggt cgcaggcccg    3000
```

<210> SEQ ID NO 7
<211> LENGTH: 372
<212> TYPE: PRT
<213> ORGANISM: Thermobifida Fusca

<400> SEQUENCE: 7

Val Gly Ser Gly Pro Arg Ala Ala Thr Arg Arg Leu Phe Leu Gly
 1               5                   10                  15

Ile Pro Ala Leu Val Leu Val Thr Ala Leu Thr Leu Val Leu Ala Val
                20                  25                  30

Pro Thr Gly Arg Glu Thr Leu Trp Arg Met Trp Cys Glu Ala Thr Gln
            35                  40                  45

Asp Trp Cys Leu Gly Val Pro Val Asp Ser Arg Gly Gln Pro Ala Glu
            50                  55                  60

Asp Gly Glu Phe Leu Leu Ser Pro Val Gln Ala Ala Thr Trp Gly
65                  70                  75                  80

Asn Tyr Tyr Ala Leu Gly Asp Ser Tyr Ser Gly Asp Gly Ala Arg
                85                  90                  95

Asp Tyr Tyr Pro Gly Thr Ala Val Lys Gly Cys Trp Arg Ser Ala
            100                 105                 110

Asn Ala Tyr Pro Glu Leu Val Ala Glu Ala Tyr Asp Phe Ala Gly His
            115                 120                 125

Leu Ser Phe Leu Ala Cys Ser Gly Gln Arg Gly Tyr Ala Met Leu Asp
    130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
                180                 185                 190

Cys Thr Asp Gln Glu Asp Ala Ile Arg Lys Arg Met Ala Lys Phe Glu
                195                 200                 205

Thr Thr Phe Glu Glu Leu Ile Ser Glu Val Arg Thr Arg Ala Pro Asp
    210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
                260                 265                 270

His Asp Glu Glu Ile Ala Ala Ser Gly Gly Val Gly Ser Val Glu Phe
                275                 280                 285

Val Asp Val Tyr His Ala Leu Asp Gly His Glu Ile Gly Ser Asp Glu
                290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
                340                 345                 350

Tyr Ala Thr Phe Ala Val Val Ala Gly Ala Thr Val Asp Thr Leu Ala
                355                 360                 365

Gly Glu Val Gly
            370

<210> SEQ ID NO 8
<211> LENGTH: 300
<212> TYPE: PRT
<213> ORGANISM: Corynebacterium Efficiens

<400> SEQUENCE: 8

Met Arg Thr Thr Val Ile Ala Ala Ser Ala Leu Leu Leu Leu Ala Gly
1               5                   10                  15

Cys Ala Asp Gly Ala Arg Glu Glu Thr Ala Gly Ala Pro Pro Gly Glu
                20                  25                  30

Ser Ser Gly Gly Ile Arg Glu Glu Gly Ala Glu Ala Ser Thr Ser Ile

```
                   35                  40                  45
Thr Asp Val Tyr Ile Ala Leu Gly Asp Ser Tyr Ala Ala Met Gly Gly
         50                  55                  60

Arg Asp Gln Pro Leu Arg Gly Glu Pro Phe Cys Leu Arg Ser Ser Gly
 65                  70                  75                  80

Asn Tyr Pro Glu Leu Leu His Ala Glu Val Thr Asp Leu Thr Cys Gln
                 85                  90                  95

Gly Ala Val Thr Gly Asp Leu Leu Glu Pro Arg Thr Leu Gly Glu Arg
                100                 105                 110

Thr Leu Pro Ala Gln Val Asp Ala Leu Thr Glu Asp Thr Thr Leu Val
        115                 120                 125

Thr Leu Ser Ile Gly Gly Asn Asp Leu Gly Phe Gly Glu Val Ala Gly
        130                 135                 140

Cys Ile Arg Glu Arg Ile Ala Gly Glu Asn Ala Asp Asp Cys Val Asp
145                 150                 155                 160

Leu Leu Gly Glu Thr Ile Gly Glu Gln Leu Asp Gln Leu Pro Pro Gln
                165                 170                 175

Leu Asp Arg Val His Glu Ala Ile Arg Asp Arg Ala Gly Asp Ala Gln
        180                 185                 190

Val Val Val Thr Gly Tyr Leu Pro Leu Val Ser Ala Gly Asp Cys Pro
        195                 200                 205

Glu Leu Gly Asp Val Ser Glu Ala Asp Arg Arg Trp Ala Val Glu Leu
        210                 215                 220

Thr Gly Gln Ile Asn Glu Thr Val Arg Glu Ala Ala Glu Arg His Asp
225                 230                 235                 240

Ala Leu Phe Val Leu Pro Asp Asp Ala Asp Glu His Thr Ser Cys Ala
                245                 250                 255

Pro Pro Gln Gln Arg Trp Ala Asp Ile Gln Gly Gln Gly Thr Asp Ala
                260                 265                 270

Tyr Pro Leu His Pro Thr Ser Ala Gly His Glu Ala Met Ala Ala Ala
        275                 280                 285

Val Arg Asp Ala Leu Gly Leu Glu Pro Val Gln Pro
        290                 295                 300

<210> SEQ ID NO 9
<211> LENGTH: 3000
<212> TYPE: DNA
<213> ORGANISM: Corynebacterium Efficiens

<400> SEQUENCE: 9
ttctggggtg ttatggggtt gttatcggct cgtcctgggt ggatcccgcc aggtggggta      60
ttcacggggg acttttgtgt ccaacagccg agaatgagtg ccctgagcgg tgggaatgag     120
gtgggcgggg ctgtgtcgcc atgagggggc ggcgggctct gtggtgcccc gcgaccccg      180 gccccggtga gcggtgaatg aaatccggct gtaatcagca tcccgtgccc accccgtcgg     240
ggaggtcagc gcccggagtg tctacgcagt cggatcctct cggactcggc catgctgtcg     300
gcagcatcgc gctcccgggt cttggcgtcc ctcggctgtt ctgcctgctg tccctggaag     360
gcgaaatgat caccggggag tgatacaccg tggtctcat cccggatgcc cacttcggcg      420
ccatccggca attcgggcag ctccgggtgg aagtaggtgg catccgatgc gtcggtgacg     480
ccatagtggg cgaagatctc atcctgctcg agggtgctca ggccactctc cggatcgata    540
tcgggggcgt ccttgatggc gtccttgctg aaaccgaggt gcagcttgtg gcttccaat      600 ttcgcaccac ggagcgggac gaggctggaa tgacggccga agagcccgtg gtggacctca    660
```

```
acgaaggtgg gtagtcccgt gtcatcattg aggaacacgc cctccaccgc acccagcttg      720
tggccggagt tgtcgtaggc gctggcatcc agaagggaaa cgatctcata tttgtcggtg      780
tgctcagaca tgatcttcct ttgctgtcgg tgtctggtac taccacggta gggctgaatg      840
caactgttat ttttctgtta ttttaggaat tggtccatat cccacaggct ggctgtggtc      900
aaatcgtcat caagtaatcc ctgtcacaca aaatgggtgg tgggagccct ggtcgcggtt      960
ccgtgggagg cgccgtgccc cgcaggatcg tcggcatcgg cggatctggc cggtaccccg     1020
cggtgaataa aatcattctg taaccttcat cacggttggt tttaggtatc cgccccttc      1080 gtcctgaccc cgtccccggc gcgcgggagc ccgcggttg cggtagacag gggagacgtg      1140
gacaccatga ggacaacggt catcgcagca agcgcattac tccttctcgc cggatgcgcg     1200
gatgggcccc gggaggagac cgccggtgca ccgccgggtg agtcctccgg ggcatccgg      1260 gaggagggg cggaggcgtc gacaagcatc accgacgtct acatcgccct cggggattcc      1320
tatgcggcga tgggcgggcg ggatcagccg ttacggggtg agccgttctg cctgcgctcg     1380
tccggtaatt acccggaact cctccacgca gaggtcaccg atctcacctg ccaggggcg     1440 gtgaccgggg atctgctcga acccaggacg ctggggagc gcacgctgcc ggcgcaggtg     1500
gatgcgctga cggaggacac caccctggtc accctctcca tcggggcaa tgacctcgga      1560 ttcggggagg tggcgggatg catccgggaa cggatcgccg gggagaacgc tgatgattgc     1620
gtggacctgc tgggggaaac catcggggag cagctcgatc agcttccccc gcagctggac     1680
cgcgtgcacg aggctatccg ggaccgcgcc ggggacgcgc aggttgtggt caccggttac     1740
ctgccgctcg tgtctgccgg ggactgcccc gaactggggg atgtctccga ggcggatcgt     1800
cgttgggcgg ttgagctgac cgggcagatc aacgagaccg tgcgcgaggc ggccgaacga     1860
cacgatgccc tctttgtcct gcccgacgat gccgatgagc acaccagttg tgcaccccca     1920
cagcagcgct gggcggatat ccagggccaa cagaccgatg cctatccgct gcacccgacc     1980
tccgccggcc atgaggcgat ggccgccgcc gtccgggacg cgctgggcct ggaaccggtc     2040
cagccgtagc gccgggcgcg cgcttgtcga cgaccaaccc atgccaggct gcagtcacat     2100
ccgcacatag cgcgcgcggg cgatggagta cgcaccatag aggatgagcc cgatgccgac     2160
gatgatgagc agcacactgc cgaagggttg ttccccgagg gtgcgcagag ccgagtccag     2220
acctgcggcc tgctccggat catgggccca accggcgatg acgatcaaca cccccaggat     2280
cccgaaggcg ataccacggg cgacataacc ggctgttccg gtgatgatga tcgcggtccc     2340
gacctgccct gaccccgcac ccgcctccag atcctcccgg aaatcccggg tggccccctt     2400
ccagaggttg tagacacccg cccccagtac caccagcccg gcgaccacaa ccagcaccac     2460
accccagggt tgggatagga cggtggcggt gacatcggtg gcggtctccc catcggaggt     2520
gctgccgccc cgggcgaagg tggaggtggt caccgccagg gagaagtaga ccatggccat     2580
gaccgccccc ttggcccttt ccttgaggtc ctcgcccgcc agcagctggc tcaattgcca     2640
gagtcccagg gccgccaggg cgatgacggc aacccacagg aggaactgcc cacccggagc     2700
ctccgcgatg gtggccaggg cacctgaatt cgaggcctca tcacccgaac cgccggatcc     2760
agtggcgatg cgcaccgcga tccacccgat gaggatgtgc agtatgccca ggacaatgaa     2820
accacctctg gccagggtgg tcagcgcggg gtggtcctcg gcctggtcgg cagcccgttc     2880
gatcgtccgt ttcgcggatc tggtgtcgcc cttatccata gctcccattg aaccgccttg     2940
aggggtgggc ggccactgtc agggcggatt gtgatctgaa ctgtgatgtt ccatcaaccc     3000
```

<210> SEQ ID NO 10
<211> LENGTH: 284
<212> TYPE: PRT
<213> ORGANISM: Novosphingobium Aromaticivorans

<400> SEQUENCE: 10

```
Met Gly Gln Val Lys Leu Phe Ala Arg Arg Cys Ala Pro Val Leu Leu
  1               5                  10                  15
Ala Leu Ala Gly Leu Ala Pro Ala Thr Val Ala Arg Glu Ala Pro
             20                  25                  30
Leu Ala Glu Gly Ala Arg Tyr Val Ala Leu Gly Ser Ser Phe Ala Ala
         35                  40                  45
Gly Pro Gly Val Gly Pro Asn Ala Pro Gly Ser Pro Glu Arg Cys Gly
     50                  55                  60
Arg Gly Thr Leu Asn Tyr Pro His Leu Leu Ala Glu Ala Leu Lys Leu
 65                  70                  75                  80
Asp Leu Val Asp Ala Thr Cys Ser Gly Ala Thr Thr His His Val Leu
                 85                  90                  95
Gly Pro Trp Asn Glu Val Pro Pro Gln Ile Asp Ser Val Asn Gly Asp
            100                 105                 110
Thr Arg Leu Val Thr Leu Thr Ile Gly Gly Asn Asp Val Ser Phe Val
        115                 120                 125
Gly Asn Ile Phe Ala Ala Ala Cys Glu Lys Met Ala Ser Pro Asp Pro
    130                 135                 140
Arg Cys Gly Lys Trp Arg Glu Ile Thr Glu Glu Trp Gln Ala Asp
145                 150                 155                 160
Glu Glu Arg Met Arg Ser Ile Val Arg Gln Ile His Ala Arg Ala Pro
                165                 170                 175
Leu Ala Arg Val Val Val Val Asp Tyr Ile Thr Val Leu Pro Pro Ser
            180                 185                 190
Gly Thr Cys Ala Ala Met Ala Ile Ser Pro Asp Arg Leu Ala Gln Ser
        195                 200                 205
Arg Ser Ala Ala Lys Arg Leu Ala Arg Ile Thr Ala Arg Val Ala Arg
    210                 215                 220
Glu Glu Gly Ala Ser Leu Leu Lys Phe Ser His Ile Ser Arg Arg His
225                 230                 235                 240
His Pro Cys Ser Ala Lys Pro Trp Ser Asn Gly Leu Ser Ala Pro Ala
                245                 250                 255
Asp Asp Gly Ile Pro Val His Pro Asn Arg Leu Gly His Ala Glu Ala
            260                 265                 270
Ala Ala Ala Leu Val Lys Leu Val Lys Leu Met Lys
        275                 280
```

<210> SEQ ID NO 11
<211> LENGTH: 1500
<212> TYPE: DNA
<213> ORGANISM: Novosphingobium Aromaticivorans

<400> SEQUENCE: 11

```
tgccggaact caagcggcgt ctagccgaac tcatgcccga aagcgcgtgg cactatcccg    60
aagaccaggt ctcggacgcc agcgagcgcc tgatggccgc cgaaatcacg cgcgaacagc   120
tctaccgcca gctccacgac gagctgccct atgacagtac cgtacgtccc gagaagtacc   180
tccatcgcaa ggacgttcg atcgagatcc accagcagat cgtgattgcc cgcgagacac   240
agcgtccgat cgtgctgggc aagggtggcg cgaagatcaa ggcgatcgga gaggccgcac   300
```

-continued

```
gcaaggaact tcgcaattg ctcgacacca aggtgcacct gttcctgcat gtgaaggtcg    360
acgagcgctg ggccgacgcc aaggaaatct acgaggaaat cggcctcgaa tgggtcaagt    420
gaagctcttc gcgcgccgct gcgccccagt acttctcgcc cttgccgggc tggctccggc    480
ggctacggtc gcgcgggaag caccgctggc cgaaggcgcg cgttacgttg cgctgggaag    540
ctccttcgcc gcaggtccgg gcgtggggcc caacgcgccc ggatcgcccg aacgctgcgg    600
ccggggcacg ctcaactacc cgcacctgct cgccgaggcg ctcaagctcg atctcgtcga    660
tgcgacctgc agcggcgcga cgacccacca cgtgctgggc cctggaacg aggttccccc    720 tcagatcgac agcgtgaatg cgacacccg cctcgtcacc ctgaccatcg gcggaaacga    780
tgtgtcgttc gtcggcaaca tcttcgccgc cgcttgcgag aagatggcgt cgcccgatcc    840
gcgctgcggc aagtggcggg agatcaccga ggaagagtgg caggccgacg aggagcggat    900
gcgctccatc gtacgccaga tccacgcccg cgcgcctctc gcccgggtgg tggtggtcga    960
ttacatcacg gtcctgccgc catcaggcac ttgcgctgcc atggcgattt cgccggaccg   1020
gctggcccag agccgcagcg ccgcgaaacg gcttgcccgg attaccgcac gggtcgcgcg   1080
agaagagggt gcatcgctgc tcaagttctc gcatatctcg cgccggcacc atccatgctc   1140
tgccaagccc tggagcaacg gcctttccgc cccggccgac gacggcatcc cggtccatcc   1200
gaaccggctc ggacatgctg aagcggcagc ggcgctggtc aagcttgtga aattgatgaa   1260
gtagctactg cactgatttc aaatagtatt gcctgtcagc tttccagccc ggattgttgc   1320
agcgcaacag aaacttgtcc gtaatggatt gatggtttat gtcgctcgca aattgccgtc   1380
gaagggaacg ggcgcgtcgc tcgttaacgt cctgggtgca gcagtgacgg agcgcgtgga   1440
tgagtgatac tggcggtgtc atcggtgtac gcgccgccat tcccatgcct gtacgcgccg   1500
```

<210> SEQ ID NO 12
<211> LENGTH: 268
<212> TYPE: PRT
<213> ORGANISM: Streptomyces coelicolor

<400> SEQUENCE: 12

```
Met Arg Arg Phe Arg Leu Val Gly Phe Leu Ser Ser Leu Val Leu Ala
 1               5                  10                  15

Ala Gly Ala Ala Leu Thr Gly Ala Ala Thr Ala Gln Ala Ala Gln Pro
            20                  25                  30

Ala Ala Ala Asp Gly Tyr Val Ala Leu Gly Asp Ser Tyr Ser Ser Gly
        35                  40                  45

Val Gly Ala Gly Ser Tyr Ile Ser Ser Ser Gly Asp Cys Lys Arg Ser
    50                  55                  60

Thr Lys Ala His Pro Tyr Leu Trp Ala Ala His Ser Pro Ser Thr
 65                  70                  75                  80

Phe Asp Phe Thr Ala Cys Ser Gly Ala Arg Thr Gly Asp Val Leu Ser
                85                  90                  95

Gly Gln Leu Gly Pro Leu Ser Ser Gly Thr Gly Leu Val Ser Ile Ser
            100                 105                 110

Ile Gly Gly Asn Asp Ala Gly Phe Ala Asp Thr Met Thr Thr Cys Val
        115                 120                 125

Leu Gln Ser Glu Ser Ser Cys Leu Ser Arg Ile Ala Thr Ala Glu Ala
    130                 135                 140

Tyr Val Asp Ser Thr Leu Pro Gly Lys Leu Asp Gly Val Tyr Ser Ala
145                 150                 155                 160
```

```
Ile Ser Asp Lys Ala Pro Asn Ala His Val Val Ile Gly Tyr Pro
            165                 170                 175

Arg Phe Tyr Lys Leu Gly Thr Thr Cys Ile Gly Leu Ser Glu Thr Lys
            180                 185                 190

Arg Thr Ala Ile Asn Lys Ala Ser Asp His Leu Asn Thr Val Leu Ala
            195                 200                 205

Gln Arg Ala Ala Ala His Gly Phe Thr Phe Gly Asp Val Arg Thr Thr
            210                 215                 220

Phe Thr Gly His Glu Leu Cys Ser Gly Ser Pro Trp Leu His Ser Val
225                 230                 235                 240

Asn Trp Leu Asn Ile Gly Glu Ser Tyr His Pro Thr Ala Ala Gly Gln
            245                 250                 255

Ser Gly Gly Tyr Leu Pro Val Leu Asn Gly Ala Ala
            260                 265

<210> SEQ ID NO 13
<211> LENGTH: 2000
<212> TYPE: DNA
<213> ORGANISM: Streptomyces coelicolor

<400> SEQUENCE: 13
cccggcggcc cgtgcaggag cagcagccgg cccgcgatgt cctcgggcgt cgtcttcatc      60
aggccgtcca tcgcgtcggc gaccggcgcc gtgtagttgg cccggacctc gtcccaggtg     120
cccgcggcga tctggcgggt ggtgcggtgc gggccgcgcc gaggggagac gtaccagaag     180
cccatcgtca cgttctccgg ctgccggttcg ggctcgtccg ccgctccgtc cgtcgcctcg     240
ccgagcacct tctcggcgag gtcggcgctg gtcgccgtca ccgtgacgtc ggcgccccgg     300
ctccagcgcg agatcagcag cgtccagccg tcgccctccg ccagcgtcgc gctgcggtcg     360
tcgtcgcggg cgatccgcag cacgcgcgcg ccgggcggca gcagcgtggc gccggaccgt     420
acgcggtcga tgttcgccgc gtgcgagtac ggctgctcac ccgtggcgaa acggccgagg     480
aacagcgcgt cgacgacgtc ggacggggag tcgctgtcgt ccacgttgag ccggatcggc     540
agggcttcgt gcgggttcac ggacatgtcg ccatgatcgg gcaccccgcc gccgcgtgca     600
cccgctttcc cgggcacgca cgacagggc tttctcgccg tcttccgtcc gaacttgaac     660
gagtgtcagc catttcttgg catggacact tccagtcaac gcgcgtagct gctaccacgg     720
ttgtggcagc aatcctgcta agggaggttc catgagacgt ttccgacttg tcggcttcct     780
gagttcgctc gtcctcgccg ccggcgccgc cctcaccggg gcagcgaccg cccaggcggc     840
ccaacccgcc gccgccgacg gctatgtggc cctcggcgac tcctactcct ccggggtcgg     900
agcgggcagc tacatcagct cgagcggcga ctgcaagcgc agcacgaagg cccatcccta     960
cctgtgggcg gccgcccact cgccctccac gttcgacttc accgcctgtt ccggcgcccg    1020
tacgggtgat gttctctccg gacagctcgg cccgctcagc tccggcaccg gcctcgtctc    1080
gatcagcatc ggcggcaacg acgcggtttt cgccgacacc atgacgacct gtgtgctcca    1140
gtccgagagc tcctgcctgt cgcggatcgc caccgccgag gcgtacgtcg actcgacgct    1200
gcccggcaag ctcgacggcg tctactcggc aatcagcgac aaggcgccga acgcccacgt    1260
cgtcgtcatc ggctacccgc gcttctacaa gctcggcacc acctgcatcg gcctgtccga    1320
gaccaagcgg acggcgatca acaaggcctc gaccacctc aacaccgtcc tcgcccagcg    1380
cgccgccgcc cacggcttca ccttcggcga cgtacgcacc accttcaccg gccacgagct    1440
gtgctccggc agcccctggc tgcacagcgt caactggctg aacatcggcg agtcgtacca    1500
```

```
cccccaccgcg gccggccagt ccggtggcta cctgccggtc ctcaacggcg ccgcctgacc    1560
tcaggcggaa ggagaagaag aaggagcgga gggagacgag gagtgggagg ccccgcccga    1620
cggggtcccc gtcccgtcct ccgtctccgt cccggtcccg caagtcaccg agaacgccac    1680
cgcgtcggac gtggcccgca ccggactccg cacctccacg cgcacggcac tctcgaacgc    1740
gccggtgtcg tcgtgcgtcg tcaccaccac gccgtcctgg cgcgagcgct cgccgcccga    1800
cgggaaggac agcgtccgcc accccggatc ggagaccgac ccgtccgcgg tcacccaccg    1860
gtagccgacc tccgcgggca gccgcccgac cgtgaacgtc gccgtgaacg cgggtgcccg    1920
gtcgtgcggc ggcggacagg ccccgagta gtgggtgcgc gagcccacca cggtcacctc    1980
caccgactgc gctgcggggc                                                2000
```

<210> SEQ ID NO 14
<211> LENGTH: 269
<212> TYPE: PRT
<213> ORGANISM: Streptomyces avermitilis

<400> SEQUENCE: 14

```
Met Arg Arg Ser Arg Ile Thr Ala Tyr Val Thr Ser Leu Leu Leu Ala
1               5                   10                  15

Val Gly Cys Ala Leu Thr Gly Ala Ala Thr Ala Gln Ala Ser Pro Ala
            20                  25                  30

Ala Ala Ala Thr Gly Tyr Val Ala Leu Gly Asp Ser Tyr Ser Ser Gly
        35                  40                  45

Val Gly Ala Gly Ser Tyr Leu Ser Ser Ser Gly Asp Cys Lys Arg Ser
    50                  55                  60

Ser Lys Ala Tyr Pro Tyr Leu Trp Gln Ala Ala His Ser Pro Ser Ser
65                  70                  75                  80

Phe Ser Phe Met Ala Cys Ser Gly Ala Arg Thr Gly Asp Val Leu Ala
                85                  90                  95

Asn Gln Leu Gly Thr Leu Asn Ser Ser Thr Gly Leu Val Ser Leu Thr
            100                 105                 110

Ile Gly Gly Asn Asp Ala Gly Phe Ser Asp Val Met Thr Thr Cys Val
        115                 120                 125

Leu Gln Ser Asp Ser Ala Cys Leu Ser Arg Ile Asn Thr Ala Lys Ala
    130                 135                 140

Tyr Val Asp Ser Thr Leu Pro Gly Gln Leu Asp Ser Val Tyr Thr Ala
145                 150                 155                 160

Ile Ser Thr Lys Ala Pro Ser Ala His Val Ala Val Leu Gly Tyr Pro
                165                 170                 175

Arg Phe Tyr Lys Leu Gly Gly Ser Cys Leu Ala Gly Leu Ser Glu Thr
            180                 185                 190

Lys Arg Ser Ala Ile Asn Asp Ala Asp Tyr Leu Asn Ser Ala Ile
        195                 200                 205

Ala Lys Arg Ala Ala Asp His Gly Phe Thr Phe Gly Asp Val Lys Ser
    210                 215                 220

Thr Phe Thr Gly His Glu Ile Cys Ser Ser Thr Trp Leu His Ser
225                 230                 235                 240

Leu Asp Leu Leu Asn Ile Gly Gln Ser Tyr His Pro Thr Ala Ala Gly
                245                 250                 255

Gln Ser Gly Gly Tyr Leu Pro Val Met Asn Ser Val Ala
            260                 265
```

<210> SEQ ID NO 15

<211> LENGTH: 1980
<212> TYPE: DNA
<213> ORGANISM: Streptomyces avermitilis

<400> SEQUENCE: 15

| | | | | | |
|---|---|---|---|---|---|
| ccaccgccgg | gtcggcggcg | agtctcctgg | cctcggtcgc | ggagaggttg | gccgtgtagc | 60 |
| cgttcagcgc | ggcgccgaac | gtcttcttca | ccgtgccgcc | gtactcgttg | atcaggccct | 120 |
| tgcccttgct | cgacgcggcc | ttgaagccgg | tgcccttctt | gagcgtgacg | atgtagctgc | 180 |
| ccttgatcgc | ggtggggggag | ccggcggcga | gcaccgtgcc | ctcggccggg | gtggcctggg | 240 |
| cgggcagtgc | ggtgaatccg | cccacgaggg | cgccggtcgc | cacggcggtt | atcgcggcga | 300 |
| tccggatctt | cttgctacgc | agctgtgcca | tacgagggag | tcctcctctg | ggcagcggcg | 360 |
| cgcctgggtg | gggcgcacgg | ctgtgggggg | tgcgcgcgtc | atcacgcaca | cggccctgga | 420 |
| gcgtcgtgtt | ccgccctggg | ttgagtaaag | cctcggccat | ctacggggtg | ggctcaaggg | 480 |
| agttgagacc | ctgtcatgag | tctgacatga | gcacgcaatc | aacggggccg | tgagcacccc | 540 |
| ggggcgaccc | cggaaagtgc | cgagaagtct | tggcatggac | acttcctgtc | aacacgcgta | 600 |
| gctggtacga | cggttacggc | agagatcctg | ctaaagggag | gttccatgag | acgttcccga | 660 |
| attacggcat | acgtgacctc | actcctcctc | gccgtcggct | cgccctcac | cggggcagcg | 720 |
| acggcgcagg | cgtccccagc | cgccgcggcc | acgggctatg | tggccctcgg | cgactcgtac | 780 |
| tcgtccggtg | tcggcgccgg | cagctacctc | agctccagcg | gcgactgcaa | gcgcagttcg | 840 |
| aaggcctatc | cgtacctctg | gcaggccgcg | cattcaccct | cgtcgttcag | tttcatggct | 900 |
| tgctcgggcg | ctcgtacggg | tgatgtcctg | gccaatcagc | tcggcaccct | gaactcgtcc | 960 |
| accggcctgg | tctccctcac | catcggaggc | aacgacgcgg | gcttctccga | cgtcatgacg | 1020 |
| acctgtgtgc | tccagtccga | cagcgcctgc | ctctcccgca | tcaacacggc | gaaggcgtac | 1080 |
| gtcgactcca | ccctgcccgg | ccaactcgac | agcgtgtaca | cggcgatcag | cacgaaggcc | 1140 |
| ccgtcggccc | atgtggccgt | gctgggctac | ccccgcttct | acaaactggg | cggctcctgc | 1200 |
| ctcgcgggcc | tctcggagac | caagcggtcc | gccatcaacg | acgcggccga | ctatctgaac | 1260 |
| agcgccatcg | ccaagcgcgc | cgccgaccac | ggcttcacct | cggcgacgt | caagagcacc | 1320 |
| ttcaccggcc | atgagatctg | ctccagcagc | acctggctgc | acagtctcga | cctgctgaac | 1380 |
| atcggccagt | cctaccaccc | gaccgcgccc | ggccagtccg | gcggctatct | gccggtcatg | 1440 |
| aacagcgtgg | cctgagctcc | cacggcctga | attttttaagg | cctgaatttt | taaggcgaag | 1500 |
| gtgaaccgga | agcggaggcc | ccgtccgtcg | gggtctccgt | cgcacaggtc | accgagaacg | 1560 |
| gcacggagtt | ggacgtcgtg | cgcaccgggt | cgcgcacctc | gacggcgatc | tcgttcgaga | 1620 |
| tcgttccgct | cgtgtcgtac | gtggtgacga | acacctgctt | ctgctgggtc | tttccgccgc | 1680 |
| tcgccgggaa | ggacagcgtc | ttccagcccg | gatccgggac | ctcgcccttc | ttggtcaccc | 1740 |
| agcggtactc | cacctcgacc | ggcacccggc | ccaccgtgaa | ggtcgccgtg | aacgtgggcg | 1800 |
| cctgggcggt | gggcggcggg | caggcaccgg | agtagtcggt | gtgcacgccg | gtgaccgtca | 1860 |
| ccttcacgga | ctgggccggc | ggggtcgtcg | taccgccgcc | gccaccgccg | cctcccggag | 1920 |
| tggagcccga | gctgtggtcg | ccccgccgt | cggcgttgtc | gtcctcgggg | gttttcgaac | 1980 |

<210> SEQ ID NO 16
<211> LENGTH: 372
<212> TYPE: PRT
<213> ORGANISM: Thermobifida Fusca

<400> SEQUENCE: 16

```
Met Gly Ser Gly Pro Arg Ala Ala Thr Arg Arg Leu Phe Leu Gly
 1               5                  10                  15

Ile Pro Ala Leu Val Leu Val Thr Ala Leu Thr Leu Val Leu Ala Val
             20                  25                  30

Pro Thr Gly Arg Glu Thr Leu Trp Arg Met Trp Cys Glu Ala Thr Gln
         35                  40                  45

Asp Trp Cys Leu Gly Val Pro Val Asp Ser Arg Gly Gln Pro Ala Glu
     50                  55                  60

Asp Gly Glu Phe Leu Leu Leu Ser Pro Val Gln Ala Ala Thr Trp Gly
 65                  70                  75                  80

Asn Tyr Tyr Ala Leu Gly Asp Ser Tyr Ser Gly Asp Gly Ala Arg
                 85                  90                  95

Asp Tyr Tyr Pro Gly Thr Ala Val Lys Gly Cys Trp Arg Ser Ala
                100                 105                 110

Asn Ala Tyr Pro Glu Leu Val Ala Glu Ala Tyr Asp Phe Ala Gly His
             115                 120                 125

Leu Ser Phe Leu Ala Cys Ser Gly Gln Arg Gly Tyr Ala Met Leu Asp
    130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
                180                 185                 190

Cys Thr Asp Gln Glu Asp Ala Ile Arg Lys Arg Met Ala Lys Phe Glu
                195                 200                 205

Thr Thr Phe Glu Glu Leu Ile Ser Glu Val Arg Thr Arg Ala Pro Asp
    210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
                260                 265                 270

His Asp Glu Glu Ile Ala Ala Ser Gly Gly Val Gly Ser Val Glu Phe
                275                 280                 285

Val Asp Val Tyr His Ala Leu Asp Gly His Glu Ile Gly Ser Asp Glu
    290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
                340                 345                 350

Tyr Ala Thr Phe Ala Val Val Ala Gly Ala Thr Val Asp Thr Leu Ala
                355                 360                 365

Gly Glu Val Gly
            370

<210> SEQ ID NO 17
<211> LENGTH: 968
<212> TYPE: DNA
<213> ORGANISM: Thermobifida Fusca
```

<400> SEQUENCE: 17

```
ctgcagacac cgccccgcc ttctcccgga tcgtcatgtt cggcgactcc ctcagcgaca    60
ccggcaagat gtactccaag atgcgcggct acctgccgtc ctccccgccg tactacgagg   120
gccgcttctc gaacggcccg gtctggctgg agcagctgac gaagcagttc cccggcctga   180
cgatcgccaa cgaggccgag gggggcgcga ccgcagtcgc ctacaacaag atctcctgga   240
acccgaagta ccaggtcatt aacaacctcg actacgaggt cacccagttc ttgcagaagg   300
actcgttcaa gcccgacgac ctggtcatcc tgtgggtggg cgccaacgac tacctggcct   360
acggttggaa cacggagcag gacgccaagc gggtgcgcga cgccatctcg gacgcggcaa   420
accgcatggt cctgaacggc gcgaagcaga tcctgctgtt caacctgccc gacctgggcc   480
agaacccgtc cgcccgctcc agaaggtcg tcgaggccgt ctcgcacgtg tccgcctacc   540
acaacaagct gctcctcaac ctcgcccggc agctcgcccc gacgggcatg gtcaagctgt   600
tcgagatcga caagcagttc gcggagatgc tgcgcgaccc ccagaacttc ggcctgagcg   660
acgtggagaa cccgtgctac gacggcggct acgtgtggaa gccgttcgcc acccggtccg   720
tctcgaccga ccggcagctg tcggccttct cgccccagga gcgcctggcg atcgctggca   780
acccgctcct ggcacaggcg gtagcttcgc cgatggcccg ccgctcggcc tcgcccctca   840
actgcgaggg caagatgttc tgggaccagg tccaccccac caccgtggtc cacgccgccc   900
tctcggagcg cgccgccacc ttcatcgaga cccagtacga gttcctcgcc cactagtcta   960
gaggatcc                                                           968
```

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 18

```
cagcmgccgc ggtaatwc                                                 18
```

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic primer

<400> SEQUENCE: 19

```
acgggcggtg tgtrc                                                    15
```

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 20

```
ggtgaattca tgagattgac ccgatccctg tcgg                               34
```

<210> SEQ ID NO 21
<211> LENGTH: 30
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 21
acttctagag cggcgccacc gtgacgtaca                                    30

<210> SEQ ID NO 22
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggtcatgcta gcatgagatt gacccgatcc ctgtcgg                            37

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gcatggatcc gcggcgccac cgtgacgtac a                                  31

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gggaattcca tatgagacgt tcccgaatta cg                                 32

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcatggatcc ggtgacctgt gcgacgg                                       27

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gggaattcca tatgggcagc ggaccacgtg                                    30

<210> SEQ ID NO 27
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 27
gcatggatcc gacacgcacg gctcaacg                                        28

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gggaattcca tatgaggaca acggtcatcg                                      30

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcatggatcc ggcatcgggc tcatcc                                          26

<210> SEQ ID NO 30
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30
```

Met Arg Arg Ser Arg Phe Leu Ala Ala Leu Ile Leu Leu Thr Leu Ala
 1               5                   10                  15

Ala Leu Gly Ala Ala Ala Arg Ala Ala Pro Ala Ala Tyr Val Ala Leu
             20                  25                  30

Gly Asp Ser Tyr Ser Ser Gly Ala Gly Ser Tyr Ser Ser Gly Asp
         35                  40                  45

Cys Arg Ser Thr Lys Ala Tyr Pro Ala Leu Trp Ala Ala His Ala
     50                  55                  60

Ser Ser Phe Ser Phe Ala Cys Ser Gly Ala Arg Thr Tyr Asp Val Leu
 65                  70                  75                  80

Ala Gln Leu Leu Asn Ser Thr Leu Val Ser Ile Thr Ile Gly Gly Asn
                 85                  90                  95

Asp Ala Gly Phe Ala Asp Met Thr Thr Cys Val Leu Ser Asp Ser Ala
            100                 105                 110

Cys Leu Arg Ile Ala Ala Lys Tyr Ile Thr Leu Pro Ala Arg Leu Asp
        115                 120                 125

Ser Val Tyr Ser Ala Ile Thr Arg Ala Pro Ala Arg Val Val Val Leu
    130                 135                 140

Gly Tyr Pro Arg Ile Tyr Ser Gly Leu Gly Leu Ser Thr Lys Arg Ala
145                 150                 155                 160

Ala Ile Asn Asp Ala Ala Asp Leu Asn Ser Val Ile Ala Lys Arg Ala
                165                 170                 175

Ala Asp His Gly Phe Thr Phe Gly Asp Val Thr Phe Gly His Glu Leu

```
                       180                 185                 190
Cys Ser Ala Pro Trp Leu His Ser Leu Thr Leu Pro Val Ser Tyr His
            195                 200                 205

Pro Thr Ala Gly His Ala Ala Gly Tyr Leu Pro Val Leu Asn Ser Ile
        210                 215                 220

Thr
225

<210> SEQ ID NO 31
<211> LENGTH: 4
<212> TYPE: PRT
<213> ORGANISM: Artificial Sequence
<220> FEATURE:
<221> NAME/KEY: MOD_RES
<222> LOCATION: (4)
<223> OTHER INFORMATION: Variable amino acid
<220> FEATURE:
<223> OTHER INFORMATION: Description of Artificial Sequence: Synthetic
      peptide

<400> SEQUENCE: 31

Gly Asp Ser Xaa
  1

<210> SEQ ID NO 32
<211> LENGTH: 5
<212> TYPE: PRT
<213> ORGANISM: Artificial Sequence
<220> FEATURE:
<221> NAME/KEY: MOD_RES
<222> LOCATION: (5)
<223> OTHER INFORMATION: Tyr, Ala or Leu
<220> FEATURE:
<223> OTHER INFORMATION: Description of Artificial Sequence: Synthetic
      peptide

<400> SEQUENCE: 32

Gly Ala Asn Asp Xaa
  1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 33

His His His His His His
  1               5

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Asp Ser Tyr
  1
```

```
<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Ala Asn Asp Tyr
 1               5

<210> SEQ ID NO 36
<211> LENGTH: 5
<212> TYPE: PRT
<213> ORGANISM: Artificial Sequence
<220> FEATURE:
<221> NAME/KEY: MOD_RES
<222> LOCATION: (5)
<223> OTHER INFORMATION: Variable amino acid
<220> FEATURE:
<223> OTHER INFORMATION: Description of Artificial Sequence: Synthetic
      peptide

<400> SEQUENCE: 36

Gly Gly Asn Asp Xaa
 1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Asn Asp Ala
 1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Gly Asn Asp Leu
 1               5

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Ser Ser Phe
 1
```